(12) United States Patent
Houser et al.

(10) Patent No.: US 7,338,441 B2
(45) Date of Patent: Mar. 4, 2008

(54) SUPERELASTIC/SHAPE MEMORY TISSUE STABILIZERS AND SURGICAL INSTRUMENTS

(76) Inventors: Russell A. Houser, 1787 Verdite St., Livermore, CA (US) 94550; William D. Hare, 5130 Newport Ave., Bethesda, MD (US) 20816

( * ) Notice: Subject to any disclaimer, the term of this patent is extended or adjusted under 35 U.S.C. 154(b) by 277 days.

(21) Appl. No.: 10/235,486

(22) Filed: Sep. 6, 2002

(65) Prior Publication Data
US 2003/0060685 A1   Mar. 27, 2003

Related U.S. Application Data

(60) Provisional application No. 60/317,182, filed on Sep. 6, 2001.

(51) Int. Cl.
*A61B 1/32* (2006.01)
(52) U.S. Cl. ........................................ 600/206
(58) Field of Classification Search ................ 600/184, 600/201, 203, 205, 206, 215
See application file for complete search history.

(56) References Cited

U.S. PATENT DOCUMENTS

| | | | |
|---|---|---|---|
| 4,254,763 A * | 3/1981 | McCready et al. ......... 600/230 |
| 4,353,358 A * | 10/1982 | Emerson ..................... 600/139 |
| 5,531,664 A * | 7/1996 | Adachi et al. .............. 600/149 |
| 5,597,378 A | 1/1997 | Jervis | |
| 5,727,569 A | 3/1998 | Benetti et al. | |
| 5,749,892 A | 5/1998 | Vierra et al. | |
| 5,782,746 A | 7/1998 | Wright | |
| 5,807,243 A | 9/1998 | Vierra et al. | |
| 5,810,717 A * | 9/1998 | Maeda et al. ............... 600/151 |
| 5,836,311 A | 11/1998 | Borst et al. | |
| 5,846,247 A * | 12/1998 | Unsworth et al. .......... 606/108 |
| 5,875,782 A | 3/1999 | Ferrari et al. | |
| 5,894,843 A | 4/1999 | Benetti et al. | |
| 5,899,425 A | 5/1999 | Corey Jr. et al. | |
| 5,904,657 A * | 5/1999 | Unsworth et al. .......... 600/585 |
| 5,906,607 A | 5/1999 | Taylor et al. | |
| 5,921,979 A | 7/1999 | Kovac et al. | |
| 5,927,284 A | 7/1999 | Borst et al. | |

(Continued)

FOREIGN PATENT DOCUMENTS

EP        0 646 357 A1    4/1995

(Continued)

*Primary Examiner*—Anuradha Ramana
(74) *Attorney, Agent, or Firm*—William D. Hare

(57) ABSTRACT

A surgical instrument is used for temporary use in a medical procedure in a mammalian body. The surgical instrument is configured to be changed between two shapes upon application of one or both of heating and cooling. The instrument includes a first member, a second member having a surface configured to contact tissue, and a means to apply heating or cooling to one or both of the first member and the second member to change the shape between a first shape and a second shape. A surgical instrument also may be configured to be changed between two shapes upon removal of a constraining force. The surgical instrument includes a first member, a second member having a surface configured to contact tissue, and a constraining means to apply a constraining force to one or both of the first member and the second member to cause one or both of the first member and the second member to be in a first constrained shape. The surgical instruments may be used in minimally invasive valve surgery.

19 Claims, 44 Drawing Sheets

U.S. PATENT DOCUMENTS

| | | | |
|---|---|---|---|
| 5,947,896 A | 9/1999 | Sherts et al. | |
| 5,957,835 A | 9/1999 | Anderson et al. | |
| 5,972,020 A | 10/1999 | Carpentier et al. | |
| 5,976,069 A | 11/1999 | Navia et al. | |
| 5,997,526 A * | 12/1999 | Giba et al. | 604/531 |
| 6,015,378 A | 1/2000 | Borst et al. | |
| 6,017,304 A | 1/2000 | Vierra et al. | |
| 6,019,722 A | 2/2000 | Spence et al. | |
| 6,032,672 A | 3/2000 | Taylor | |
| 6,036,641 A * | 3/2000 | Taylor et al. | 600/231 |
| 6,050,266 A | 4/2000 | Benetti et al. | |
| 6,083,170 A * | 7/2000 | Ben-Haim | 600/463 |
| 6,120,436 A | 9/2000 | Anderson et al. | |
| 6,139,492 A | 10/2000 | Vierra et al. | |
| 6,149,583 A | 11/2000 | Vierra et al. | |
| 6,159,201 A | 12/2000 | Hamilton et al. | |
| 6,206,827 B1 | 3/2001 | Chin et al. | |
| 6,210,323 B1 | 4/2001 | Gilhuly et al. | |
| 6,213,941 B1 | 4/2001 | Benetti et al. | |
| 6,231,506 B1 | 5/2001 | Hu et al. | |
| 6,231,585 B1 | 5/2001 | Takahashi et al. | |
| 6,251,065 B1 | 6/2001 | Kochamba et al. | |
| 6,258,069 B1 | 7/2001 | Carpentier et al. | |
| 6,290,644 B1 | 9/2001 | Green et al. | |
| 6,315,717 B1 | 11/2001 | Benetti et al. | |
| 6,322,500 B1 | 11/2001 | Sikora et al. | |
| 6,328,688 B1 * | 12/2001 | Borst et al. | 600/37 |
| 6,331,157 B2 | 12/2001 | Hancock | |
| 6,331,158 B1 | 12/2001 | Hu et al. | |
| 6,334,843 B1 | 1/2002 | Borst et al. | |
| 6,336,898 B1 | 1/2002 | Borst et al. | |
| 6,338,712 B2 | 1/2002 | Spence et al. | |
| 6,346,077 B1 | 2/2002 | Taylor et al. | |
| 6,350,229 B1 | 2/2002 | Borst et al. | |
| 6,361,493 B1 | 3/2002 | Spence et al. | |
| 6,364,826 B1 | 4/2002 | Borst et al. | |
| 6,371,906 B1 | 4/2002 | Borst et al. | |
| 6,390,976 B1 | 5/2002 | Spence et al. | |
| 6,394,948 B1 | 5/2002 | Borst et al. | |
| 6,394,951 B1 | 5/2002 | Taylor et al. | |
| 6,398,726 B1 | 6/2002 | Ramans et al. | |
| 6,406,424 B1 | 6/2002 | Williamson et al. | |
| 6,447,443 B1 * | 9/2002 | Keogh et al. | 600/37 |
| 6,464,629 B1 | 10/2002 | Boone et al. | |
| 6,464,630 B1 | 10/2002 | Borst et al. | |
| 6,464,699 B1 | 10/2002 | Swanson | 606/41 |
| 6,503,245 B2 | 1/2003 | Palmer et al. | |
| 6,511,416 B1 | 1/2003 | Green et al. | |
| 6,565,508 B2 | 5/2003 | Scirica et al. | |
| 6,733,517 B1 * | 5/2004 | Collins | 607/105 |
| 6,767,347 B2 * | 7/2004 | Sharkey et al. | 606/41 |
| 6,770,070 B1 * | 8/2004 | Balbierz | 606/41 |
| 2001/0002429 A1 | 5/2001 | Hu et al. | 600/210 |
| 2001/0020121 A1 | 9/2001 | Hu et al. | 600/232 |
| 2001/0025136 A1 | 9/2001 | Leonard et al. | 600/210 |
| 2001/0041827 A1 | 11/2001 | Spence et al. | 600/201 |
| 2001/0044572 A1 | 11/2001 | Benetti et al. | 600/235 |
| 2002/0010388 A1 | 1/2002 | Taylor et al. | 600/204 |
| 2002/0040182 A1 | 4/2002 | Benetti et al. | 600/210 |
| 2002/0042595 A1 | 4/2002 | Palmer et al. | 604/178 |
| 2002/0042603 A1 | 4/2002 | Palmer et al. | 606/1 |
| 2002/0045888 A1 | 4/2002 | Ramans et al. | 606/1 |
| 2002/0049369 A1 | 4/2002 | Spence et al. | 600/210 |
| 2002/0065451 A1 | 5/2002 | Spence et al. | 600/201 |
| 2002/0099268 A1 | 7/2002 | Paul et al. | 600/201 |
| 2002/0111537 A1 | 8/2002 | Taylor et al. | 600/210 |
| 2002/0120177 A1 | 8/2002 | Borst et al. | 600/37 |
| 2002/0124856 A1 | 9/2002 | Borst et al. | 128/898 |
| 2002/0137982 A1 | 9/2002 | Taylor | 600/37 |
| 2002/0161277 A1 | 10/2002 | Boone et al. | 600/37 |
| 2002/0161285 A1 | 10/2002 | Spence et al. | 600/210 |
| 2002/0165434 A1 | 11/2002 | Willamson et al. | 600/201 |
| 2003/0036677 A1 | 2/2003 | Taylor | 600/37 |
| 2003/0055318 A1 | 3/2003 | Vierra et al. | 600/204 |
| 2003/0078470 A1 | 4/2003 | Borst et al. | 600/37 |
| 2003/0088150 A1 | 5/2003 | Green et al. | 600/37 |
| 2003/0097082 A1 * | 5/2003 | Purdy et al. | 600/594 |
| 2003/0120268 A1 | 6/2003 | Bertolero et al. | 606/32 |
| 2003/0125604 A1 | 7/2003 | Kochamba et al. | 606/37 |
| 2003/0158464 A1 | 8/2003 | Bertolero | 600/116 |
| 2004/0102771 A1 | 5/2004 | Bertolero et al. | 606/41 |

FOREIGN PATENT DOCUMENTS

| | | |
|---|---|---|
| EP | 0 791 330 A2 | 8/1997 |
| EP | 0 791 330 A3 | 11/1997 |
| EP | 0 993 806 A2 | 4/2000 |
| WO | WO 97/10753 | 3/1997 |

* cited by examiner

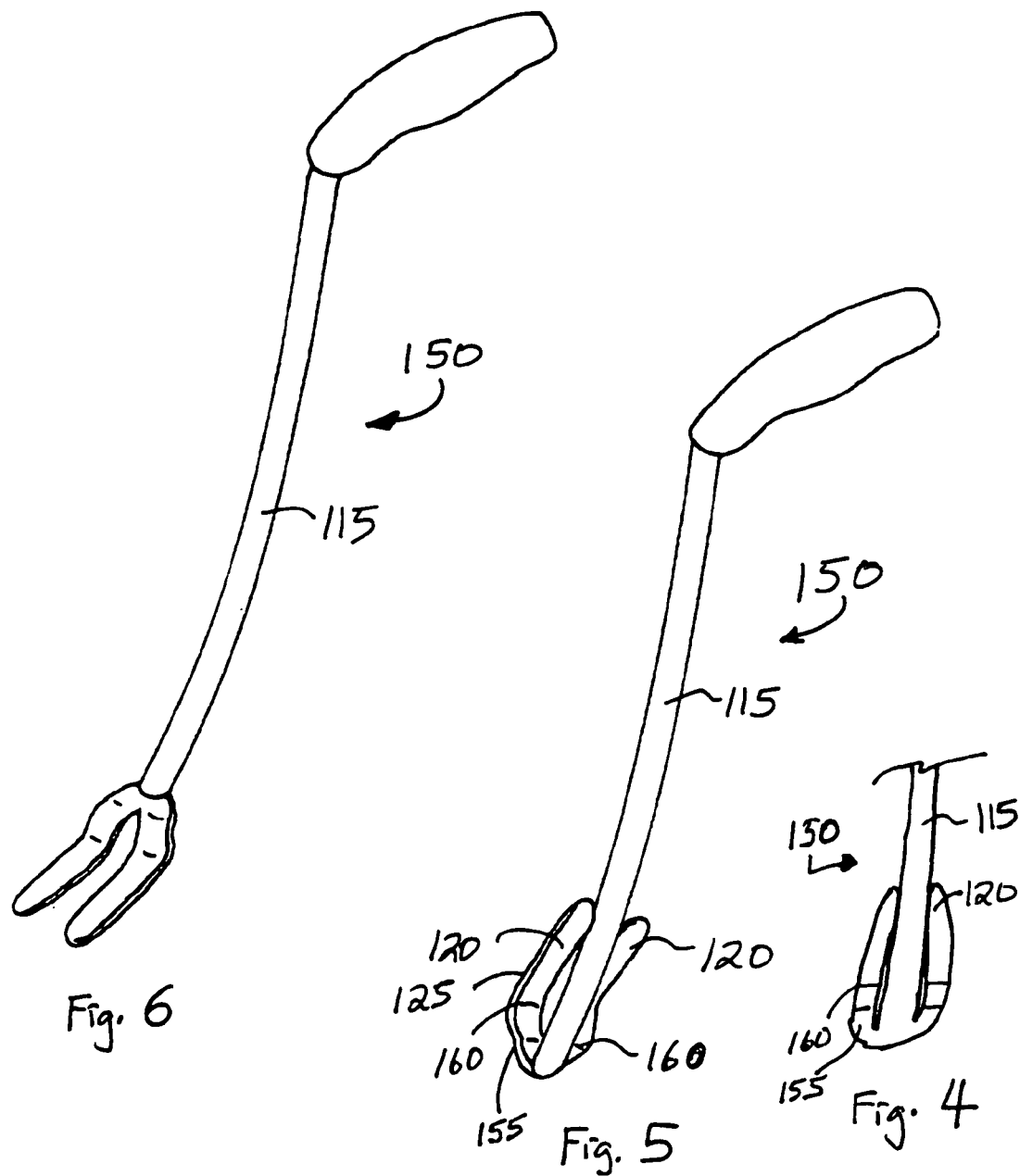

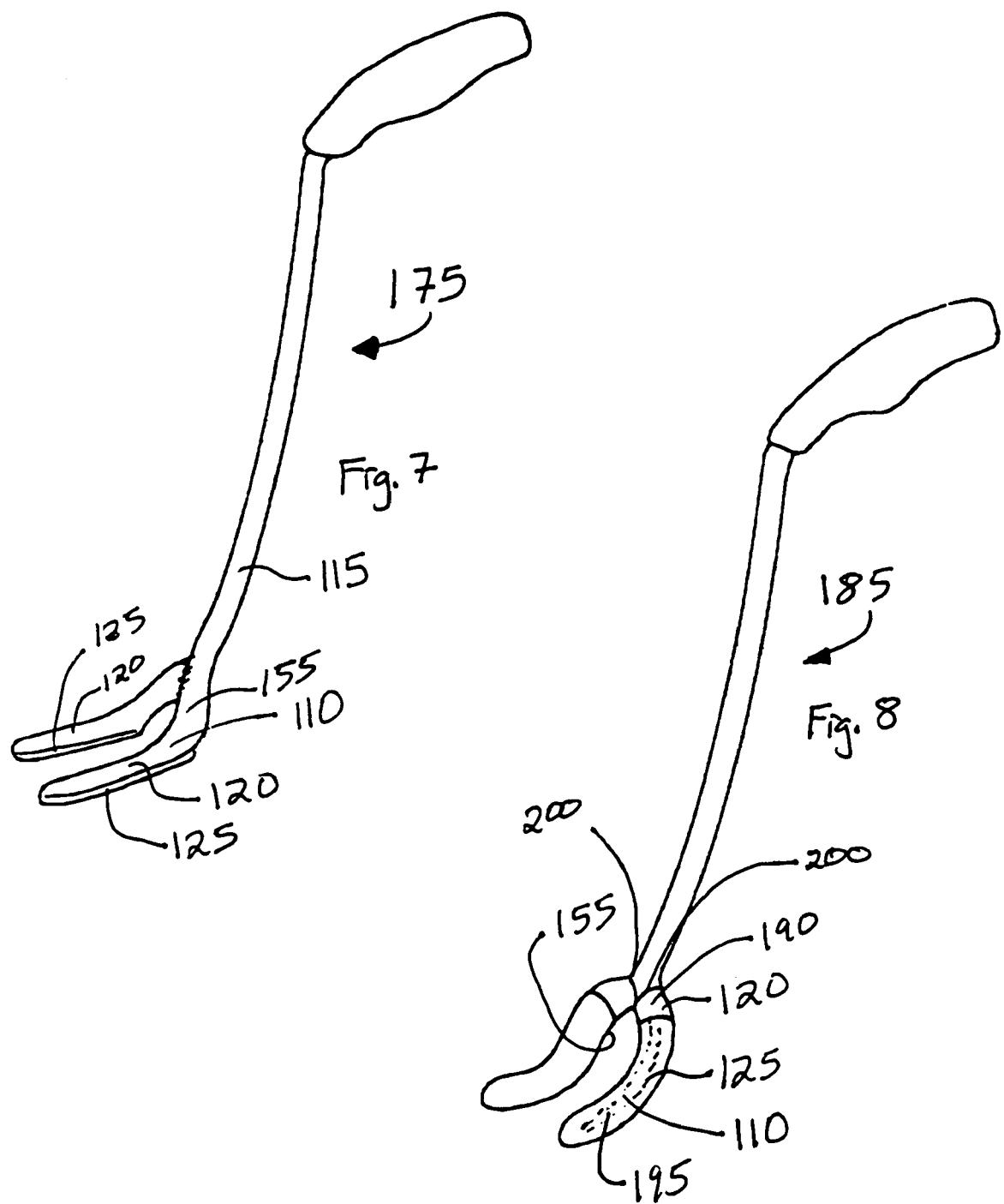

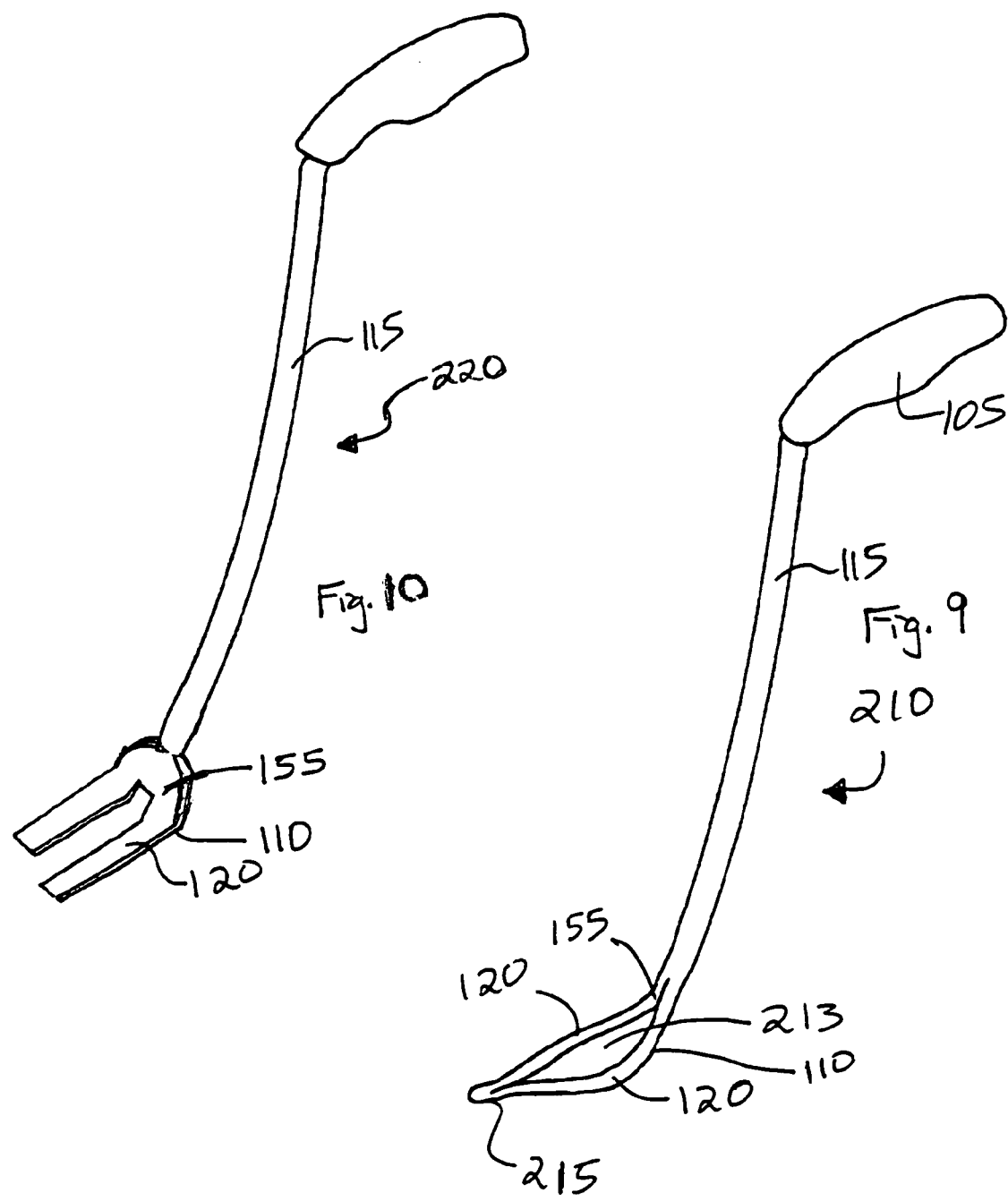

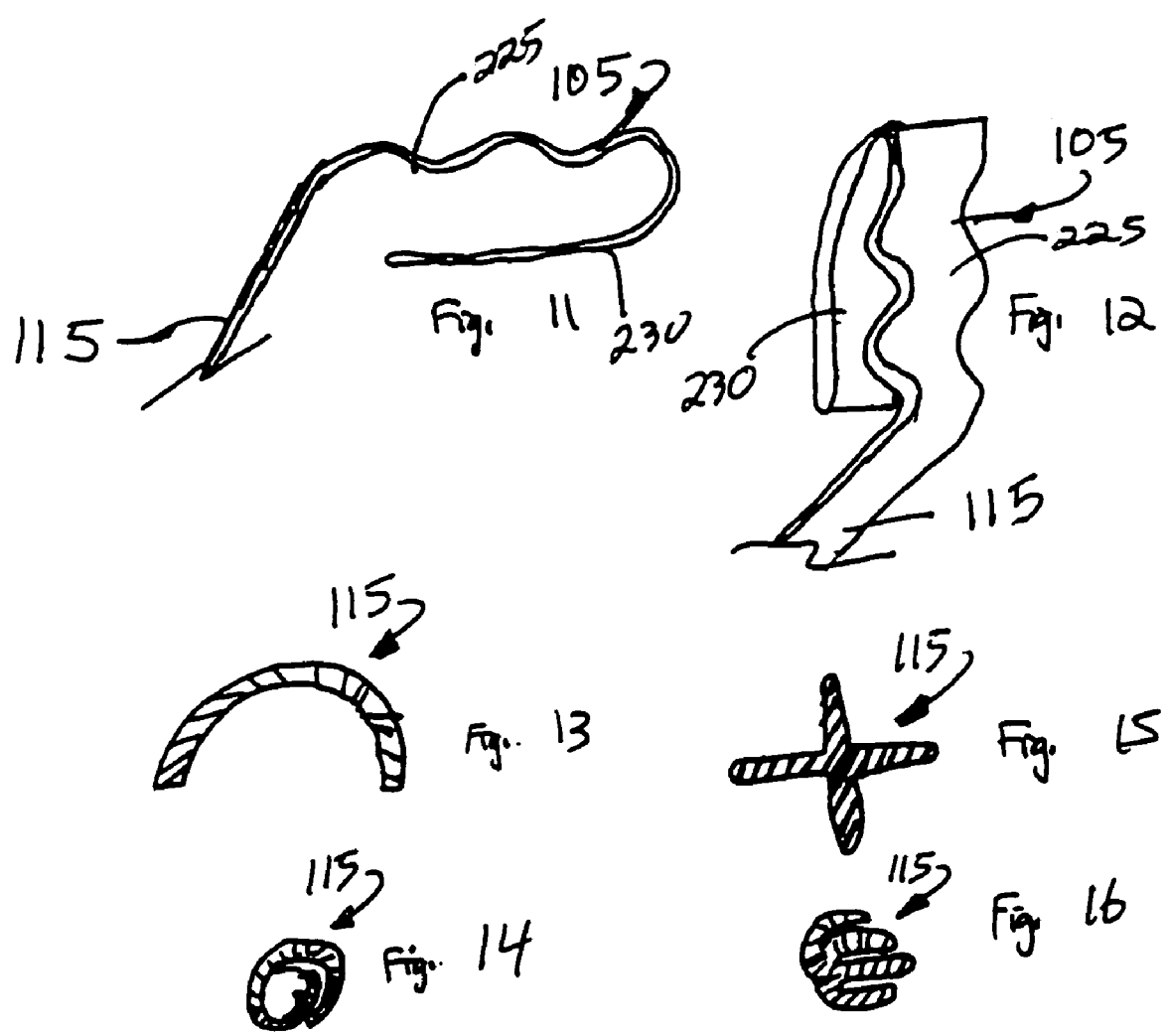

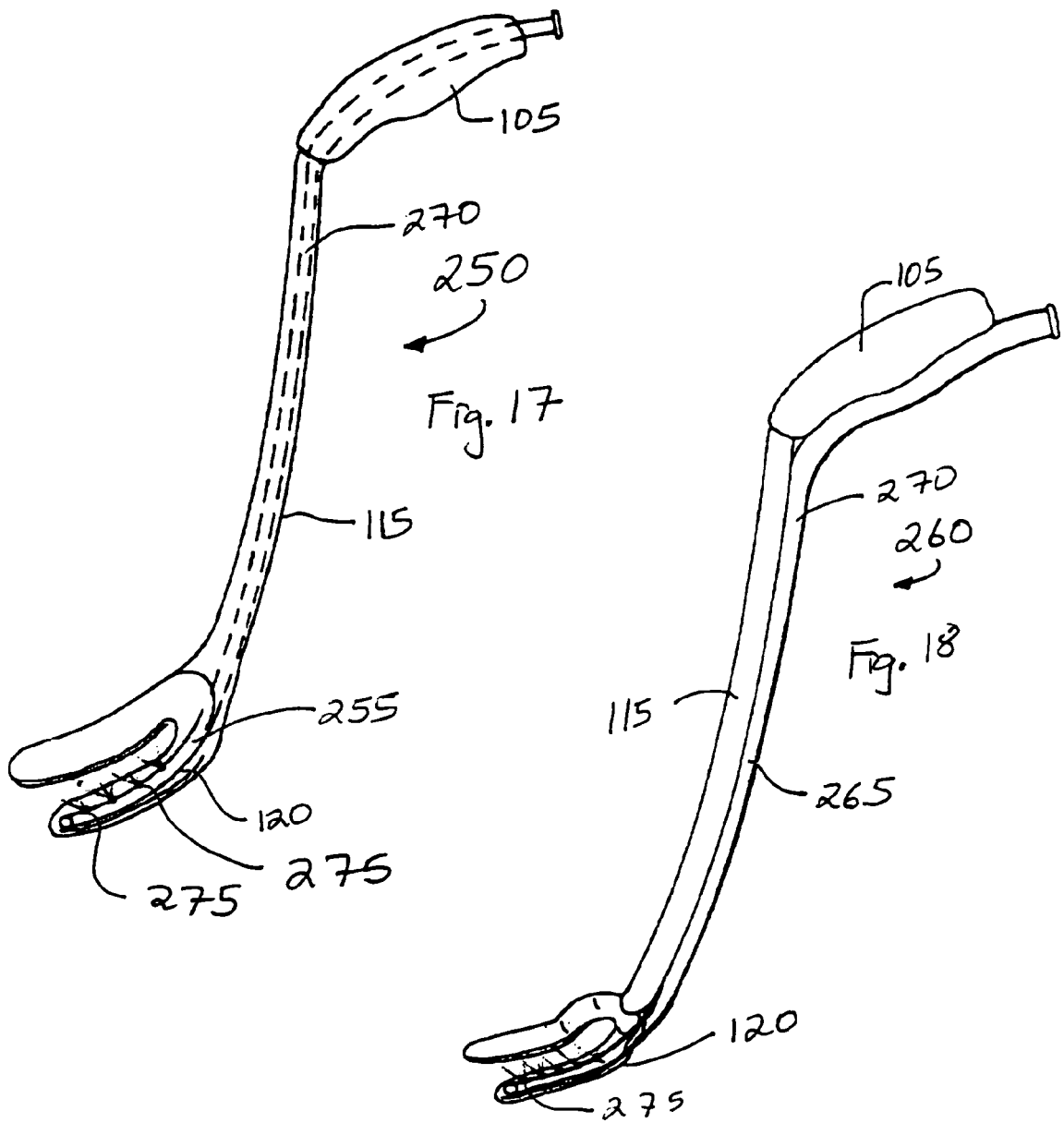

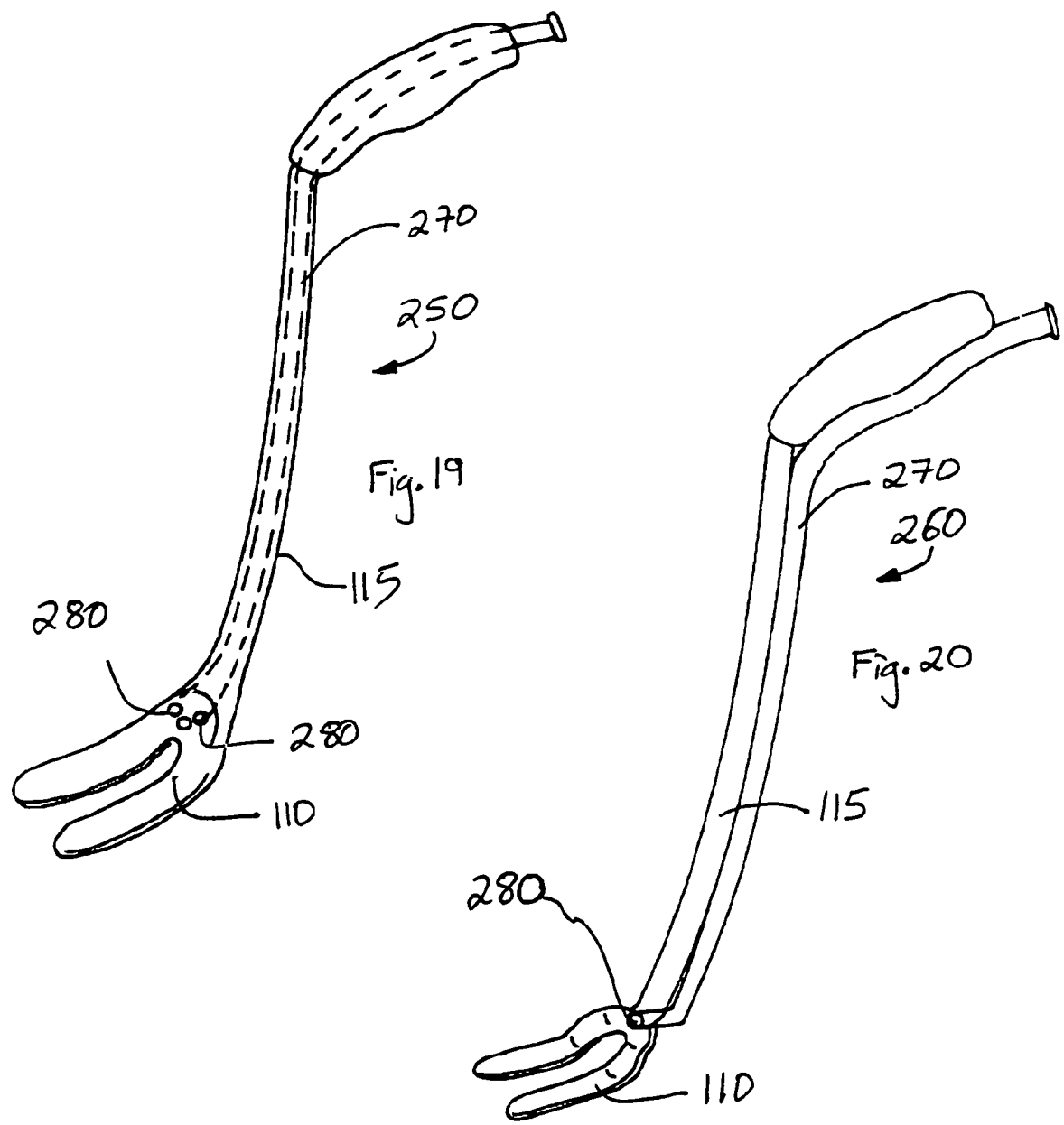

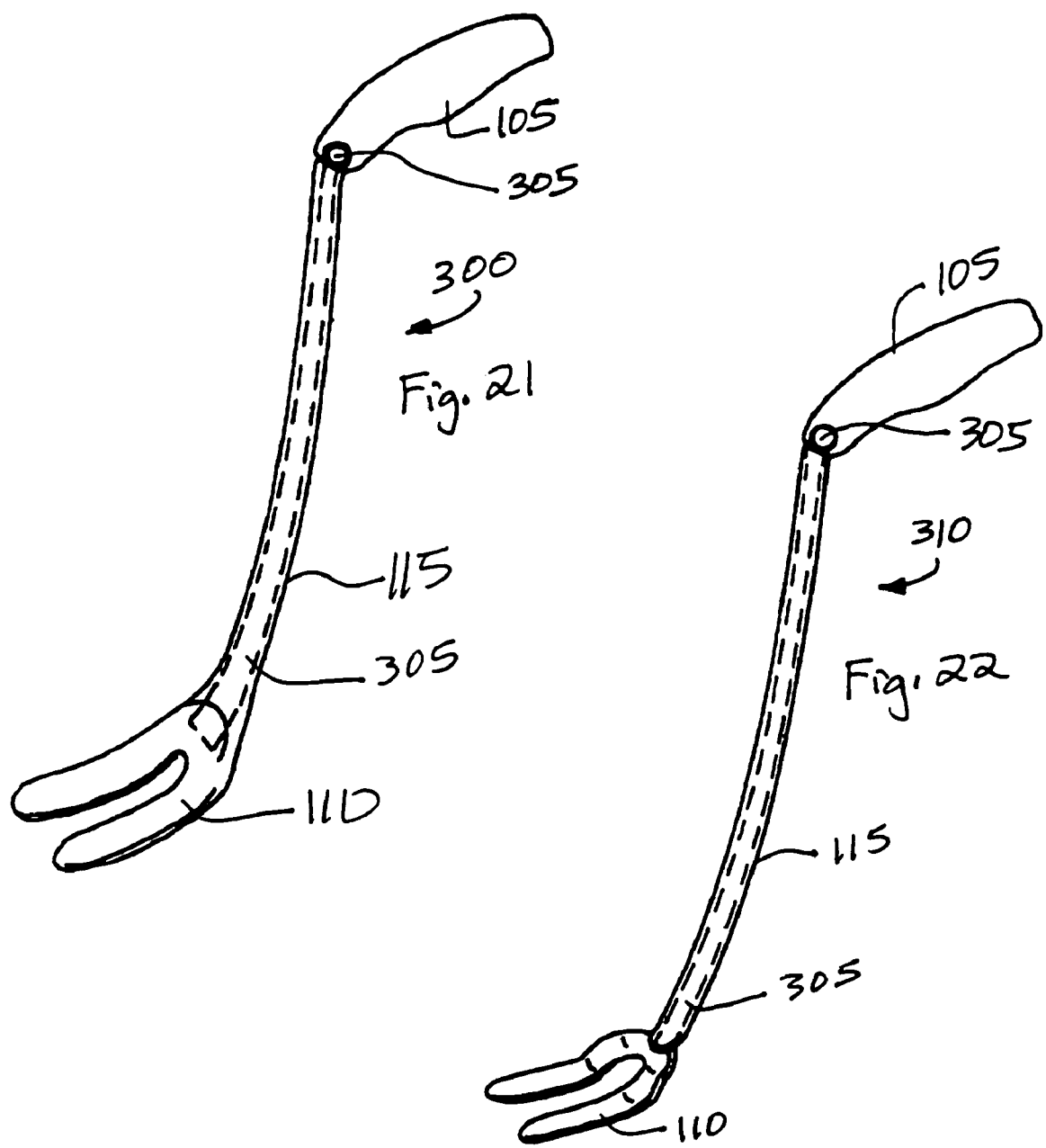

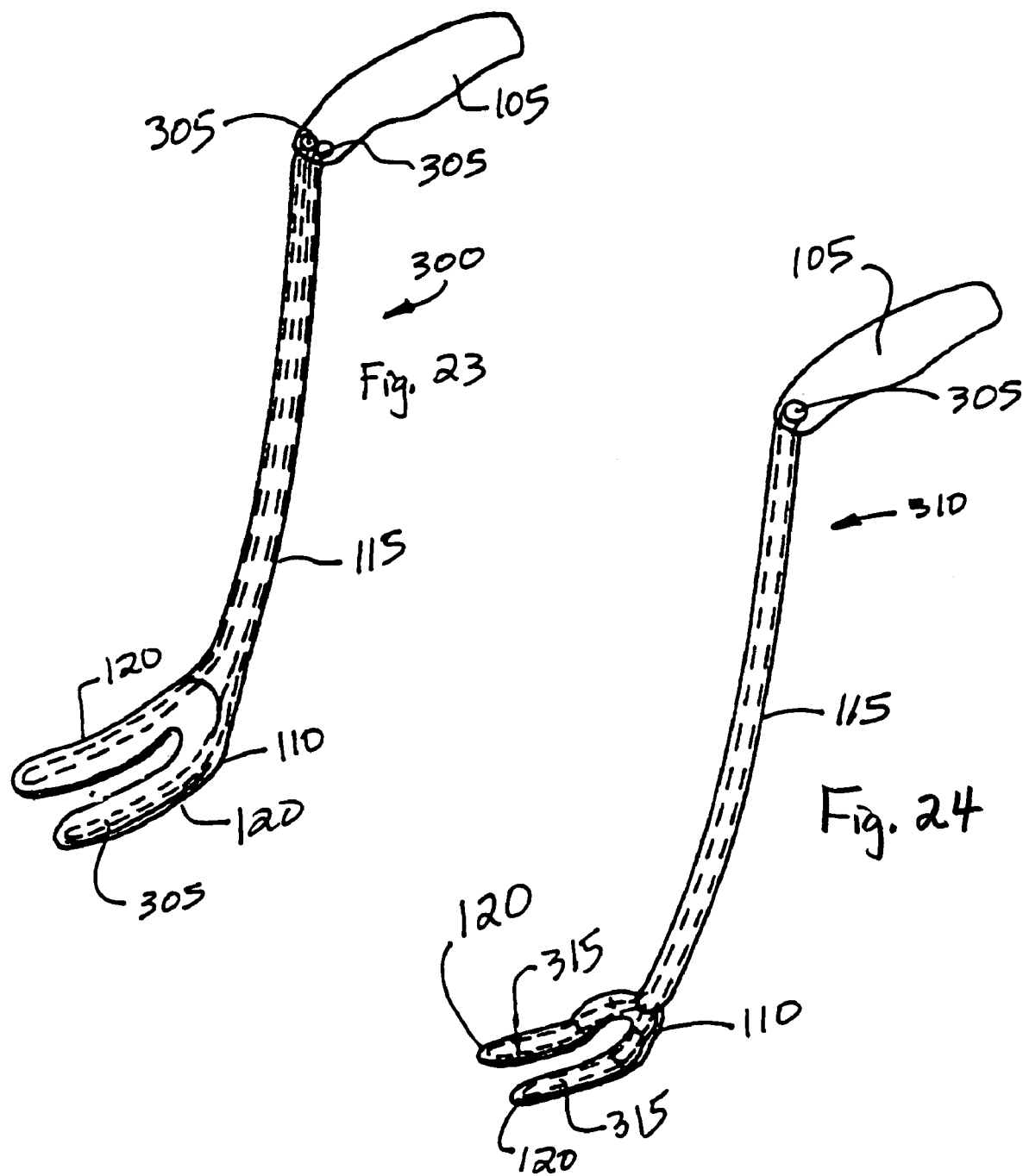

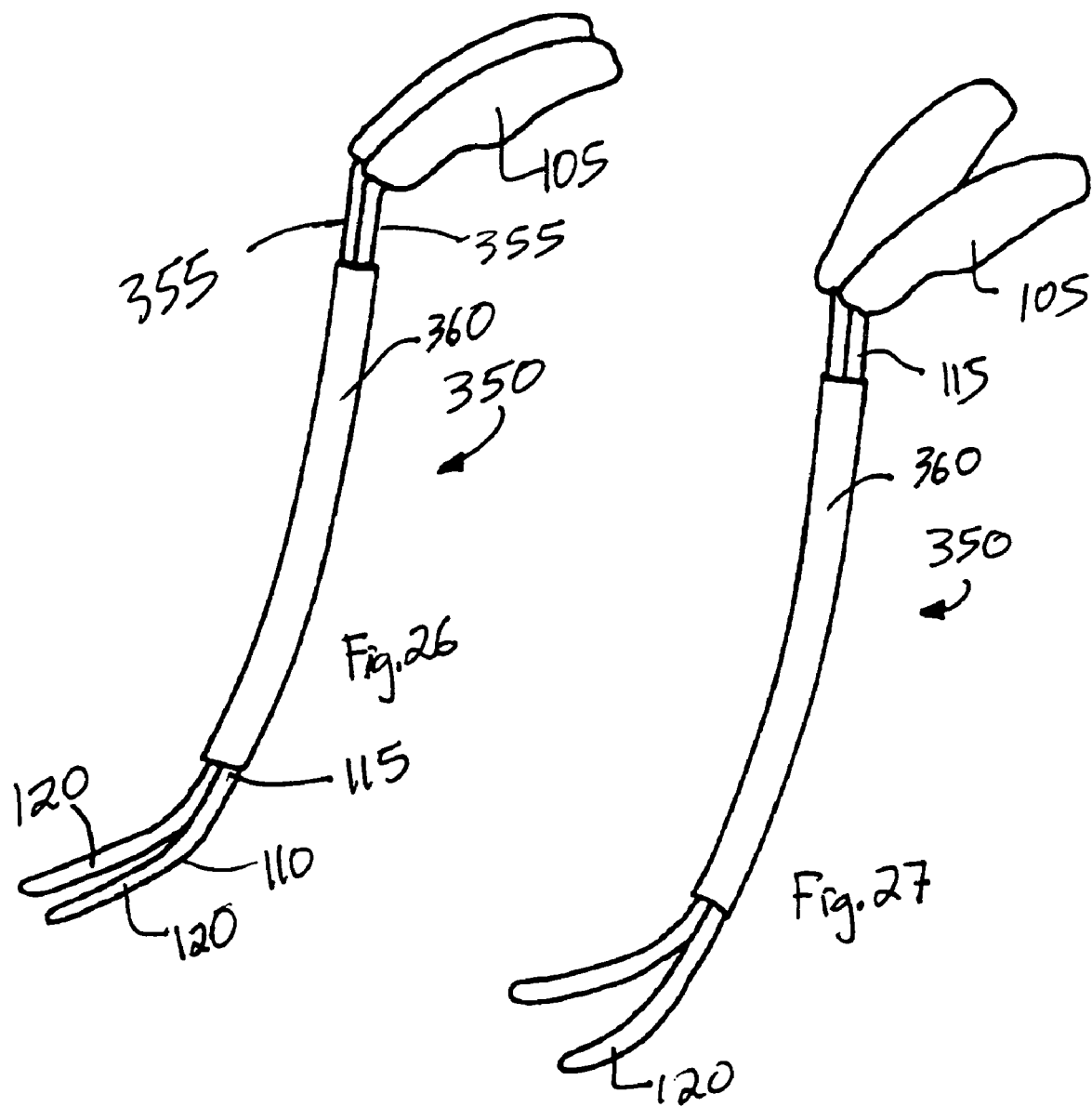

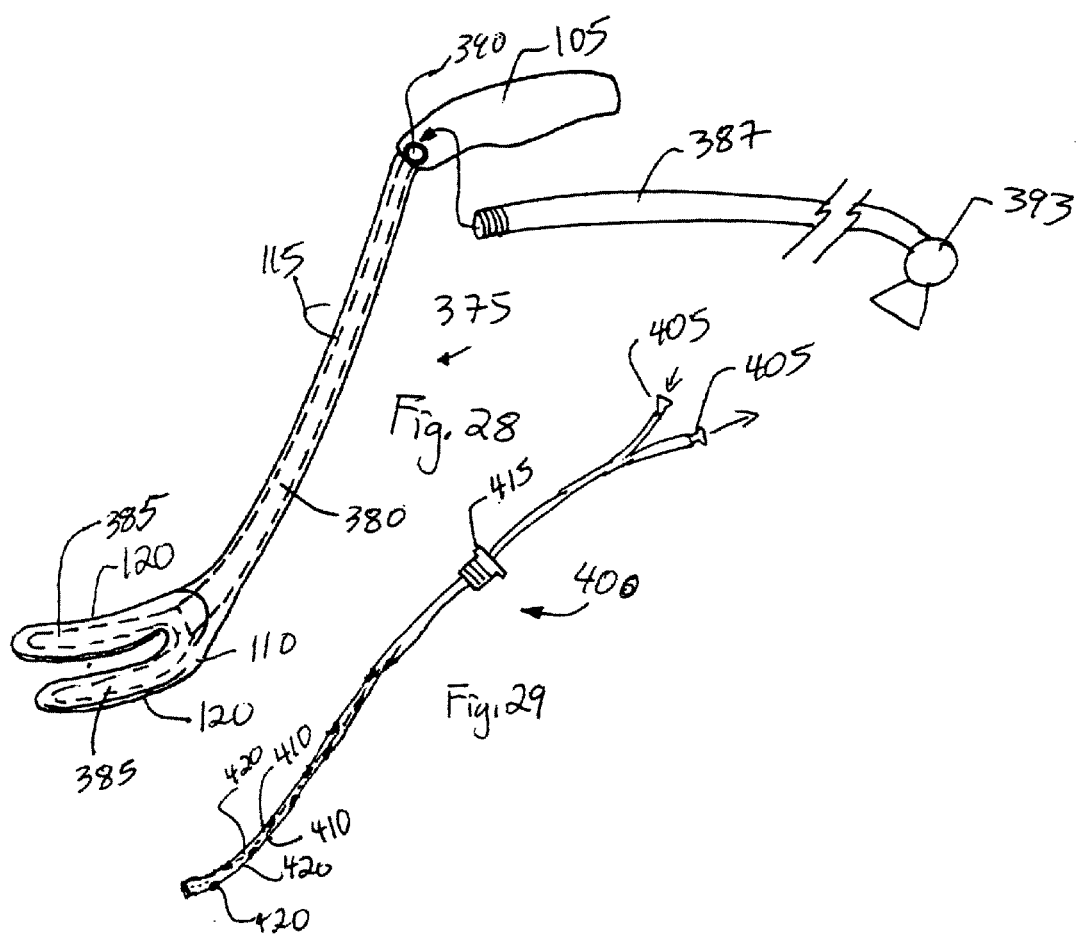

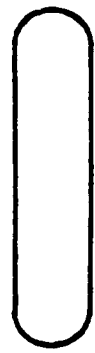  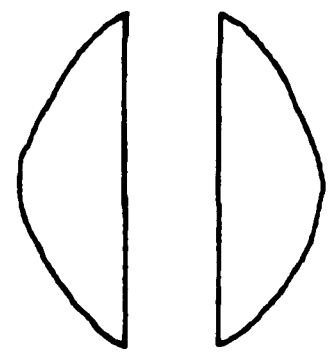 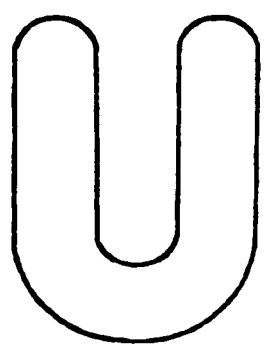
Fig. 32A     Fig. 32B     Fig. 32C
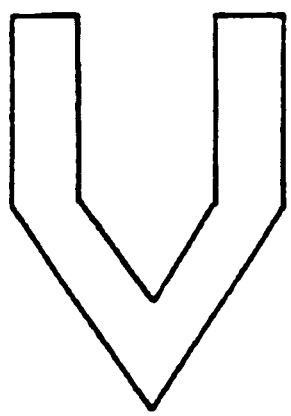 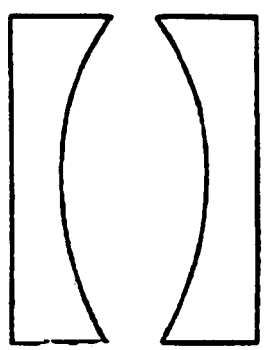
Fig. 32D     Fig. 32E
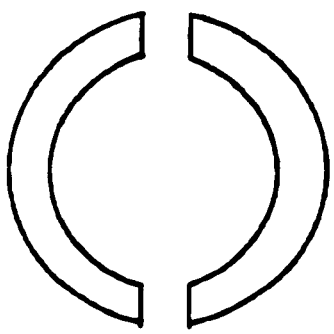 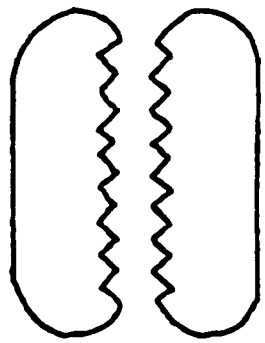 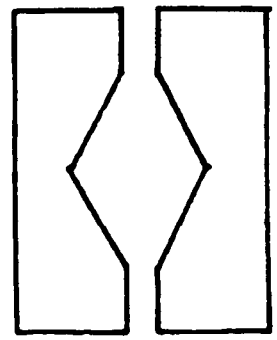
Fig. 32F     Fig. 32G     Fig. 32H

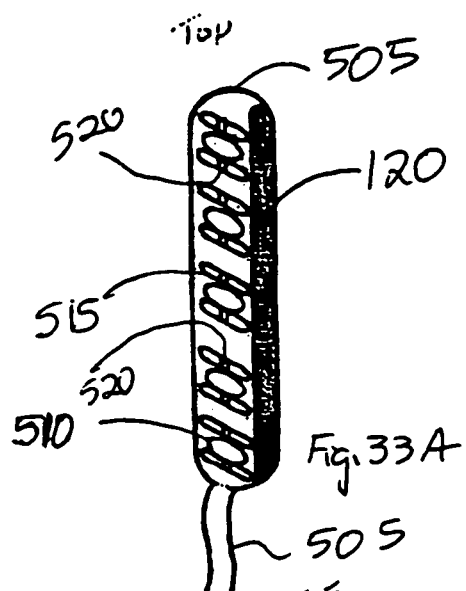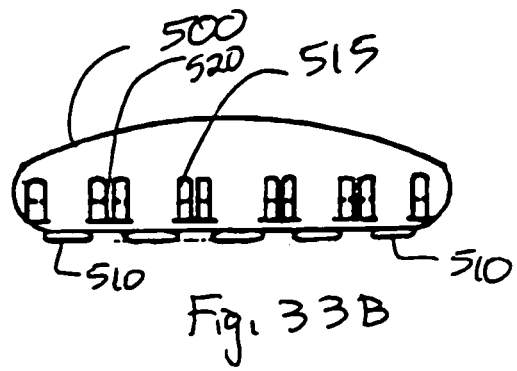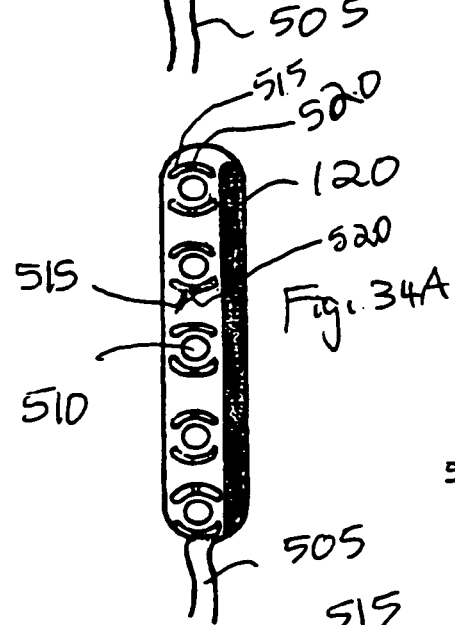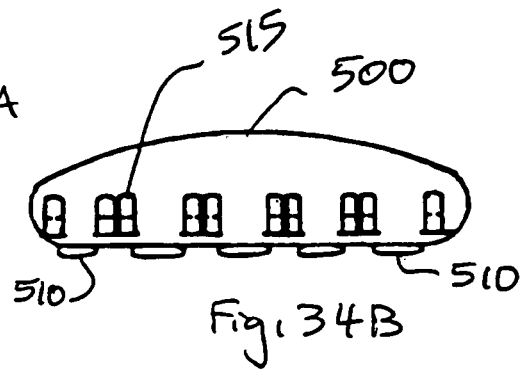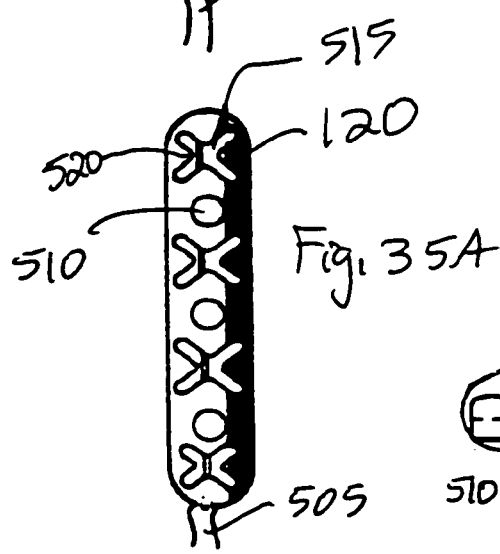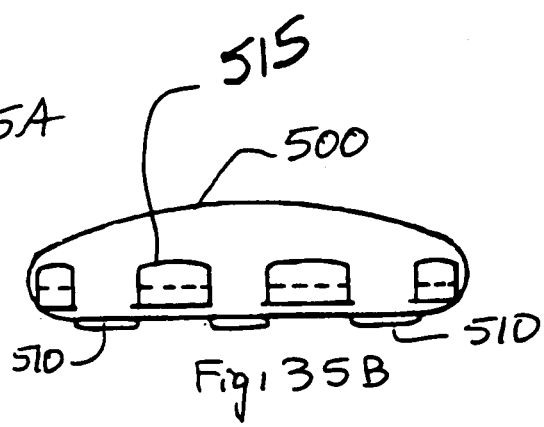

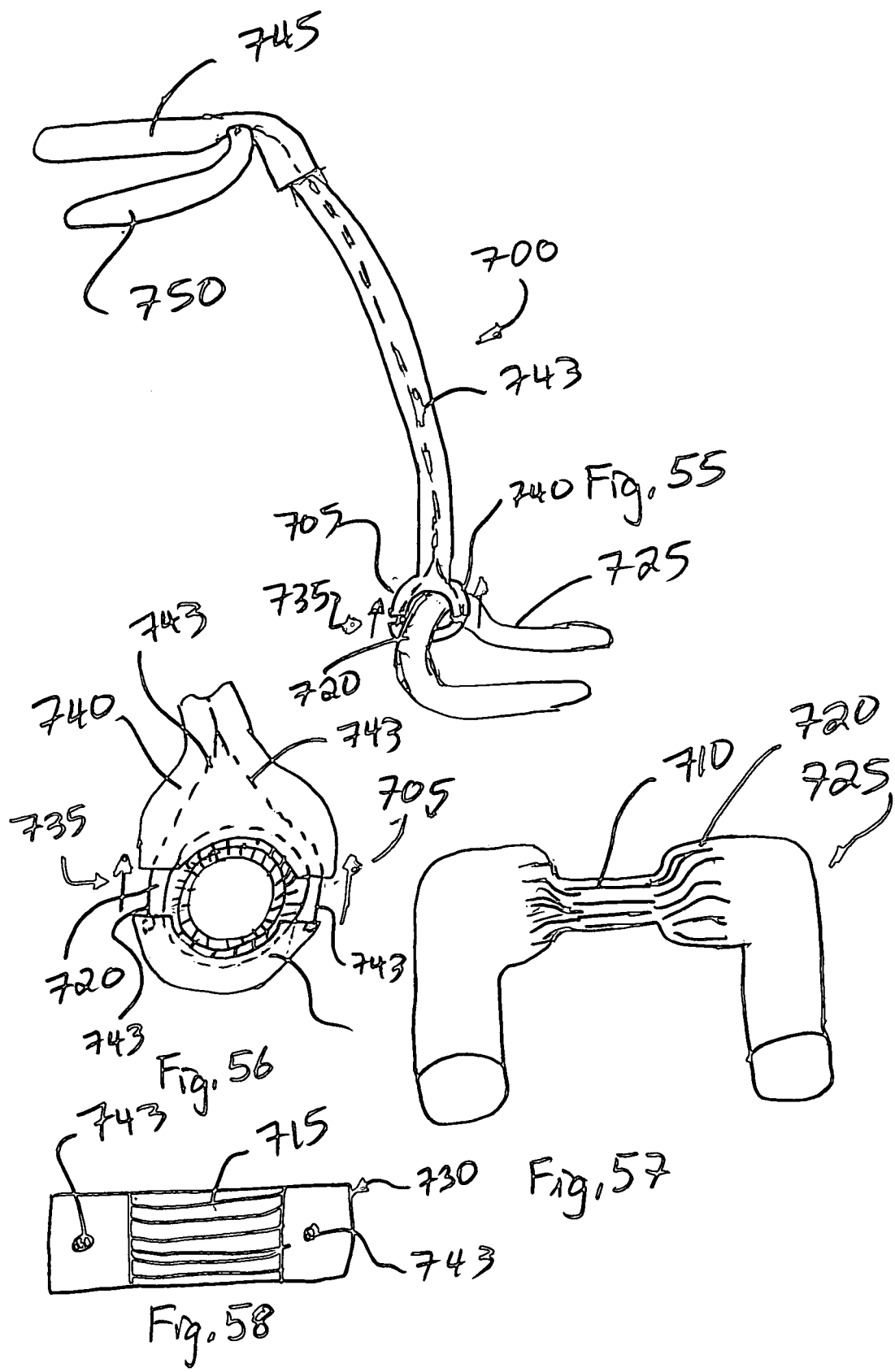

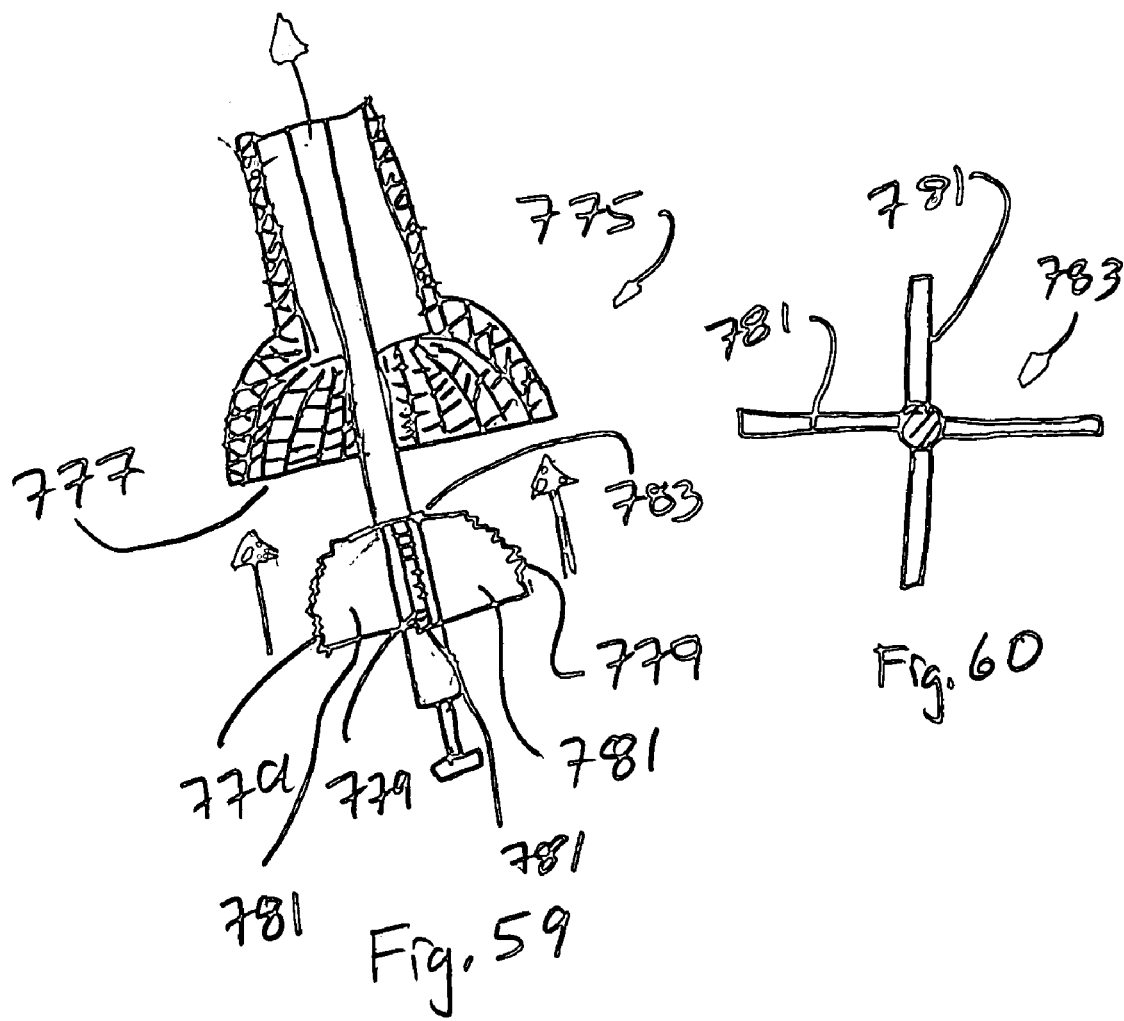
Fig. 59
Fig. 60
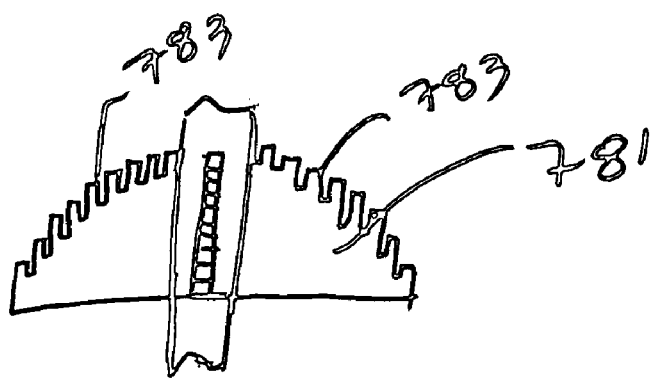
Fig. 61

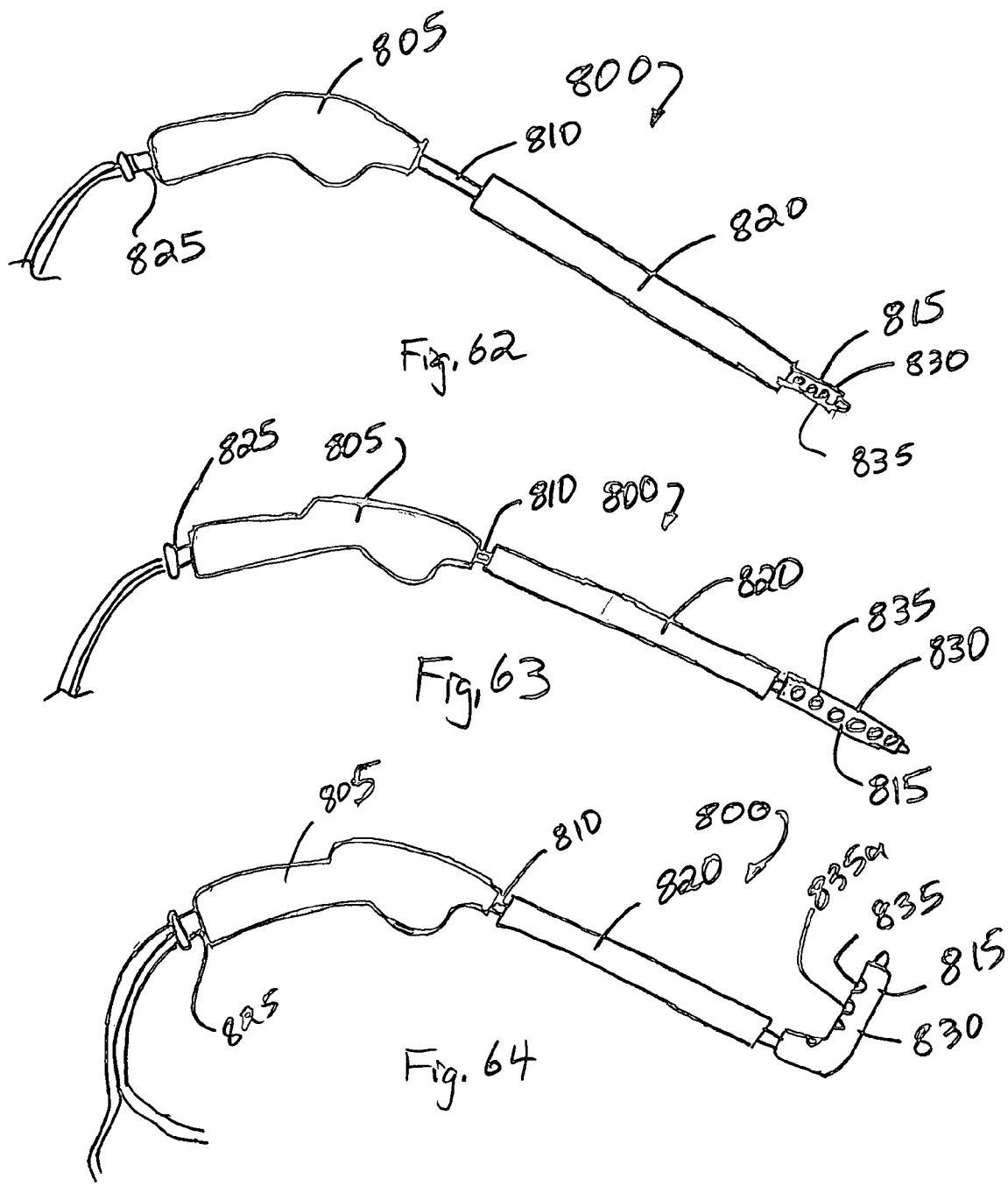

SUPERELASTIC/SHAPE MEMORY TISSUE STABILIZERS AND SURGICAL INSTRUMENTS

RELATED APPLICATIONS

This application claims the benefit of priority under 21 USC § 119(e)(1) of prior U.S. provisional patent application 60/317,182, filed Sep. 6, 2001 and titled Superelastic Tissue Stabilizer.

TECHNICAL FIELD

The technical field of the invention relates to localized tissue stabilization for stabilizing tissue during, for example, a beating heart or off-pump coronary artery bypass grafting (CABG) procedure.

BACKGROUND

It is well-known that diseases of the cardiovascular system affect millions of people each year and are a leading cause of death in the United States and throughout the world. One form of cardiovascular disease is ischemia, in which there is a reduction in the blood supply leading to the heart. This reduction is caused by atherosclerosis or any other condition that creates a restriction in blood flow at a critical point in the cardiovascular system that supplies blood to the heart. For some patients, the blockage or restriction in the blood flow can be surgically treated by coronary artery bypass grafting (CABG), commonly referred to as a "coronary bypass" operation. In this procedure, the surgeon removes a portion of a vein or artery from another part of the body and uses it as a graft to bypass the obstruction and restore circulation to the heart.

The surgeon uses the graft to bypass the obstruction by attaching one end to the ascending aorta and attaching the other end to a coronary artery, distal to the obstruction. The procedure of making these attachments is known as an anastomosis. This can be performed with the heart stopped and the patient put on cardiopulmonary bypass or, during a beating-heart CABG procedure, while the heart muscle is continuing to contract and pump blood. However, in the latter case, the anastomosis is difficult to perform because the heart is moving and pumping blood at the same time that the surgeon is suturing the graft in place.

Importantly, the sutures must be carefully placed so that the graft is firmly attached and does not leak when blood flow through the graft is established. During a beating-heart CABG, it is important that the procedure be performed rapidly because the blood flow through the target coronary artery may be interrupted or reduced during the procedure in order to create the anastomosis without excessive blood loss. Moreover, if the beating heart CABG procedure is performed partially or completely in a minimally invasive manner, the working space and visual access may be limited because the surgeon may be working through a small incision in the chest or may be viewing the procedure on a video monitor if the site of the surgery is viewed via a surgical scope.

SUMMARY

In one general aspect, a surgical instrument is used for temporary use in a medical procedure in a mammalian body. The surgical instrument is configured to be changed between two shapes upon application of one or both of heating and cooling The instrument includes a first member, a second member having a surface configured to contact tissue, and a means to apply heating or cooling to one or both of the first member and the second member to change the shape between a first shape and a second shape.

Embodiments of the surgical instrument may include one or more of the following features. For example, application of cooling causes one or both of the first member and the second member to become malleable. Application of heating causes one or both of the first member and the second member to change shape. The application of heating may include one or both of supplying a heated fluid to one or both of the first member and the second member and receiving in one or both of the first member and the second member the heat generated by the mammalian body. The application of cooling may causes the surface configured to contact tissue to adhere to the tissue.

The surgical instrument may further include a source to apply vacuum to the surgical instrument, the second member including at least one opening passing through the surface configured to contact tissue and the application of vacuum to the surgical instrument adheres the surface configured to contact tissue to the tissue. The surgical instrument also may further include one or more channels in one or both of the first member and the second member. The channels may be designed for one or more of application of vacuum, application of heating, application of cooling, application of a therapeutic agent, application of a second surgical instrument, and application of shaping mandrils. The shaping mandrils impart a shape in, or rigidify, one or both of the first member and the second member.

The second member may include one or more feet, each of the feet including a surface configured to contact tissue. The surface that is configured to contact the tissue may include a removable component for removably attaching to each of the feet.

The first member may be connected to the second member by a pivotal joint that includes a finned surface that pivotally mates with a curved surface. The surgical instrument may further include a handle extending from the first member, the handle including a nonthreaded thumb slide to lock the finned surface against the curved surface to fix the position of the first member relative to the second member.

The surgical instrument may further include a delivery tube, a third member and a fourth member having a surface configured to contact tissue. The second member and the fourth member include feet, each of the feet including the surface configured to contact tissue, and the feet being separately controllable by controlling the movement of the first member and the second member.

The surgical instrument may be one or both of a tissue retractor and a tissue stabilizer. The surgical instrument may be made from a shape memory material, including being made from a shape memory metal such as Nitinol.

In another general aspect, a surgical instrument for temporary use in a medical procedure in a mammalian body to be placed in contact with tissue is configured to be changed between two shapes upon removal of a constraining force. The surgical instrument includes a first member, a second member having a surface configured to contact tissue, and a constraining means to apply a constraining force to one or both of the first member and the second member to cause one or both of the first member and the second member to be in a first constrained shape.

Embodiments of the surgical instrument may include one or more of the following features. For example, the constraining means may be configured to be moved relative to the first member and the second member to remove the constraining force from one or both of the first member and the second member to allow one or both of the first member and the second member to return to an unconstrained shape. One or both of the first member and the second member may be fabricated from a superelastic material, including being made from a superelastic metal such as Nitinol. The surgical instrument may be one or both of a tissue retractor and a tissue stabilizer.

The surgical instrument may further include a source to apply vacuum to the surgical instrument, the second member including at least one opening passing through the surface configured to contact tissue and the application of vacuum to the surgical instrument adheres the surface configured to contact tissue to the tissue. The surgical instrument also may further include one or more channels in one or both of the first member and the second member. The channels may be designed for one or more of application of vacuum, application of heating, application of cooling, application of a therapeutic agent, application of a second surgical instrument, and application of shaping mandrils. The shaping mandrils impart a shape in, or rigidify, one or both of the first member and the second member.

The second member may include one or more feet, each of the feet including a surface configured to contact tissue. The surface that is configured to contact the tissue may include a removable component for removably attaching to each of the feet.

The first member may be connected to the second member by a pivotal joint that includes a finned surface that pivotally mates with a curved surface. The surgical instrument may further include a handle extending from the first member, the handle including a nonthreaded thumb slide to lock the finned surface against the curved surface to fix the position of the first member relative to the second member.

The surgical instrument may further include a delivery tube, a third member and a fourth member having a surface configured to contact tissue. The second member and the fourth member include feet, each of the feet including the surface configured to contact tissue, and the feet being separately controllable by controlling the movement of the first member and the second member.

In another general aspect, a surgical instrument is temporarily used in a medical procedure in a mammalian body. The method of temporarily using the surgical instrument in the medical procedure in the mammalian body includes providing a surgical instrument fabricated from a shape memory material and being configured to be changed between two shapes in the mammalian body upon application of one or both of heating and cooling. The surgical instrument includes a delivery device, a first member, a second member having a surface configured to contact tissue, and a means to apply heating or cooling to one or both of the first member and the second member to change the shape between a first shape and a second shape. The method further includes applying cooling to one or both of the first member and the second member and placing one or both of the first member and the second member into the delivery device in a first shape; advancing the delivery device in the mammalian body; advancing the first member and the second member in the delivery device such that at least one of the first member and the second member extend out of the delivery device into the mammalian body; applying heating to one or both of the first member and the second member to change the shape of one or both of the first member and the second member from the first shape to a second shape; using the second member to contact tissue; and removing the surgical instrument from the mammalian body.

Embodiments of the method may further include one or more of the following features. For example, the surgical instrument may be used in one or more of minimally invasive valve surgery, stabilization of tissue, retracting tissue, delivery of vacuum to tissue, application of heating to tissue, application of cooling to tissue, application of a therapeutic agent, application of a second surgical instrument, and application of shaping mandrils through channels in the first member and/or second member, whereby the mandrils impart a shape in, or rigidify, one or both of the first member and the second member.

The application of cooling may cause one or both of the first member and the second member to become malleable. Application of heating may cause one or both of the first member and the second member to change shape. The application of heating may include one or both of supplying a heated fluid to one or both of the first member and the second member and receiving in one or both of the first member and the second member the heat generated by the mammalian body. The application of cooling may causes the surface configured to contact tissue to adhere to the tissue.

In the method, the surgical instrument may further include a source to apply vacuum to the surgical instrument, the second member including at least one opening passing through the surface configured to contact tissue and the application of vacuum to the surgical instrument adheres the surface configured to contact tissue to the tissue. The surgical instrument also may further include one or more channels in one or both of the first member and the second member. The channels may be designed for one or more of application of vacuum, application of heating, application of cooling, application of a therapeutic agent, application of a second surgical instrument, and application of shaping mandrils. The shaping mandrils impart a shape in, or rigidify, one or both of the first member and the second member.

The second member may include one or more feet, each of the feet including a surface configured to contact tissue. The surface that is configured to contact the tissue may include a removable component for removably attaching to each of the feet.

The first member may be connected to the second member by a pivotal joint that includes a finned surface that pivotally mates with a curved surface. The surgical instrument may further include a handle extending from the first member, the handle including a nonthreaded thumb slide to lock the finned surface against the curved surface to fix the position of the first member relative to the second member. The surgeon may move the thumb slide to fix the position of the first member relative to the second member.

The surgical instrument may further include a delivery tube, a third member and a fourth member having a surface configured to contact tissue. The second member and the fourth member include feet, each of the feet including the surface configured to contact tissue, and the feet being separately controllable by controlling the movement of the first member and the second member.

The surgical instrument may be one or both of a tissue retractor and a tissue stabilizer. The surgical instrument may be made from a shape memory metal such as Nitinol.

In another general aspect, an apparatus for stabilizing tissue includes a handle segment comprising a first material, a stabilizing segment comprising a second material, and an arm segment connecting the handle segment to the stabilizing segment and comprising a third material. At least one of the first material, the second material, and the third material comprise a superelastic material.

In another general aspect, an apparatus for stabilizing tissue includes a handle segment, a stabilizing segment, and an arm segment connecting the handle segment to the stabilizing segment. The stabilizer is formed to have a first shape, coolable to have a second shape, and heatable to regain the first shape.

In another general aspect, an apparatus for stabilizing tissue includes a handle segment, a stabilizing segment including at least one lumen, and an arm segment including at least one lumen. The arm segment connects the handle segment to the stabilizing segment. The stabilizing segment lumen is connected to the arm segment lumen and is configured to received a mandril.

In another general aspect, the inventors have developed a localized tissue stabilizer for use during beating heart surgery, specifically to stabilize the area around the site of the distal coronary anastomosis during a coronary artery bypass graft (CABG) procedure that is minimally invasive, port access, robotically assisted or other type of surgical procedure. The stabilization device may also be used in endoscopic and laparoscopic procedures. The stabilizer, or specific sections of the stabilizer, may be made from a superelastic/shape memory metal alloy (e.g., Nitinol) that allows a section or sections of the stabilizer to be flexed into a reduced profile for insertion through the chest wall. Once through the wall, the stabilizer returns to the desired shape once the constraining forces have been removed. Additionally or alternatively, reinforcing members may be used to rigidify the flexed areas. The stabilizer can also be similarly flexed during withdrawal from the chest cavity. The stabilizer generally utilizes compression, static or active vacuum, combination, or other methods to remain in contact with the heart surface. The tissue stabilizer, as described, or with simple modifications, has additional utility as a heart positioner (e.g., to manipulate the heart position to access side or posterior vessels), as well as a tissue retractor (e.g., for use during minimal access valve surgery).

A localized tissue stabilizer for use during beating heart surgery, specifically to stabilize the area around the site of the distal coronary anastomosis during a coronary artery bypass graft (CABG) minimally invasive, port access, robotically assisted or other types of surgical procedures. The stabilization device may also be used in endoscopic and laparoscopic procedures. The stabilizer, or specific sections of the stabilizer, is made from a superelastic/shape memory metal alloy, such as nitinol, that allows the distal section of the stabilizer to be deformed into a reduced cross section profile for insertion through the chest wall. Once through the wall, the stabilizer returns to the desired shape once the constraining forces have been removed or in the case of shape memory materials, heat causes the stabilizer to return to its annealed configuration. The stabilizer can also be similarly deformed during withdrawal from the chest cavity. The stabilizer utilizes compression, static or active vacuum, cryo, adhesive, protrusions, or combination to remain in contact with the heart or tissue surface.

The stabilizer and stabilizer systems described herein provide considerable advantages. For example, the stabilizer can have a shaft or arm segment with a minimized cross-section for increased surgical field visibility for the surgeon. The stabilizer can be deformable and collapsible for easy insertion and withdrawal through a minimal access or narrow opening. The stabilizer and related devices can be configured with insertable mandrils to modify the shape and/or rigidity of the stabilizer, before, during, or after the device's insertion into a body cavity, such as the thoracic cavity and can be removed to facilitate withdrawal. The stabilizer is designed to be compatible (i.e., mountable) with most commonly available supporting brackets, arms, rails, etc. and cardiothoracic retractors. The stabilizer is designed to provide tissue immobilization or stabilization using a simple vacuum and/or a mechanical means, such as compression. The vacuum can be locally controlled or remotely controlled and incorporated to pass through the inside of the shaft or arm segment, or on the outside of the shaft or arm segment. The stabilizer can be provided with multiple, interchangeable feet and/or contacting surfaces, including single or multiple malleable or spring elements. The stabilizer can be advantageously designed for increased access and visualization of the anastomotic or surgical field or site by using a low profile arm segment and feet and/or contacting surfaces as well as by passing the vacuum or fluid lines, tubes or conduits within the device itself. The stabilizer advantageously can have independent feet and/or contacting surface rotation which provides benefits during procedures of the epicardial surface and other convex tissue or organ surfaces. The stabilizer may be advantageously fabricated completely or partially from a shape memory or superelastic material such that the device deflects the impact of a force or blow, such as the beating of the heart. This transfers force to the device so that it flexes and there is less trauma to the heart, providing atraumatic stabilization. Alternatively, if the shaft is bowed, increased compressive force against the tissue surface is advantageously provided. The device also can include a cooling feature to cool the superelastic or shape memory material, which advantageously provides easy insertion and withdrawal of the device through a confined or narrow opening.

The details of one or more embodiments of the stabilizer are set forth in the accompanying drawings and the description below. Other features and advantages of the stabilizer will be apparent from the description, the drawings, and the claims.

DESCRIPTION OF THE FIGURES

FIG. 3 is a perspective view of a second implementation of a tissue stabilizing apparatus.

FIG. 4 is a perspective view of the tissue stabilizing apparatus of FIG. 3 with a retracted foot section 110.

FIGS. 5 and 6 are perspective views of the tissue stabilizing apparatus of FIG. 3 with the feet sections in the process of expanding from the retracted configuration of FIG. 4 to the configuration of FIG. 3.

FIGS. 7-10 are various implementation of stabilizer segment of the tissue stabilizing apparatus of FIG. 1.

FIGS. 11 and 12 are side and perspective views, respectively, of a handle configuration for use particularly with the tissue stabilizing apparatus of FIG. 10.

FIGS. 13 and 14 are cross-sectional side views of a semicircular arm segment of a tissue stabilizing apparatus in an unrestrained and a restrained configuration, respectively.

FIGS. 15 and 16 are cross-sectional side views of a cross-shaped arm segment of a tissue stabilizing apparatus in an unrestrained and a restrained configuration, respectively.

FIGS. 17 and 18 are perspective views of stabilizers configured with an internal and external, respectively, spraying apparatus terminating in the feet.

FIGS. 19 and 20 are perspective views of the stabilizers of FIGS. 17 and 18 having a spraying apparatus terminating in the transition between the stabilizing segment and the arm segment.

FIGS. 21-24 are perspective views of stabilizers having one or more internal channels configured to receive one or more mandrils.

FIGS. 26 and 27 are perspective views of a stabilizer system using separate stabilizers within a tubular member.

FIG. 28 is a perspective plan view of a stabilizer with an active temperature control system.

FIG. 29 is a perspective side view of a temperature control tube for use with the stabilizer of FIG. 28.

FIGS. 32A-H are profile views of the geometry of feet and/or contacting surfaces.

FIGS. 33A and 33B are sectional bottom and side views of a suction apparatus for the feet and/or contacting surfaces of a stabilizer.

FIGS. 34A and 34B are sectional bottom and side views of a suction apparatus for the feet and/or contacting surfaces of a stabilizer.

FIGS. 35A and 35B are sectional bottom and side views of a suction apparatus for the feet and/or contacting surfaces of a stabilizer.

FIG. 55 is a perspective side view of a stabilizer having a clamp pivot mechanism between the stabilizer segment and the shaft.

FIG. 56 is a cross-section side view of the clamp pivot mechanism.

FIG. 57 is a front view of the stabilizer segment showing ridges.

FIG. 58 is a top view of a lower clamp half of the clamp pivot mechanism showing ridges.

FIG. 59 is a cross-sectional side view of a fin-type pivot mechanism.

FIG. 60 is a bottom view of the fins.

FIG. 61 is a side view of fins using vertical spikes.

FIG. 62 is a side view of a shape memory/superelastic surgical instrument.

FIG. 63 is a side view of the shape memory/superelastic surgical instrument extended from a delivery tube.

FIG. 64 is a side view of the shape memory/superelastic surgical instrument extended from the delivery tube and configured in an unconstrained shape.

DETAILED DESCRIPTION

Figure 1:
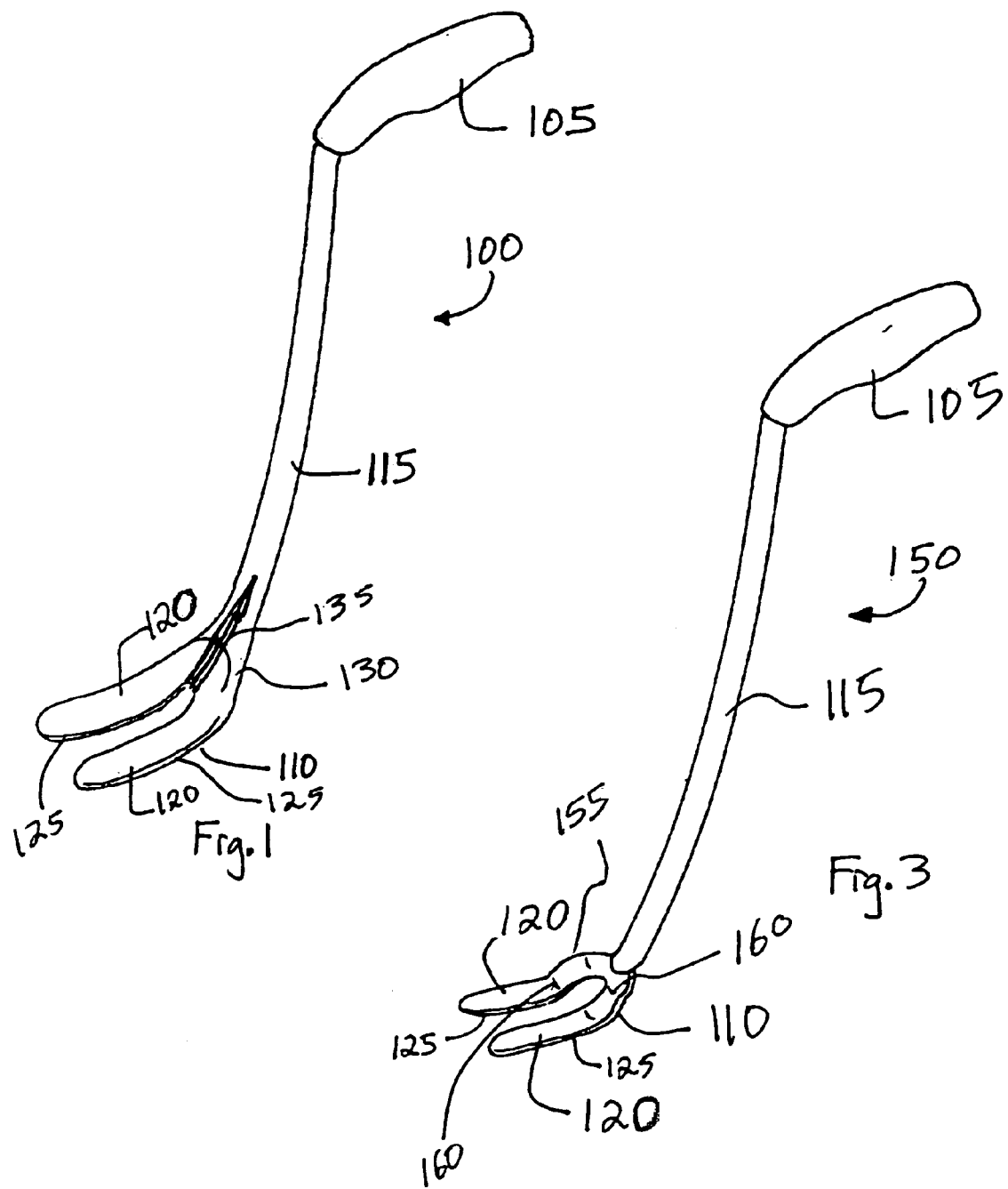
FIG. 1 is a perspective view of a tissue stabilizing apparatus.

Referring to FIG. 1, a stabilizer 100 for stabilizing tissue includes a handle segment 105, a stabilizing segment 110, and an arm segment 115. The arm segment 115 connects the handle segment 105 to the stabilizing segment 110. The apparatus is configured to be used by a surgeon who positions and presses the stabilizing segment 110 against a tissue surface to stabilize the tissue surface for a surgical procedure, and mounts the arm segment to a retractor or an arm or rail that is attached to the retractor or similar apparatus. For example, the apparatus 100 can be used by a cardiac surgeon to stabilize a section of a beating heart to perform a bypass of a coronary artery, by an orthopedic surgeon to stabilize the position of tissue during arthroscopic surgery, or a surgeon during any minimally invasive surgeon of the abdominal region. In any of these procedures, or any similar procedure, the surgeon is able to insert the stabilizer 100 into a confined space within a patient, stabilize tissue, perform the intended surgical procedure, and remove the apparatus without the necessity of opening the surgical region anymore then is necessary. Optionally, the surgeon can insert or deliver the stabilizer 100 through a confined delivery device, such as a round or oval tube. The arm segment of the stabilizer is connected to a conventional retractor arm or rail, as is well known in the art, so that it can be moved into the desired position, and then is secured in that position using a friction, matching geometry, or other connecting device. Such surgical arms or retractors are available from many companies, including Genesee Bio-Medical (Denver, Colo.) and Chase Medical (Richardson, Tex.).

In general, the stabilizer 100 and other stabilizers described herein are made, in part or completely, of a superelastic or shape memory material, such at a nickel titanium alloy (e.g., nitinol). The stabilizer can include the characteristic of the ability to be formed to a first shape, cooled to form a malleable apparatus having a second shape, and heated passively or actively to regain the first shape. Moreover, the material can be resilient so that it can absorb a force by flexing without being permanently deformed. The details of forming the stabilizer are described in greater detail below but, in general, a shape memory or superelastic material is cut and then annealed in a shaping fixture that is placed in a heat source, such as an oven or salt pot, and then cooled in the shaped position to impart the shape to the material.

It is important to understand basic terminology when describing metals with elastic, superelastic, or shape memory behavior. In general, elasticity is the ability of a metal, under a bending load, for example, to deflect (i.e., strain) and not take a permanent "set" when the load (i.e., stress) is removed. Common elastic metals can strain to about two percent before they set. Superelastic metals are unique in that they can withstand up to approximately ten percent strain before taking a set, although this application is not limited to superelastic metals that withstand up to approximately ten percent strain. A superelastic stabilizer will work as well with a material that can be strained more than ten percent or less than ten percent. The ability to withstand strain is attributed to a "stress-induced" phase change within the metal to allow it to withstand such dramatic levels of strain. This is a desirable feature in collapsible tissue stabilizing/tissue retracting devices. Depending on the composition of the metal, the temperature that provides such a phase change can vary. Further, if the metal is "set" at one temperature, and then the temperature is changed, the metal can return to its "unset" shape. Then, upon returning to the previous "set" temperature, the shape changes back. This is a "shape-memory" effect due to the change in temperature changing the phase within the metal. The following explanation of superelasticity and shape memory properties describes these different metal behaviors, along with the compositions of various superelastic and shape memory alloys.

Elasticity. When a metal is loaded (i.e., stressed) and undergoes, for example, bending, it may deflect (i.e., strain) in a "springy" fashion and tend to return to its original shape when the load is removed, or it may tend to "set" and stay in a bent condition. This ability to return to the original shape is a measure of the elasticity or "resilience" of the metal. This ability for a metal to be resilient is desirable where the ability to deflect, but not deform (i.e., set) is important to maintain an applied force. Thus, elasticity is a highly desirable feature for a flexible, collapsible tissue stabilizer, tissue retractor, and/or heart positioner.

Plasticity. If, under a bending load, the metal takes a set, it is said to have plastically (versus elastically) deformed. This is because the imposed stress produced by the bending load has exceeded the "yield strength" (i.e., stress) of the metal. Technically, this level of stress that produces a set, is referred to as the "elastic limit", but is approximately the same value as the yield strength. If the applied load increases past the yield strength of the metal, it produces more plasticity and can eventually break. The higher the yield strength of the metal, the more elastic it is. "Good" elastic metals can accommodate up to about two percent strain prior to taking a set. However, this is not the only factor governing "elasticity".

Modulus. Another factor that determines the ability of a metal to deflect to a given, desired amount, but not take a set, is the "elastic Modulus", or often called the modulus of elasticity. The "modulus" of the metal is an inherent property. Steels, for example, have a relatively high modulus (30 msi) while the more flexible aluminum has a lower modulus of about 10 msi. The modulus for titanium alloys is generally between 12 and 15 msi.

Resilience. Resilience is the overall measure of elasticity or "spring-back ability" of a metal. The ratio of the yield strength divided by the modulus of the metal is the resilience. Although it is one thing for a metal to be resilient, it must also have sufficient strength for the intended service conditions.

Superelastic metals. As discussed above, when a metal is loaded, each increment of load (stress) produces a given increment of deflection (strain) within the metal. The metal remains elastic if the applied load is below the yield stress. However, there is a unique class of metal alloys that behave in an even more elastic manner. These are the superelastic metals, where, for a given applied stress (load) increment, the strain in the metal can reach 5 or 6 percent or more without taking a set. In this type of metals, the overall strain required to produce a set can reach an impressive 10 percent. This phenomenon is related to a phase change within the metal that is induced by the applied stress. This "stress-induced" phase change also can be used to set the metal at one temperature and return the metal to another shape at another temperature. This is known as a "shape-memory" effect, which is discussed below.

The most common superelastic metal is an alloy comprised of approximately equal parts of nickel (Ni) and titanium (Ti), and sold under the trade name of "Nitinol" or "NiTi." By slightly varying the ratios of the nickel and titanium in Nitinol, the stability of the internal phases in the metal can be changed. Basically, there are two phases: an "austenite" phase and a lower-temperature, "martensite" phase. When the metal is in an austenitic phase condition and is stressed, a stress-induced martensite forms, resulting in the super-elasticity. This is reversible, and the original shape returns upon release of the applied stress.

In general, the nickel to titanium ratio in the Nitinol is selected so that the stress-induced martensite forms at the temperature of use, such as ambient temperatures for the devices that are used in ambient conditions. The specific composition can be selected to result in the desired temperature for the formation of the martensite phase (Ms) and the lower temperature (Mf) at which this transformation finishes. Both the Ms and Mf temperatures are below the temperature at which the austenite phase is stable (As and Af). The performance of a tissue stabilizing, tissue positioning, and/or tissue retracting device can be further enhanced with the use of superelastic materials such as Nitinol, that will return to their intended original shape when released within the chest cavity.

Shape Memory Metals. By manipulating the composition of Nitinol, a variety of stress-induced superelastic properties can result. The properties can be tailored to occur over a desired, predetermined service temperature range. This allows the metal to behave in a "shape-memory" or "shape recovery" fashion. In this regard, the metal is "set" to a predetermined, desired shape at one temperature when in a martensitic condition, but which returns to the original shape when the temperature is returned to the austenitic temperature.

The shape memory phenomena occurs from a reversible crystalline phase change between austenite and the lower-temperature martensite. In addition to this transformation occurring from an induced stress as described previously, it can, of course, also change with temperature variations. This transformation is reversible, but the temperatures at which these phase changes start and finish differ depending on whether it is heated or cooled. This difference is referred to as a hysteresis cycle. This cycle is characterized by the four temperatures mentioned previously, As, Af, Ms, and Mf. Upon heating from a lower-temperature martensite, the transformation to austenite begins at the As, and is fully austenite at Af. Upon cooling, austenite begins to transform back to martensite at the Ms temperature, and becomes fully martensitic at the Mf temperature. Again, the specific composition of the alloy can be used to provide a desired combination of these four transformation temperatures.

In the malleable martensitic state, the alloy can be easily deformed (set). Then upon heating back to the austenitic temperature, the alloy freely recovers back to its original shape. Then, if cooled back to the martensitic state, the deformed shape is re-formed. The typical sequence of utilizing this shape memory property is to set the shape of, for example, a tissue stabilizer, while in the higher-temperature austenitic state. Then, when cooled, deform the martensite material, and then heat to recover the original shape.

These materials also can be used to form very tight bends. With the background given above, it can be seen that if a device or component constructed from Nitinol requires an exceptionally tight bend that would normally exceed the elastic limit of the material and thus permanently deform it, a bend can be placed in the device and the device annealed to relieve bending stresses within the device. Following this first bend, the device can be bent further to produce an even sharper bend, and then re-annealed to alleviate the stress from this additional bending. This process can be repeated to attain the desired, sharp bend or radius that would otherwise permanently deform the device if the bend were attempted in a single bending event. The process for recovery from the position of the most recent bend is then performed as described above.

This shape memory ability is very advantageous for devices including, tissue stabilizers, tissue retractors, heart positioners, etc. These devices can be deformed and maintained in their martensitic state (e.g., can use a cooling agent if Mf is below room temperature) until they are introduced and released in the body. Then, a warm, sterile solution, short electrical activation, or other suitable means (free recovery if Af is less than 37° C.) can be applied to trigger the recovery of the predetermined shape. In some implementations, the material remains austenitic after cooling to body temperature. This is achieved by choosing an alloy composition with a hysteresis such that Ms is never reached upon cooling to normal operating conditions (i.e., Ms below body temperature). High-temperature martensite shape memory alloys are also an alternative composition for these implementations.

Although Nitinol is the most popular of the superelastic metals, there are other alloys that exhibit superelastic or shape-memory behavior. These include the following:
  Copper-40 at % Zinc
  Copper-14 wt % Aluminum-4 wt % Nickel
  Iron-32 wt % Manganese-6 wt % Silicon
  Gold-5 to 50 at % Cadmium
  Nickel-36 to 38 at % Aluminum
  Iron-25 at % Platinum
  Titanium-40 at % Nickel-10 at % Copper
  Manganese-5 to 35 at % Copper
  Titanium-49 to 51 at % Nickel (Nitinol)

In summary, there are various ways of characterizing elasticity, but a useful criteria is the ability of the metal to return to its initial, pre-loaded shape. Some metals can only deflect a few percent and remain elastic while others, such as superelastic Nitinol, can deflect up to approximately ten percent. Nitinol offers other advantages because it also is biocompatible and corrosion resistant. This unique combination of properties allows a device made of Nitinol, such as a tissue stabilizer, tissue retractor and/or heart positioner, to be deflected during insertion through the chest wall and return to the form of its intended service (i.e., annealed) shape.

Referring again to FIG. 1, the handle segment is configured for a surgeon to easily grasp and position the stabilizer during a surgical procedure. For example, the handle segment 100 may include an inner material, such as a metal or a plastic, and an outer material, such as a metal or a plastic. For example, the inner material can be a plastic that has been injection molded or machined to have an ergonomic shape. The outer material can be a low durometer plastic against which the surgeon's glove is unlikely to slip or slide, and which can be coated, over molded, or injection molded around the inner material with or without texture to provide additional resistance to slippage.

The arm segment 115 is configured to have a low profile and, for example, be passed through a tube. The arm segment can be made of any biocompatible material, such as a metal or a plastic. A metal arm segment can be integrally formed with a metal handle segment or can be separately attached to a metal or a plastic handle segment. Similarly, a plastic arm segment can be integrally formed with a plastic handle segment or can be separately attached to a plastic or a metal handle segment. The arm segment 115 can be shaped to have a minimal profile and yet retain a certain amount of rigidity.

The stabilizing segment 110 can be formed integrally with the arm segment 115, as illustrated in FIG. 1, or formed separately and then attached to the arm segment. In general, the stabilizing segment 110 includes one foot, two feet, or more than two feet 120. The feet 120 are placed in contact with the tissue to be stabilized or otherwise immobilized. As described in more detail below, a lower surface of the feet can be coated with a contacting section 125. As described in more detail below, the contacting section can be configured to provide an atraumatic surface to contact tissue; a non-slip surface to reduce or prevent movement of the feet 120 when in contact with the tissue surface; a member to apply vacuum, a mist or stream of a fluid to a tissue surface; and/or a continuous or intermittent inflated surface against the tissue. The interface between the stabilizing segment 110 and the arm segment 115 optionally includes a gradual transition segment 130 and a weakened segment 135. The transition segment 130 is configured such that the stabilizer 100 can be withdrawn through a tube or a confining member (not shown) with a confined volume such the transition segment will cause the feet 120 of a superelastic material to be folded together by gradually accepting the frictional pressure caused by the interaction of the stabilizer as it is pulled through the tube. The optional weakened segment 135 can be in the form of a removed section of material placed such that the weakened segment will cause bending or collapsing at its location. As illustrated in FIG. 1, the weakened segment is in the form of a slot cut into or formed with the stabilizer 100. The weakened segment 135 causes the feet 120 to collapse in towards each other when under friction or an inward pressure. The weakened segment can be formed anywhere on the stabilizer in which bending or collapsing is desired.

Figure 2:
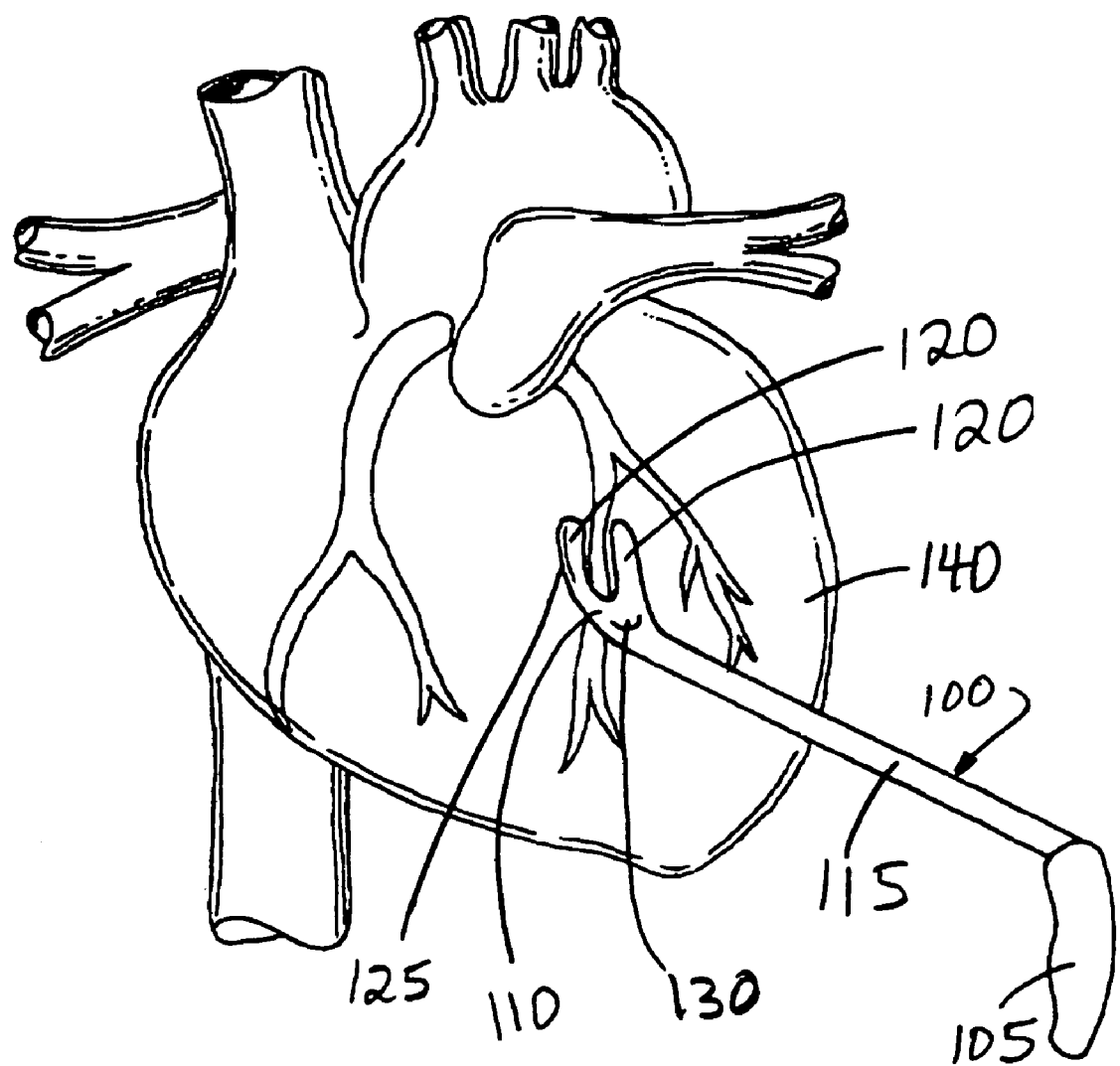
FIG. 2 is a perspective view of the tissue stabilizing apparatus of FIG. 1 being used to stabilize tissue.

The surgeon uses the stabilizer 100 to stabilize or otherwise immobilize a portion of tissue. For example, as illustrated in FIG. 2, the surgeon can use the stabilizer to stabilize cardiac tissue 140 (i.e., a heart) during beating heart coronary artery bypass grafting surgery. In this procedure, the surgeon grasps the handle 105 and positions the stabilizing section 110 against the cardiac tissue 140 such that the pair of feet 120 and/or contacting section 125 are placed on opposite sides of the coronary artery. Although the weakened segment 135 is not illustrated in FIG. 2, it, of course, may be incorporated within this implementation of the stabilizer.

Referring to FIG. 3, in a second embodiment of a stabilizer apparatus, a stabilizer 150 includes the handle 105, the stabilizer section 110, the arm section 115, and the individual feet 120. The stabilizer 150 optionally includes the contacting sections 125. The feet 120 are formed with an elevated segment 155 that elevates the transition between the feet 120 and the arm segment 115. The elevated segment 155 provides considerable advantages in procedures such as coronary artery bypass surgery, as illustrated in FIG. 2, because the stabilizer section 110 can be placed against cardiac tissue adjacent to a coronary artery without compressing the vessel and restricting the blood flow of the coronary artery. The elevated segment 155 includes bent segments 160 with tapered bends to provide atraumatic surfaces that prevent damaging the tissue against which the stabilizer is applied.

Although the stabilizer 150 may be introduced by a surgeon into a body cavity through a conventional open field, it also may be inserted into a body cavity through a narrow opening, such as a narrow incision, in between the ribs, a tube, and/or a confining member. To ease introduction through a narrow opening, the stabilizing segment 110 can be retracted and/or folded together in a collapsed configuration, as illustrated in FIGS. 4 and 5. In particular, FIG. 4 illustrates the feet 120 completely bent back and generally parallel with the arm segment 115. In this configuration, the combination of the arm segment 115 and the feet 120 have a very narrow profile such that the surgeon can introduce the device through a very narrow opening. Moreover, the feet 120 can be bent back or forward and generally curved across its width along the length to have a minimal cross-sectional profile. In FIG. 5, the feet 120 are shown part way through the process of expanding away from the arm segment 115. FIG. 6 illustrates the feet 120 being further along in the process of expanding away from the arm segment, although not completely yet expanded to its final configuration, as illustrated in FIG. 3.

FIGS. 7-10 illustrate additional implementation of the stabilizer segment 110. For example, FIG. 7 illustrates a stabilizer 175 with the elevated segment 155 being configured to provide extra clearance from the tissue, which is especially advantageous in coronary artery bypass surgery to prevent occlusion of a coronary artery. In this implementation, the contacting surfaces 125 are overmolded or adhered to the lower surface of the feet 120 using adhesive, mechanical interference fit, a combination of these, or other means, although they can be formed completely around the outer circumference and surface of the feet 120. The contacting surfaces 125 may be made of, for example, silicone, polyurethane, combination of these, or other materials, or other biocompatible plastic available in low durometers and capable of creating a slip-resistant surface. As described in additional detail below, the outer or lower surface of the contacting surfaces 125 can be formed with a surface configuration or texture to further enhance the slip-resistance of the contacting surfaces. The feet 120 of FIG. 7 generally are formed integrally with the arm segment 115, although the can be separately formed and later attached to the arm segment.

FIG. 8 illustrates a stabilizer 185 having feet 120 that are overmolded with contacting surfaces 125. The contacting surfaces also may be separately formed and then slipped over the feet 120. For example, the feet 120 may have a first outer diameter segment 190 and a second outer diameter segment 195, with the first outer diameter segment having a greater diameter than that of the second diameter segment, and the contacting surfaces 125 can be in the form of a tube having an inner diameter that is very close to the diameter of the second diameter segment. In this manner the contacting surface can be slid over the second diameter segment 195 and held in place by an optional friction fit or with the use of an adhesive, combination or other.

In addition, the feet 120 can be separately formed and attached to mounting surfaces 200 on the arm segment 115. The feet can be attached using welding, soldering, adhering with an adhesive, a press fit interface, a threaded attachment, or any other known attachment means suitable for application to a medical device. In the configuration of FIG. 8, as well as the other configurations shown herein, the feet 120 can be configured for insertion into a narrow opening by retracting backwardly one foot 120 and extending forwardly the other foot 120.

Referring to FIG. 9, a stabilizer 210 is formed with the stabilizer segment 110 being integral with the arm segment 115. In this implementation, a round, oval, flat, or otherwise shaped shaft is cut along its length, generally along its central longitudinal axis. The cut can be formed using any known conventional cutting method, including a laser, a cutting saw, chemical etching, electron discharge machining (EDM), stamping, photolithographic techniques, water jet, and/or any combination of these methods. The opposing sides of the cut then are forced outwardly to form an opening 213. The cut can be made through the distal end 215 of the shaft or can stop short of the distal end, as illustrated in FIG. 9. The stabilizer 210 then is formed by shaping the shaft and attaching the handle segment 105. Optionally, the distal end 215 can be elevated to prevent occlusion of a coronary artery if the stabilizer 210 is to be used in coronary artery bypass procedures. In a derivative implementation, multiple incisions may be made along the length of the shaft. For example, one central incision may be made along the length and extend through the distal end 215 and two incisions may be made in the thus formed opposing segments of the shaft, although not completely through their distal ends. Those two incisions then may be forced apart to form a pair of stabilizing segments, each of which being similar to the stabilizing segment illustrated in FIG. 9.

Referring to FIG. 10, a stabilizer 220 is formed from a single piece of flat material, such as a metal, using any of the known conventional methods of cutting, shaping, bending, forging, and otherwise forming metal. For example, using a flat metal sheet, the stabilizer 210 can be cut by a laser, a cutting saw, chemical etching, electron discharge machining (EDM), stamping, photolithographic techniques, water jet, and/or any combination of these methods. As described below, the cut piece then can be processed to form the three-dimensional shape illustrated in FIG. 9, and a handle attached. Of course, the handle can be formed integrally with the stabilizer 210 from the flat metal sheet and have an ergonomic configuration, as illustrated in FIGS. 11 and 12. The handle segment 105 can be configured to include a first portion 225 and a generally parallel second portion 230. The first portion 225 is curved for easy gripping by the surgeon and provides region to provide a snug fit of the fingers against the second portion 230. In this configuration, the handle segment 105 can be fabricated from a superelastic material, such as Nitinol, or other material.

Moreover, referring to FIGS. 13-16, the arm segment 115 can be fabricated from a superelastic material, such as a superelastic shape memory metal or plastic, have a semicircular profile (FIG. 13) when unrestrained, and have a reduced diameter, low profile shape when restrained (FIG. 14). In another implementation, the arm segment can have a cross-shaped profile (FIG. 15) when unrestrained, and have a reduced diameter low profile, rounded shape when restrained (FIG. 16), for example, during delivery into a narrow opening into a body region.

Referring to FIGS. 17 and 18, the stabilizing apparatus can be configured as a stabilizer 250 that includes an internal misting or spraying capability or attachment 255 (FIG. 17) or as a stabilizer 260 that includes an external misting or spraying capability or attachment 265 (FIG. 18). The misting can be partially or fully atomized and be a diffuse, broad or focused mist, combination of these, or adjustable. The internal spraying attachment 255 includes a tube 270, such as a polymer tube, that passes through channels in the handle segment 105, the arm segment 115, and terminating within or on top of the outer surface of one or both of the feet 120. The distal end of the spraying attachment 265 can include one or more openings 275 through which a fluid, such as saline, or a gas, such as $CO_2$, or other fluid or gas can be continuously or intermittently sprayed, for example, to maintain a clear surgical field during the procedure. The tube 270 can be connected to a syringe to manually inject the fluid, to a pump to automatically dispense the fluid, or a container of fluid to that uses gravity to dispense the fluid, gas or other to the tissue. Alternatively, as illustrated in FIG. 18, the tube 270 can be attached, using known conventional attachment means, such as by using a Luer fitting to the outside of the handle segment 105, the arm segment 115, and/or the feet 120. Attaching the tube 270 to the outside of the stabilizer is believed to reduce the cost of producing the stabilizer.

Referring to FIGS. 19 and 20, the stabilizers 250 and 260 can be configured such that the tubes 270 terminate in one or more openings 280 at the transition between the stabilizing segment 110 and the arm segment 115. A fluid or gas as described above then can be dispensed through the opening(s) 280 onto the surgical field.

Although the stabilizer 250 is illustrated as having the tube inserted through the handle segment and arm segment, the stabilizer can be configured to have an internal channel that terminates in openings in the feet or at the transition between the stabilizer segment and the arm segment. The tube 270 can be threadably or otherwise attached to the handle and fluid dispensed into the channel and out of the openings. For example, the tube 270 can be attached using a Luer fitting or other common fitting or connector.

FIGS. 21-24 illustrate stabilizers having channels configured to receive shaping or reinforcing mandrils. In general, after the stabilizer is inserted into a confined body region, such as the thoracic cavity, the mandrils are inserted into the channels to modify the shape of the stabilizer and/or increase the rigidity of the stabilizer. For example, referring specifically to FIG. 21, the arm segment 115 of a stabilizer 300 includes a channel 305 that passes from approximately the handle segment to the transition region between the stabilizing segment 110 and the arm segment. A mandril (not shown) can be configured to fit loosely or tightly within the channel 305 and when it is inserted into the channel 305 the stabilizer's shape can conform to the shape of the mandril. Additionally, the mandril provides increased rigidity to the stabilizer 300. To vary the rigidity of the stabilizer 300, mandrils of different rigidities, created by varying the material or diameter of the mandril, can be inserted into the channel 305. As shown in the stabilizer 310 illustrated in FIG. 22, the channel 305 can extend from the handle segment 105 to the end of the arm segment 115. The mandrils also may be connected to the arm, rail, or retractor for ensuring that the mandrils are kept in position within the stabilizer.

The mandrils may be made from superelastic/shape memory materials, such as metal alloys (e.g., nitinol); polymers; composites; spring alloys such as Inconel™, and Elgiloy™; malleable material, such as stainless steel, polymers, or other known materials. The geometric characteristics, such as diameter, cross-sectional profile, thickness or any combination of these can be varied to affect the rigidity, flexibility of other physical characteristics of the mandril, and thus the stabilizer. For example, the cross-sectional profile can be shaped like an X, T, Y, concentric, eccentric, and/or tubular. The X, T, and Y shapes allow a fluid to be passed around the mandril. The mandrils may be mounted in position in the stabilizer using a variety of mounting and/or attachment devices, as are well-known in the art, including an annular friction seal, a locking geometry, threaded valve seal connector such as hemostatic valve, a clip that mounts to the handle and the mandril, and/or a combination of these. For example, a fitting with a rotatable end cap may be rotated to compress a circular valve material, such as silicone, around the mandril to lock the mandril in position.

Referring specifically to FIG. 23, the stabilizer 300 can be configured to include multiple channels 305 that pass from the handle segment 105, through the arm segment 115, and terminate in the feet 120. In this configuration, a mandril can be inserted completely or partially into each channel 305 as desired to provide a desired configuration or rigidity.

As illustrated in FIG. 24, the stabilizer 310 can be configured to include the single channel 305 that passes through the arm segment 115 and then splits into multiple channels 315. Rigidity and shape is imparted in the stabilizer 310 by a mandril that includes a distal end having a pair of shaped extensions that fit within the channels 315.

Figure 25:
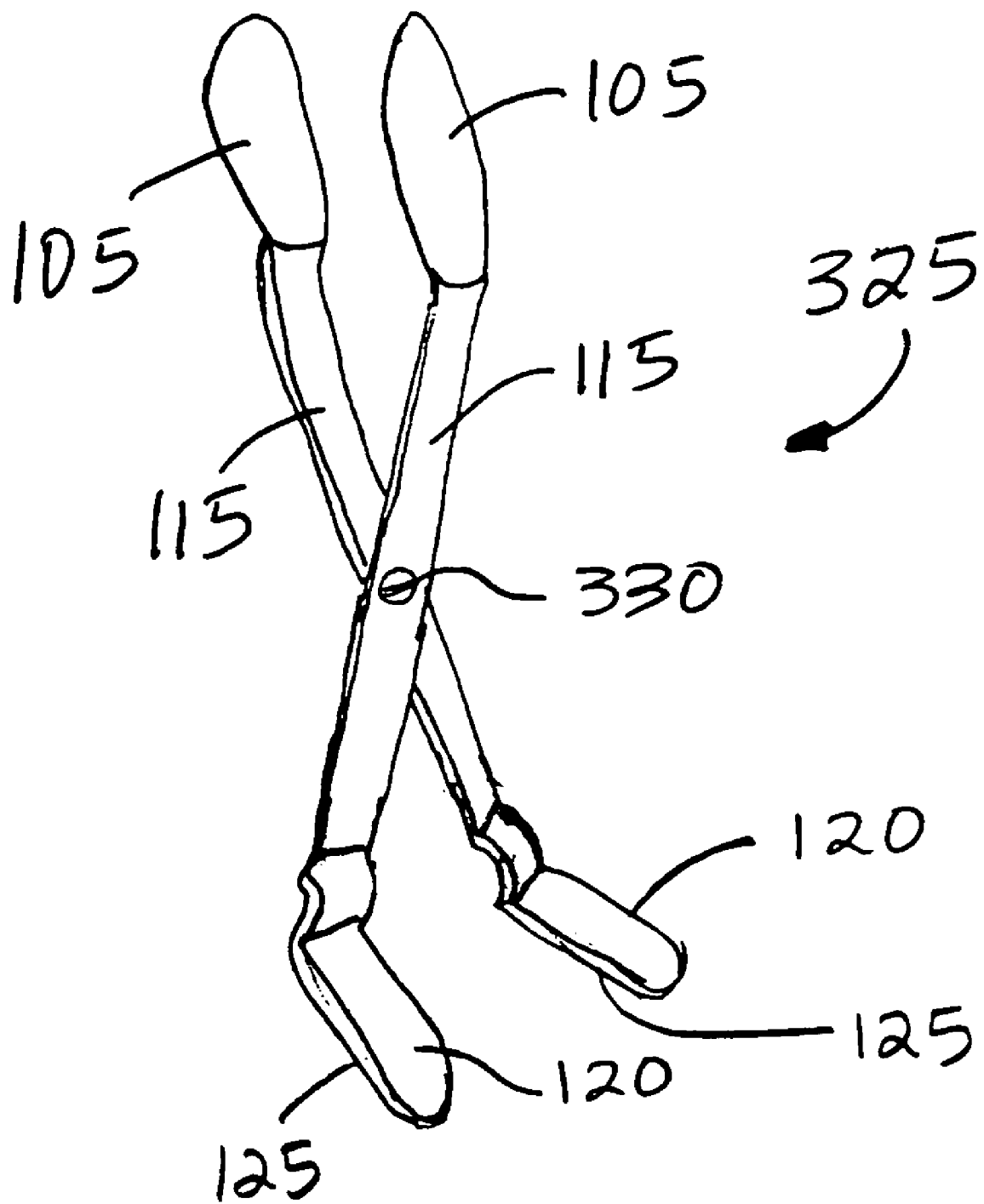
FIG. 25 is a perspective view of a stabilizer in a scissored configuration.

Referring to FIG. 25, a stabilizer 325 can be configured as a pair of scissored feet 120 that are connected through a hinge or screw 330 between the pair of arm segments 115. By fabricating the stabilizer 325 from a shape memory/ superelastic material, the stabilizer can be inserted in a first, narrow profile through a narrow opening and then allowed to expand to a second, wider profile in which the feet 120 are substantially or partially perpendicular to the arm segments 115 so that the surgeon can manipulate and press the feet against a tissue surface. Although the stabilizer 325 is illustrated as including feet 120 for stabilizing or otherwise immobilizing tissue, the feet 120 can be replaced with angled blades for cutting, angled tissue graspers for grasping and holding tissue, or any other surgical tool that benefits from the ability to be inserted in a first, narrow profile and then allowed to expand to a second, wider and/or larger profile.

Referring to FIGS. 26 and 27, the stabilizer apparatus can be implemented as a stabilizer system 350 that includes a pair of independent stabilizers 355 that are passed through a tubular member 360. Each stabilizer 355 includes the handle 105, the arm segment 115, and the stabilizing segment 110. In the configuration of FIGS. 26 and 27, the stabilizing segment includes a single foot 120. The surgeon can insert the system 350 into a narrow opening by first pulling the stabilizers back such that the feet 120 are completely withdrawn into the tubular member 360. With the tubular member positioned within the body cavity, the surgeon advances the stabilizers 355, separately or together, until the feet 120 are extended. The surgeon can independently manipulate the handles 105 to select a position of the feet 120 that allows the surgeon to stabilize the tissue. Although FIGS. 26 and 27 show simplified implementations of the feet 110, the feet can be implemented in a more complex configuration with the curves and bends illustrated in the feet described herein.

The center-to-center distance between the feet can be manipulated by moving the parallel arm segments 115 apart, creating a "V" shape. Additionally, a snap on spacer component may be positioned in between the two arm segments, at a proximal or middle position, or slid down towards the distal end of the arm segment, resulting in the same space separation at the feet. Also, a thumb wheel type device (e.g., similar to that on a drafter's compass) may be used to manipulate the center-to-center width of the feet.

Referring to FIG. 28, a stabilizer 375 can be configured to be cooled and/or heated as necessary for affecting the rigidity of the stabilizer, inserting and removing the stabilizer from a narrow opening, or to provide therapeutic benefit to the tissue against which the stabilizer is placed or in its general vicinity. Moreover, heating and cooling can be used to provide a preventative effect or utility, such as during cooling of tissue during ischemic periods of CABG procedures. The stabilizer 375 includes the handle segment 105, the arm segment 115, and stabilizing segment 110. The stabilizer also includes a channel 380 that passes through the handle segment 105 and the arm segment 115, and optionally into the stabilizing segment 110. The channel 380 can split into a pair of channels 385 that extend into the feet 120. Heated or cooled fluid can be directed into the channels 380 and 385 to heat and/or cool the stabilizer. The fluid can be provided from a tube 387 that is connected to an opening 390 in the handle segment 105, although the opening can be placed elsewhere in the stabilizer, such as, for example, in the arm segment. The tube 387 is connected on its other end to, for example, a pump 393, a bag of fluid, reservoir, or other source of providing heated or cooled fluid.

The tube also can be configured to have a dual lumen with both lumens opening into the handle opening 390. The other end of the tube can terminate to a pair of connectors that are each in communication with one of the lumens. In this configuration, a source of cooled or heated fluid can be inserted through one lumen into the channel 380 and withdrawn through the other lumen by a suction, a vacuum source, active pumping of the fluid, or combination of these methods or other similar methods. In this manner, the temperature of the fluid provided to the stabilizer 375 can be quickly increased or decreased. In this configuration, the stabilizer can include temperature sensors (e.g., thermocouples, thermistors) or probes to measure localized temperature to provide temperature feedback information for the physician. This information can be used as part of a feedback loop in temperature sensing and controlling to control the heating or cooling of the tissue surface or stabilizer component to maintain or control the temperature of the tissue and/or stabilizer, for example, based on a set point.

Referring to FIG. 29, in another implementation of a method to heat or cool the stabilizer 375, a dual lumen, temperature control tube 400 can be inserted into the opening 390 and passed into the channel 380. The dual lumen tube 400 includes a pair of connectors 405 that are each in communication with one of the lumens 410. One of the connectors 405 can be connected to a fluid source and the other connector can be connected to a fluid withdrawal apparatus, such as a pumping, vacuum, or suction source, an opening, or merely gravity. A closure insert 415 can be used to hold the position of the tube 400 within the channel 380 and provide a fluid tight seal. For example, the insert 415 can be threadably inserted into the opening 390 such that fluid will not pass out the opening 390 except through one of the lumens 410 of the tube. The insert may include a central opening that includes a gasket and the tube passes through the gasket in a fluid-tight manner. Alternatively, a fitting with a rotatable end cap may be rotated to compress a circular valve material, such as silicone, around the component to lock the component in position in the stabilizer. The tube also may include side holes 420 along its length through which fluid can be inserted and/or removed. The distal end of the tube also can be opened, closed, or one of the openings opened and the other closed.

Using a controlled source of heated or cooled fluid, the surgeon can minimize the amount of time that the stabilizing segment is rigidly in contact with the tissue. For example, shortly before the surgeon is to stabilize the tissue he can inject heated fluid to cause the stabilizing segment 110 and/or the arm segment 115 to become rigid. Similarly, if the surgeon believes that the rigidity is excessive for the particular surgical condition, he can specify a reduction in the temperature of the fluid being supplied to the stabilizer. After training, it is anticipated that the surgeon will be able to mentally connect the fluid temperature with the rigidity of the stabilizer and be able to quickly specify a temperature to provide the needed rigidity or flexibility. The surgeon also can specify a fluid temperature based on knowledge or belief that temperature will have a therapeutic effect on the tissue.

The stabilizers described above can be made using a number of materials and methods. For example, the shaft or arm segment material can be made from a superelastic and/or shape memory alloy, such as nitinol (a nickel titanium alloy). These materials are available in many configurations, and from suppliers, such as NDC (Fremont, Calif.); Memry Corporation (Bethel, Conn.); and Shape Memory Applications, Inc. (San Jose, Calif.). Other materials that can be used include spring stainless steel (e.g., 17-7), other spring metal alloys such as Elgiloy™ or Inconel™, and superelastic polymers.

Figure 30:
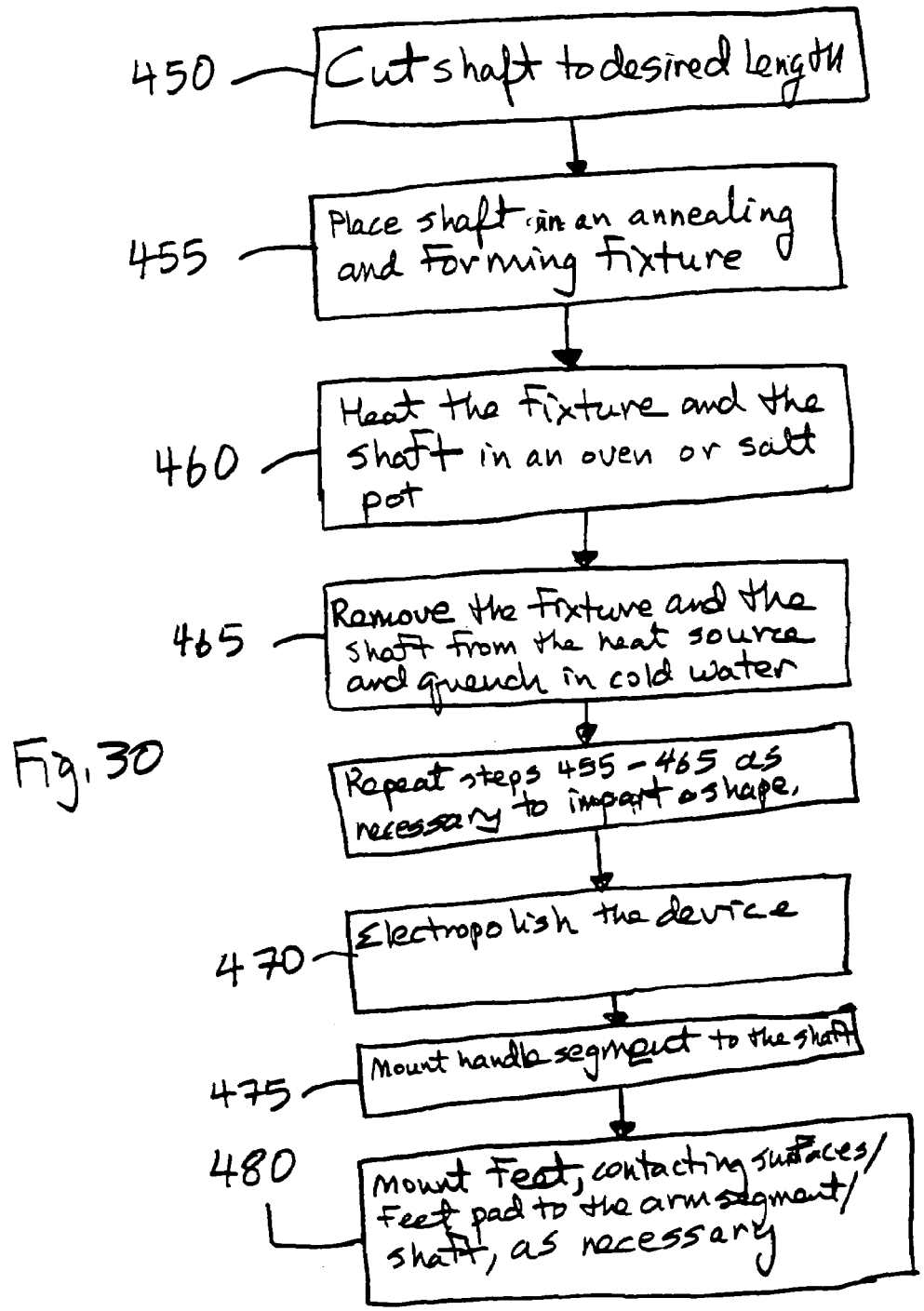
FIG. 30 is a flow chart depicting the fabrication of an exemplary stabilizer.

Referring to FIG. 30, which details an exemplary process for forming a superelastic/shape memory stabilizer, the shaft or arm segment 115 can be processed into the desired shape and size using a number of well-known methods, such as electronic discharge machining (EDM), laser cutting, photolithography and chemical etching, grinding, cutting, sintering, casting, molding, stamping, and/or any combination of these methods. First, the shaft material, and other optional shape memory/superelastic component, would be formed to the desired length, for example, by any cutting method (step 450). The shaft and other component then would be placed or positioned in an annealing and forming fixture to impart a desired shape in the material (step 455). The arm segment can be made from a sheet, a bar, a single or multiple tube or rod. The shaft may be a tube with a slot at the distal end that is annealed into the desired footpad configuration. The shaft may be of consistent width or thickness, or varied to modify the rigidity/flexibility, or other characteristic of the stabilizer.

The arm segment can be made from one or more rods, tubes, bands, coils, or other. They also may be partially or completely coated (or over molded) with any biologically acceptable material, such as a low friction polymer. As illustrated above, the arm segment may have one or more lumens that, for example, pass from the proximal end handle to the distal region of the stabilizer, for suction, $CO_2$ or saline misting, or for other purposes. The lumens may be on the inside, outside or both of the shaft, and could be constructed from a metal, metal alloy or polymer, or combination. The stabilizer may be a composite made from stainless steel (or other material) with the transition area between the arm segment and the feet or stabilizing segment being partially or completely made from superelastic/shape memory material or spring metal alloy, essentially becoming a deflectable hinge or elbow that may or may not require reinforcement, for example, using a reinforcing mandril or sleeve once inside the thoracic cavity or other body cavity.

The annealing fixture may have one or more surfaces around which the shaft would be positioned into a constrained arrangement, which closely resembles the final deployed configuration. The fixture also may be adjustable to make slight modifications in the shape due to, for example, changes necessitated by the surgeon or by the annealing process. The annealing fixture may be made from a metallic material that is able to withstand the annealing temperatures, and may have single or multiple components or sections. To anneal multiple arm segments simultaneously, the various components or sections of the fixture may be held together with clamps, screws, rods, or combinations of these or other components.

The fixture then would be subjected to heat, for example, by being placed in an oven or a salt pot (step 460). To anneal a superelastic or shape memory alloy, the alloy should be subjected to a temperature of approximately 300-800° Celsius for approximately two to thirty minutes. For example, a temperature of approximately 500° Celsius has been used successfully to fabricate a tissue stabilizer. The temperature and the time spent annealing are dependent upon factors, such as the thickness of the material (e.g., the stabilizer and the annealing fixture), the material, and the shape to be imparted, etc. Following annealing, the material is removed from the heat and quickly quenched in cold water (step 465). Steps 455-465 may be repeated as necessary, including adjustment of the fixture to make small, increment changes in the radius of curvature, angle, or bend between each annealing cycle to prevent over-stressing of the material when securing it to the fixture. After the shape is imparted in the material, it may be bead blasted, electropolished, or other suitable method that cleans and smoothes the surface and remove any burrs from the surfaces (step 470).

The handle segment may be, for example, injection molded polycarbonate or another polymer material. The handle could be over-molded directly onto the stabilizer shaft, or molded separately and then bonded to the shaft with adhesives or other (step 475). The handle segment also may incorporate a connection means for vacuum, $CO_2$ or saline misting, reinforcing or shaping mandrils, or other purpose, as described above.

The feet 120 and contacting surfaces or feet pad 125 optionally then are mounted to the arm segment 115 (step 480). Of course, the feet 120 can be integrally formed with the arm segment. If not integrally formed, the feet 120 can be mounted to the arm segments by using any known means, including welding, soldering, an adhesive, by a mechanical interference fit, by a ball and socket arrangement, using locking geometries, using a thumb or Allen screw friction locking mechanism, and/or a twist type locking mechanism.

The feet 120 may be formed from a metal material, such as a superelastic material, and have the polymer-based contacting surface (125) over-molded directly onto the feet, or be molded and then bonded to the feet by a mechanical interference fit, an adhesive combination, or other conventional attachment means as is well-known in the art.

Figure 31A:
FIGS. 31A-S are bottom views of the feet and/or contacting surfaces showing various textured surfaces suitable for improved contact with a tissue surface.
Figure 31B:
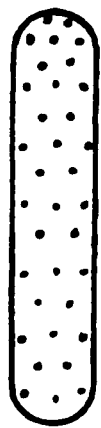
Figure 31C:
Figure 31D:
Figure 31E:
Figure 31F:
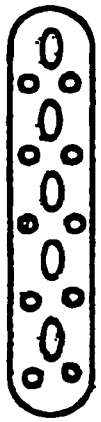
Figure 31G:
Figure 31H:
Figure 31I:
Figure 31J:
Figure 31K:
Figure 31L:
Figure 31M:
Figure 31N:
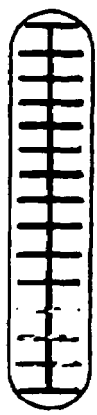
Figure 31O:
Figure 31P:
Figure 31Q:
Figure 31R:
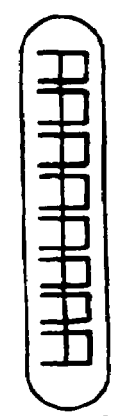
Figure 31S:
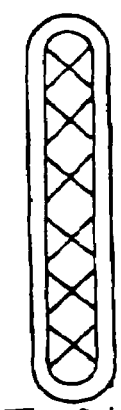

Referring to FIGS. 31A-S, the contacting surfaces 125 can have a variety of surface textures that are configured to resist slipping when placed against a tissue surface.

Referring to FIGS. 32A-H, the feet 120 themselves also can be formed to have any geometry suitable or desired for the intended application. As illustrated, the feet can be connected at one end, although such a connection is not necessary in all applications. Some of the possible geometries include two parallel lines, "U", "V", "W", and any combination of these. The feet may be solid or have one or more lumens for static or active suction, as described in more detail below. The lumens may exit on the bottom of the feet 120, contacting surface 125, or any other suitable location. The bottom of the feet may be textured to prevent slippage while in contact with the heart surface and in this manner the need for the contacting surface 125 is lessened.

The formation or fabrication of the feet 120 and the contacting surface 125 may be related. The contacting surface 125 may be partially or completely fabricated from many different types of synthetic biocompatible materials, including expanded polytetrafluoroethylene (ePTFE), polyester (including PET), woven Dacron, PEEK, polypropylene, polyurethane, silicone, polyamide, polyimide, nylon, polyethylene, combination or other suitable materials. Some polymer materials could be irradiated in a desired geometry, for the shape to be "set" into that position, which could be helpful to provide a particular profile. A similar process using heat instead of radiation could be used where the thermoplastic polymer is annealed (and cooled) into a particular shape and geometry.

The contacting surface 125 may be fabricated using injection-molding, casting, or other suitable molding techniques. The molds would be designed to mold the element/device material inside, outside, in-between, around, or any combination of these, the superelastic/shape memory (or other material) elements, making the elements an integral part of the device. In general, the steps are as follows: an injection mold is prepared, having the general characteristics that will result in a device shown herein. The superelastic/shape memory (or other) elements, such as the feet 120, are placed at desired locations in the mold. The desired polymeric (or other) material is then injected into the mold with the elements in place, prevented from moving, so that they are integrated into the mold. The injected material is allowed to cure, and the contacting surface, with the elements (i.e., feet 120) are removed from the mold. The superelastic/shape memory (or other) could be processed into the desired shape and configuration using several methods, such as electron discharge machining (EDM), laser cutting, chemical etching, grinding, cutting, photolithography, water jet cutting, any combination of these, or other suitable method.

As may be evident, the feet 120 and the contacting surfaces may have many configurations. For example, the feet and/or contacting surfaces may be in contact with the tissue using compression, suction (static or active), cryo, adhesive (e.g., low strength or reversible bioadhesives), low durometer polymers, tissue penetration, protrusions, a combination of these, or any other suitable method. There may be one or more feet and/or contacting surfaces. The feet and/or contacting surfaces may be separate pieces; may be coated or bare; and/or may be made from a tube, rod, bar, coil, band, sheet, rectangular material, or other suitable raw stock. As illustrated above, the feet and/or contacting surfaces may have a profile that is elongated, rectangular, round, oval, trapezoidal, zigzag, combination of these, or another profile. The contacting surfaces may have matching or mirrored geometries. The feet and/or contacting surfaces may have holes, grooves, slots, or other openings formed partially or completely through the width and or thickness. The feet and/or contacting surfaces may have the bottom, tissue contacting surfaces, be textured, grooved, dimpled, a combination of these, or other surface, to prevent slippage while in contact with the heart. The bottom of the feet and/or contacting surfaces may be concave, convex, or a combination of these configurations.

In addition to making the transition region between the shaft and footpads essentially flat during insertion into the chest wall, the footpads could also be folded together to reduce the cross section profile. The feet and/or contacting surfaces may be fabricated with metallic supports on the outside, the inside, in-between, or any combination of these, to modify the rigidity, flexibility, or other characteristic of the feet and/or contacting surfaces. Moreover, the shape of the feet can be modified by inserting a reinforcing member into an opening on the back end of the feet. The reinforcing member can be configured as described above and can be used to straighten, reinforce, or shape the feet. The reinforcing member or members can be malleable or rigid, or have a combination of these characteristics on the same member, depending on the purpose or application for using it.

The feet and/or contacting surfaces may be constructed of one or more durometer polymers. For example, the top (non-tissue contacting surface) may be made from a harder, higher durometer material than the tissue-contacting surface for increased rigidity, while not sacrificing tissue-contacting stability.

The feet and/or contacting surfaces may contain malleable materials on the outside, the inside, in-between, or any combination of these that would allow regions or sections to be bent into custom geometries by the surgeon. Alternatively, the feet and/or contacting surfaces may be reinforced with materials exhibiting spring-like characteristics. The feet and/or contacting surfaces may be designed and sold to be interchangeable for different designs/purposes by the surgeon. The feet and/or contacting surfaces may have a consistent or variable thickness cross-section for different purposes. For example, any area of the footpad that would cross the artery (e.g., the bottom section of a "U" shape stabilizing segment) and possibly compress the vessel and restrict blood flow may be configured with a raised, concave section. The feet and/or contacting surfaces may have a geometry or other means to better present (i.e., appose, bring together, or pucker) to the surgeon the coronary vessel at the site of the anastomosis or the other target tissue to the surgeon.

The feet and/or contacting surfaces may be partially or completely made from very low durometer materials to assist or ensure better contact with the tissue surface.

Referring to FIGS. 33A-35B, the stabilizer segment 110 or the combination of the feet 120 and the contacting surface 125 can be configured with a suction apparatus 500 to apply suction to the tissue surface to which the stabilizer is applied. A suction tube 505 can pass through any one of, all or, or any combination of, the handle segment 105, the arm segment 115, and the stabilizer segment 110. The suction tube 505 also may be attached to the outside of the stabilizer and connected to an opening in the contacting surface to the suction apparatus 500. Such a suction tube 505 may be formed from a polymer with a metallic or polymer coil, braid, or winding on the inside, outside, or in-between two polymer layers to resist tubular collapse while the suction is active. This configuration would also allow bending movement and/or positioning, while resisting kinking. As illustrated in FIGS. 33A-35B, the suction apparatus 500 may be positioned at the bottom of the contacting surface 125 and may have suction spheres 510 through which a vacuum is applied to the tissue. The suction apparatus also may have a screen mesh (not shown) or other screening system to prevent tissue or other debris from clogging the suction tube 505. The suction apparatus 500 also may include one or more rigid supports 515 that are positioned within the suction apparatus and prevent it from collapsing upon itself when vacuum is applied to the suction apparatus. The rigid supports 515 may include grooves, channels, or domes 520 that keep the vacuum flowing through the suction apparatus even when the sac-like apparatus collapses upon itself.

Local suction can be accomplished by using soft, low durometer material for the suction spheres 510 on the tissue contacting surfaces, or by having lumens connecting the spheres 510 leading to a valve or fitting, such as a Luer fitting, to which a syringe, bulb, or other suction device could be attached and a vacuum created, and the valve closed to maintain the suction. In general, local suction is accomplished without attachment to an external vacuum source and instead is accomplished, for example, using a syringe or other physician manipulated device to pull a vacuum. A Luer-lock or stopcock then can be used to close the line containing the vacuum to leave a vacuum condition. In general, a remote vacuum suction system is attached to a vacuum line. To prevent collapsing of the vacuum line, a metallic or plastic coil may be used inside of the line, in the wall of the line, or on the outside of the line.

Figure 36:
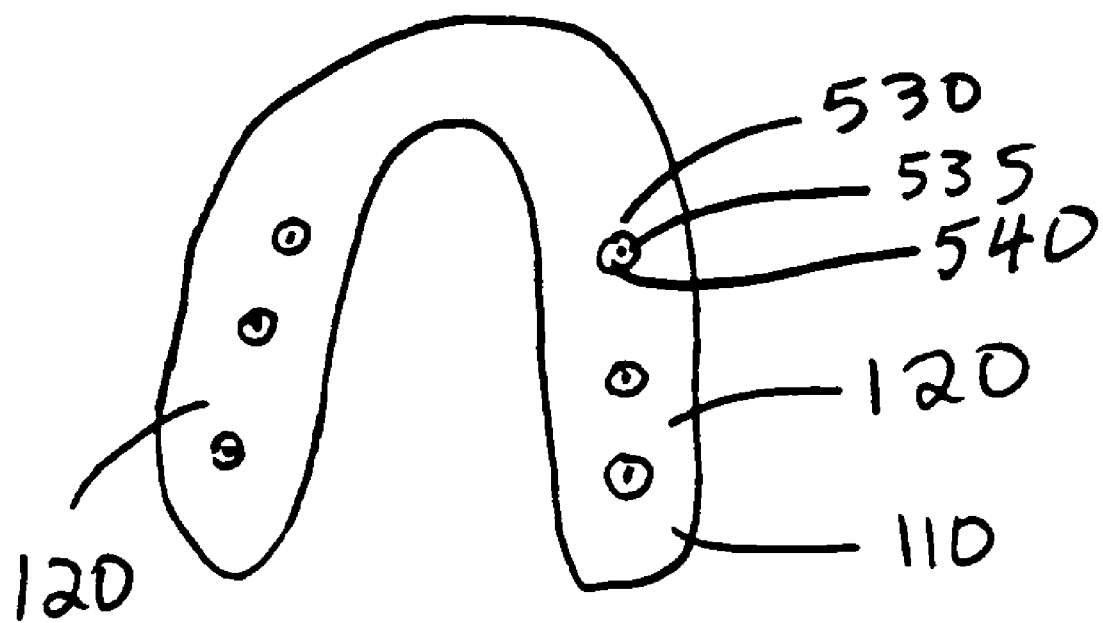
FIG. 36 is a bottom view of stabilizing segment having protrusions or barbs extending from the stabilizing segment.
Figure 37:
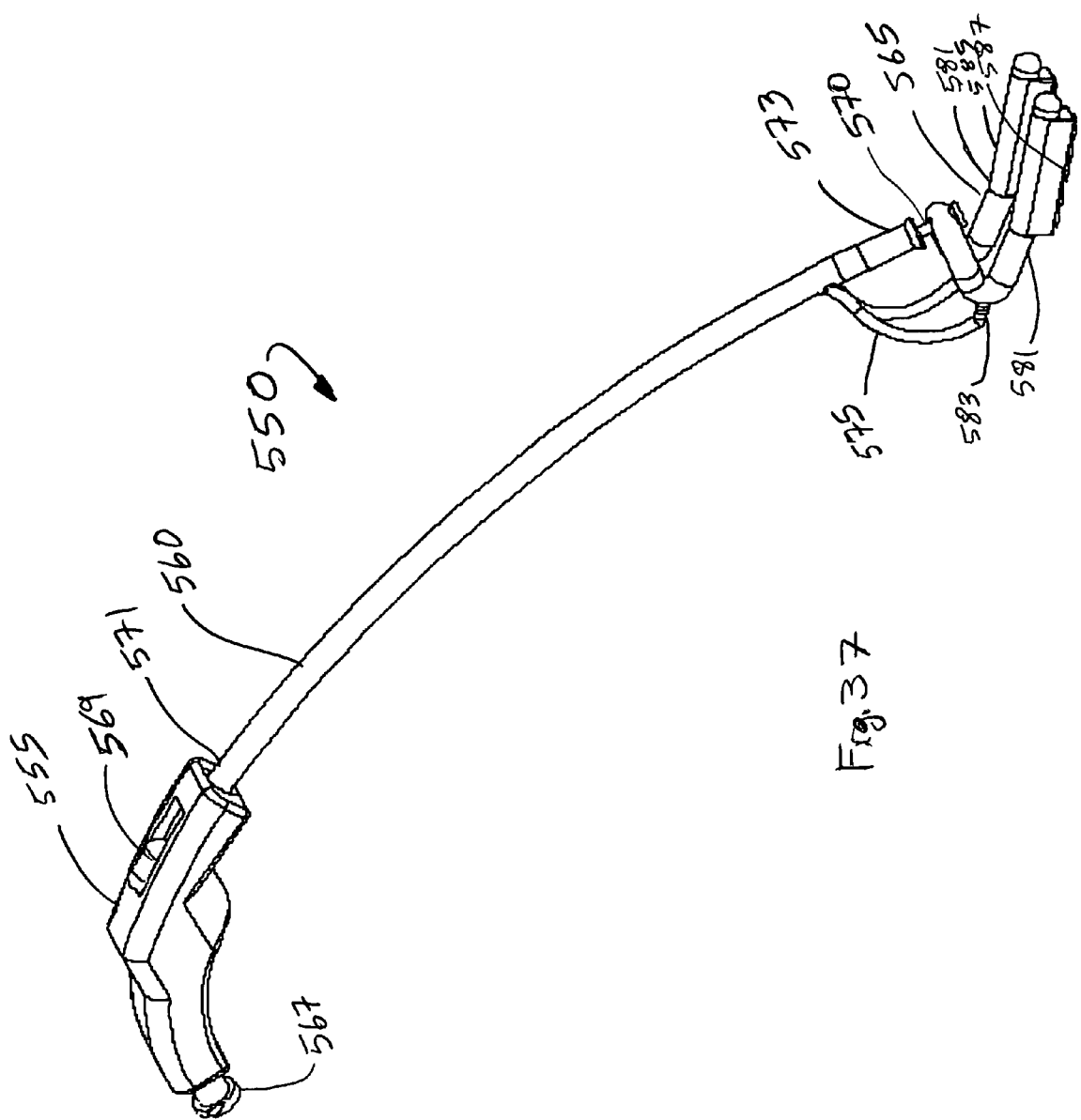
FIG. 37 is a perspective view of a stabilizer having vacuum capability.
Figure 38:
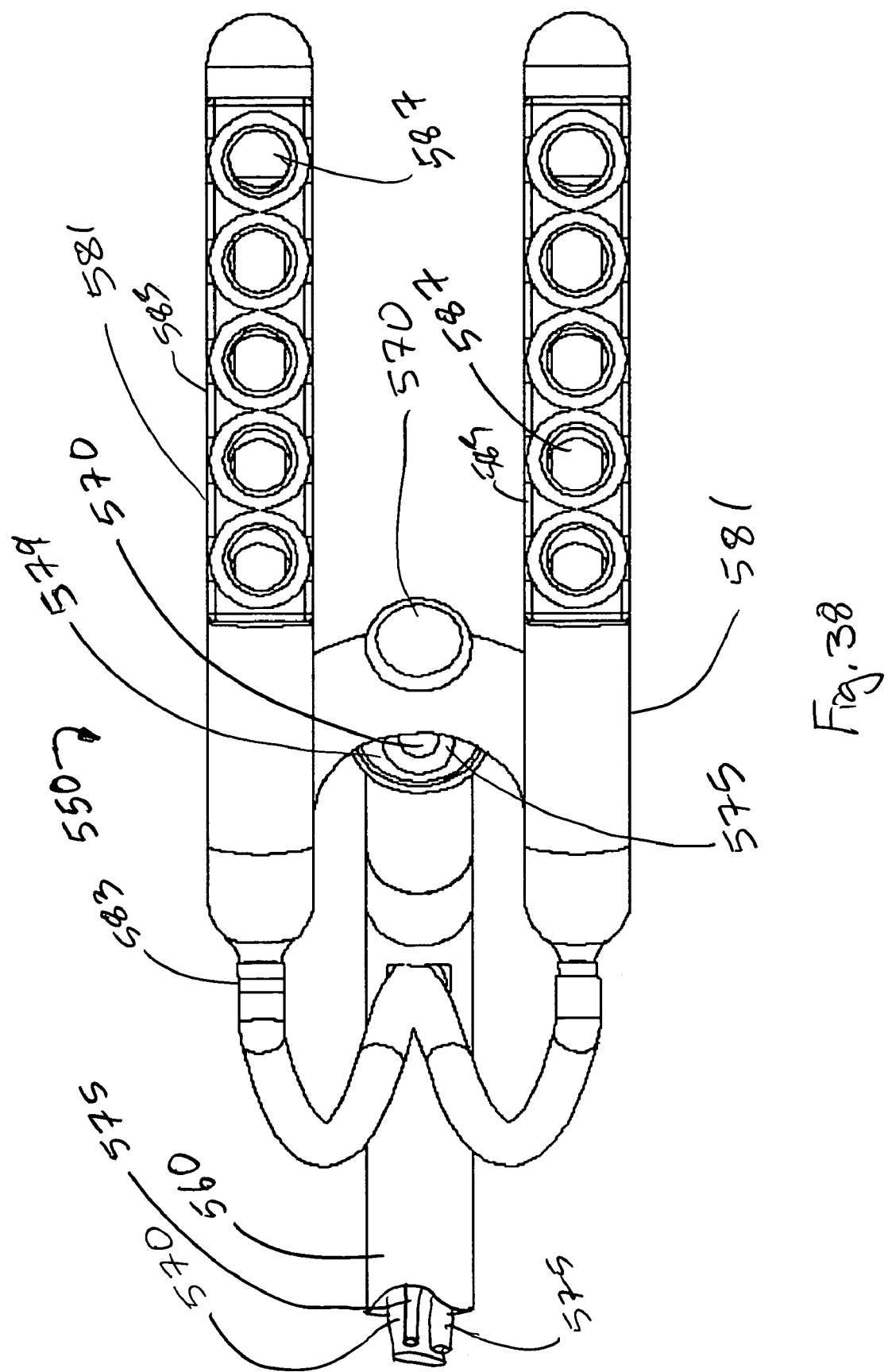
FIG. 38 is a bottom view of a stabilizer segment of the stabilizer of FIG. 37.
Figure 39:
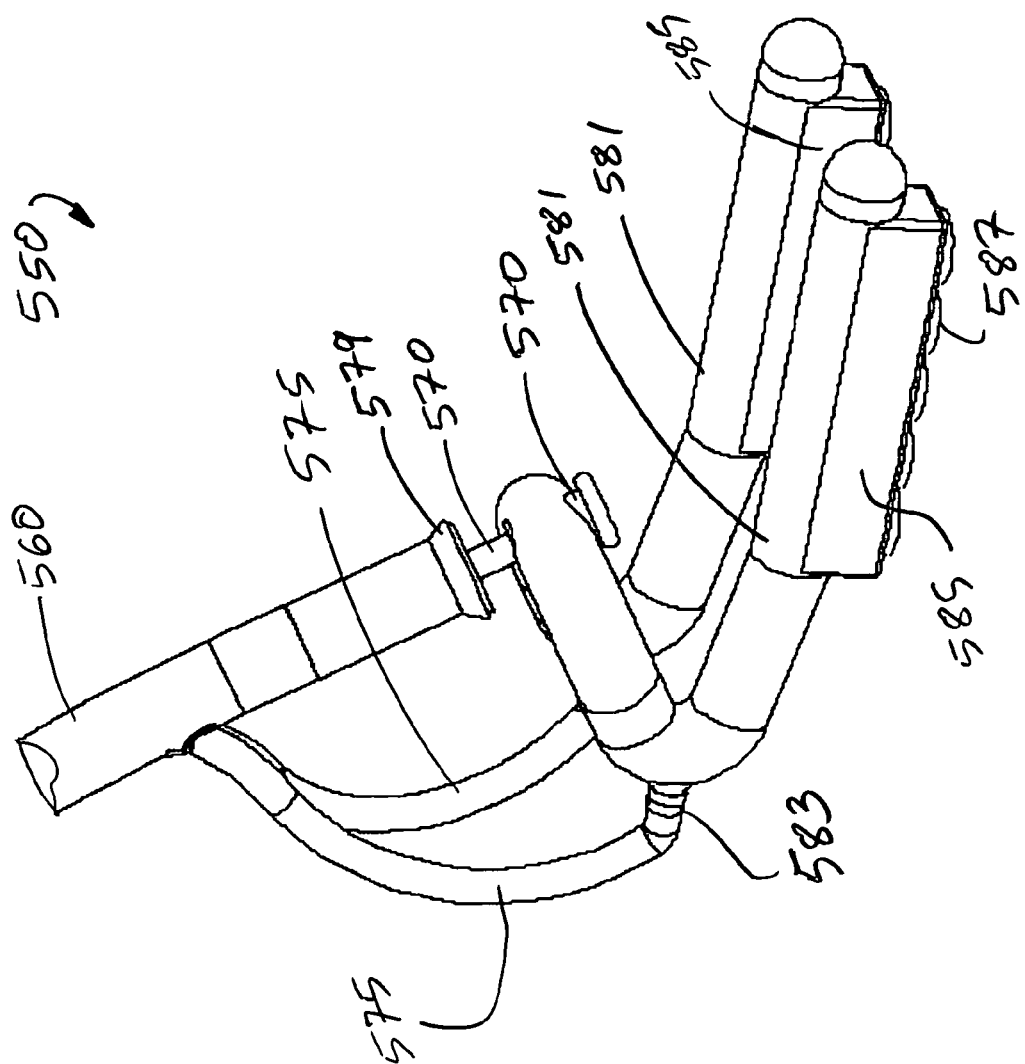
FIG. 39 is an enlarged view of the attachment of the stabilizer segment to the stabilizer.
Figure 40:
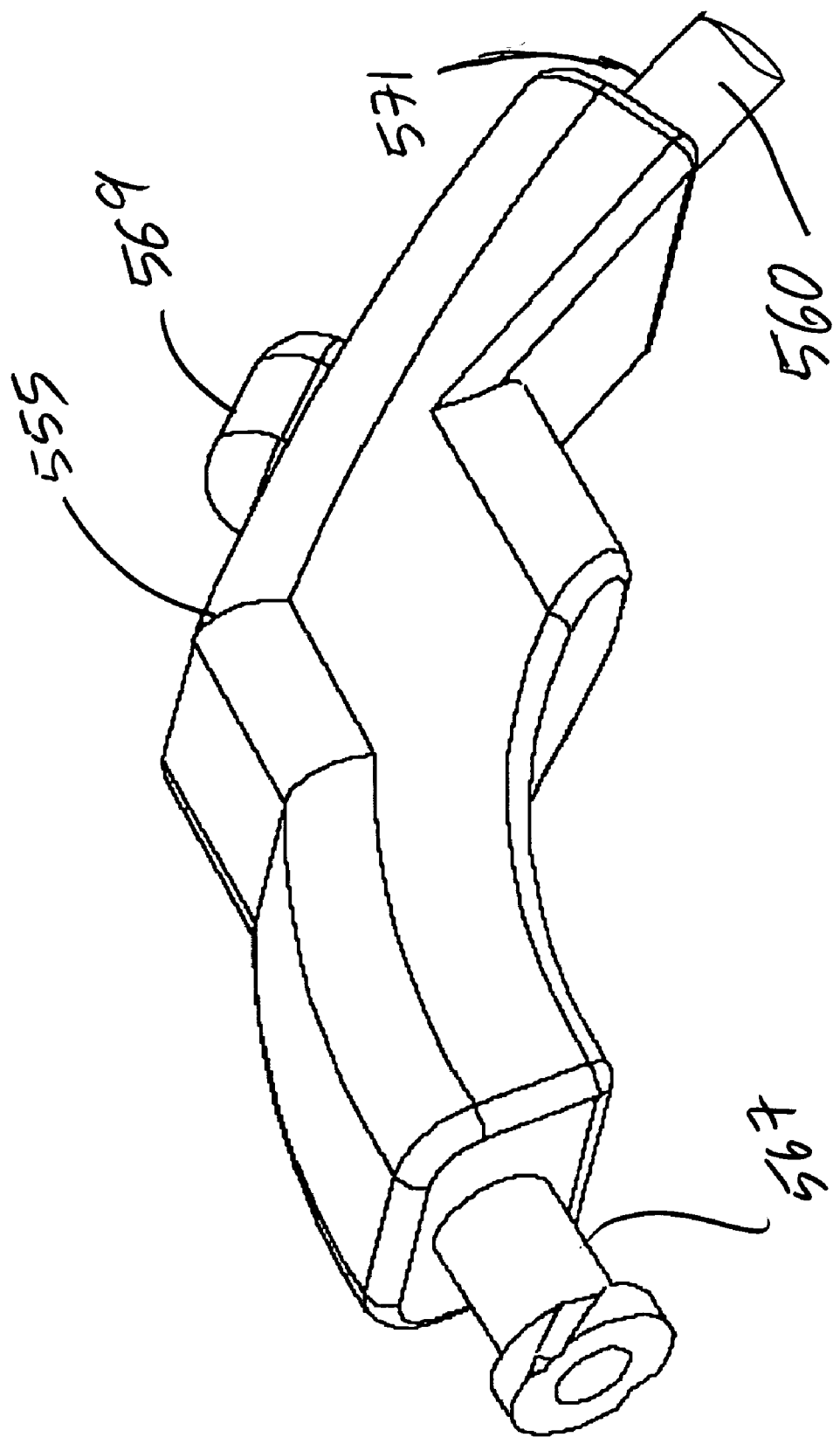
FIG. 40 is an enlarged view of the handle of the stabilizer of FIG. 37.
Figure 41:
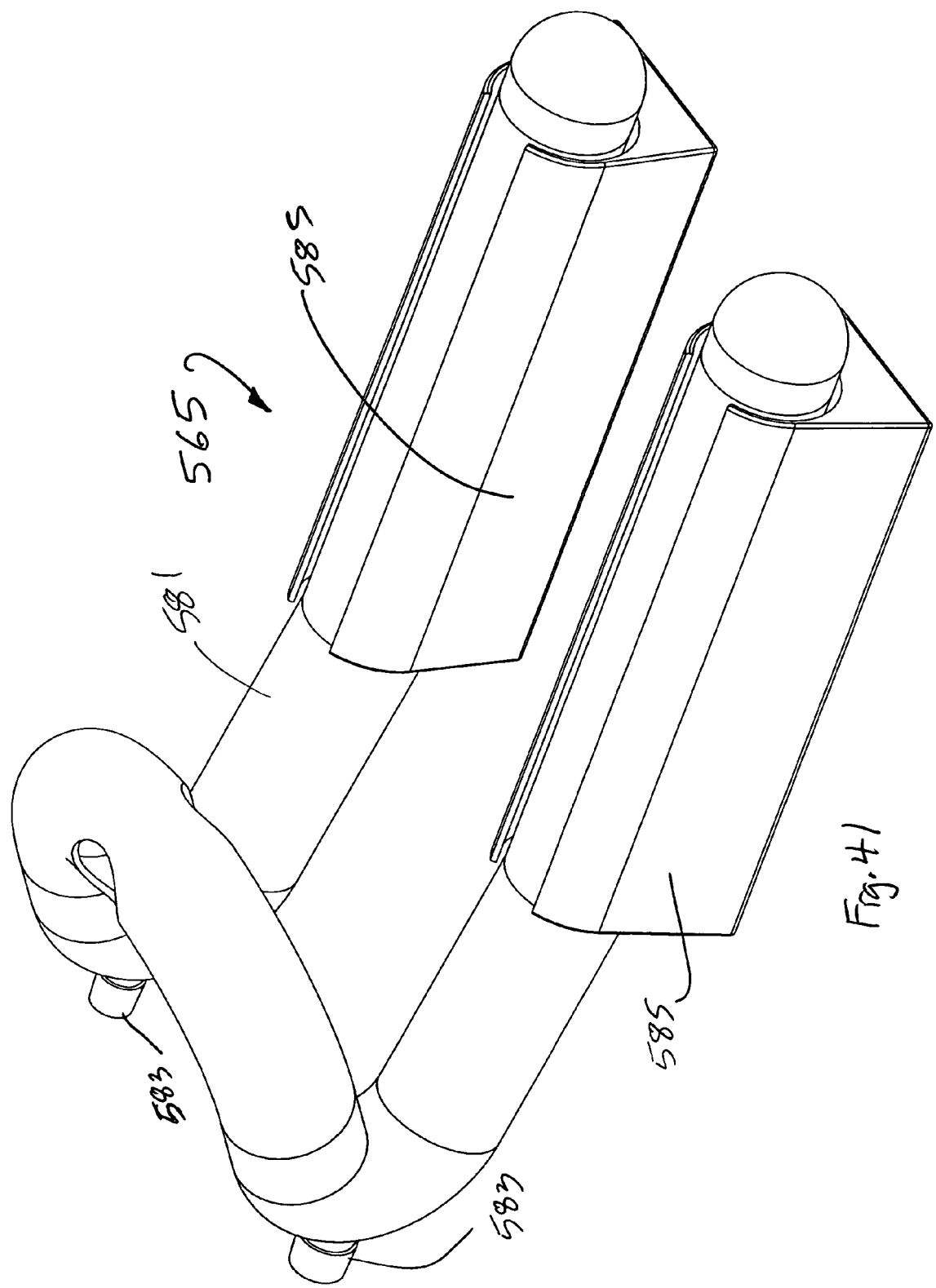
FIG. 41 is an enlarged view of stabilizer segment provided as a separate attachment to the stabilizer of FIG. 37.

Referring to FIG. 36, the stabilizer segment 110, the feet 120, and/or the contact surface 125 may have a protrusion or barb 530 that is inserted into the tissue to be stabilized to prevent slippage of the stabilizer relative to the tissue. The protrusion or barb 530 may be in the form of one or more wires 535 that pass through one or more lumens 540 in the stabilizer from the proximal end, through the arm segment, and through any portion of the stabilizer segment. The wires 535 may be controllably inserted to be limited in the depth to which they can be inserted. The control may be a stop on the proximal end of the wires that limits insertion of the wires into the lumens. Alternatively, protrusion may be molded or adhesively attached to tissue contacting areas. The protrusions may be straight or angled to prevent slippage in one or more planes.

Referring to FIGS. 37-41, a stabilizer 550 includes a handle 555, an arm 560, and a stabilizer segment 565. The handle 555 includes a port 567 for applying a vacuum to the stabilizer 550 and thumb switch 569 for controlling a linkage 570 within the arm 560 that is used to fix the position of the stabilizer segment 565 relative to the arm 560. The linkage 570 may be as simple as a rod that slides within a channel in the arm 560 and is connected to the stabilizer segment 565. The arm 560 includes a first end 571 that is connected to the handle 555 and a second end 573 that is adjacent to the stabilizer segment 565. Also within the arm 560 is a vacuum tube or tubes 575 that pass between the port 567 and stabilizer segment 565. The linkage 570 terminates at the stabilizer segment 565 and includes an enlarged portion 577 that fits against a curved surface 579. The enlarged portion 577 has a fixed position relative to the arm 560. As such, retracting the thumb switch 569 pulls the enlarged portion 577 in the direction of the curved surface 579 such that the enlarged portion and the curved surface are in contact to form a frictional fit. This friction fit prevents movement of the stabilizer segment 565 relative to the arm 560, a characteristic whose importance will be explained in greater detail below.

Although the linkage 570 is described above as being a rod, the linkage may be a wire or a cable that is positioned on the inside and or outside of the arm 560 and connected to the thumb switch. As a result, when the thumb switch 569 is pulled backward, the distal end or end component of the arm 560 is in tension against a component or components attached to the stabilizer segment 565. The thumb switch 569 also may be attached to an indexed movement (like a ratchet) or internal components that increase friction as they are moved in one direction.

The linkage 570 also may be implemented as a shaft, rod, or band on either the inside or outside of stabilizer arm 560 and connected to the thumb switch 569. As a result, when the thumb switch is advanced forward, the distal end or end component of the arm is in compression against a component or components attached to the stabilizer segment 565. As in the implementation above, the thumb switch 569 may be attached to an indexed movement (like a ratchet) or internal components that increase friction as they are moved in one direction.

The stabilizer segment 565 includes a pair of feet 581 that are joined at the termination of the linkage 570. The feet 581 include ports 583 for the vacuum lines 575 and tissue contacting segments 585 that include openings 587. The tissue contacting segments 585 can be separate pieces that are mounted to the feet 581 by, for example, a frictional sliding fit. The segments 585 can be disposable to facilitate cleaning of the stabilizer. The segments 585 also can be fabricated from an atraumatic material to reduce trauma to the tissue. The vacuum applied to the port 567 passes through the vacuum lines 575 and applies a vacuum to the openings 587. Thus, if the openings 587 are placed against tissue, such as the heart, the vacuum will tend to pull the heart tissue against the openings and position the stabilizer 550 against the heart muscle.

The stabilizer 550 can be fabricated from superelastic materials or shape memory materials depending on the characteristics that the surgeon desires from the stabilizer. For example, the arm 560 can be fabricated from a superelastic material such that the arm bows without permanent deformation. The superelastic resilience of the arm can be tailored such that the arm will bow if too much force is applied. This will limit the likelihood that too much force will be exerted against the heart. The elasticity of the arm also can be tailored such that applying force against the arm to bow it will cause a magnified force to be presented to the body applying the force. In general, the more the arm is bowed away from its annealed or resting configuration, the more compressive force is exerted by the arm against the tissue. In this manner, the stabilizer can be fabricated apply a great force to the body. The stabilizer segment 565 also benefits from the application of superelastic materials. For example, the entire stabilizer segment 565 or merely portions of it can be fabricated from a superelastic material to provide the characteristics attained when superelastic materials are applied to the arm 560.

The stabilizer 550 also can be fabricated from a shape memory metal so that the stabilizer can be inserted into body cavity in a first, reduced profile shape and then formed into a second shape. For example, the second shape can be formed as a result of exposure to body temperature or by actively heating the stabilizer. The shape memory stabilizer then can be withdrawn by cooling the stabilizer such that it returns to its reduced profile shape for easy withdrawal or by simply withdrawing the device.

Figure 42:
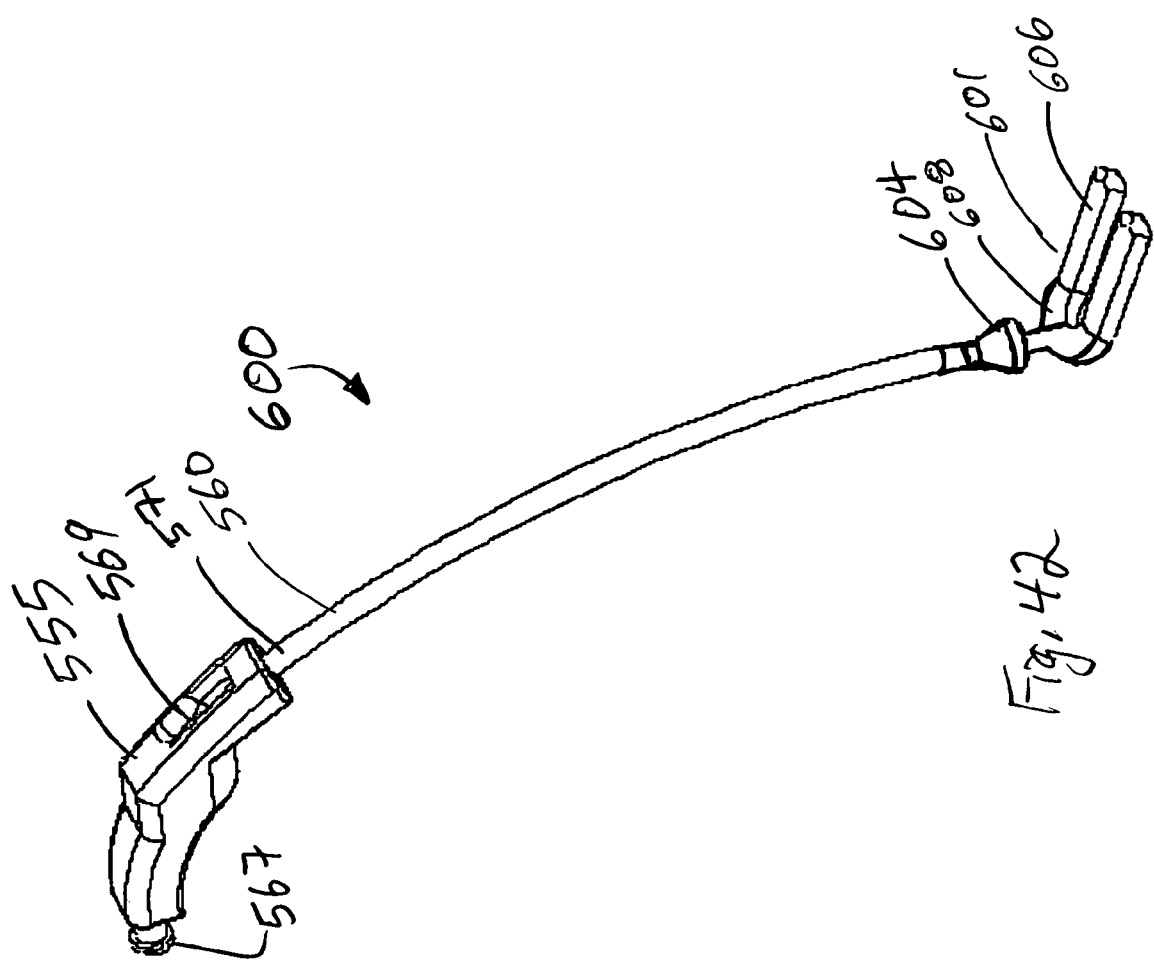
FIG. 42 is a perspective view of a stabilizer having internally placed vacuum lines.
Figure 43:
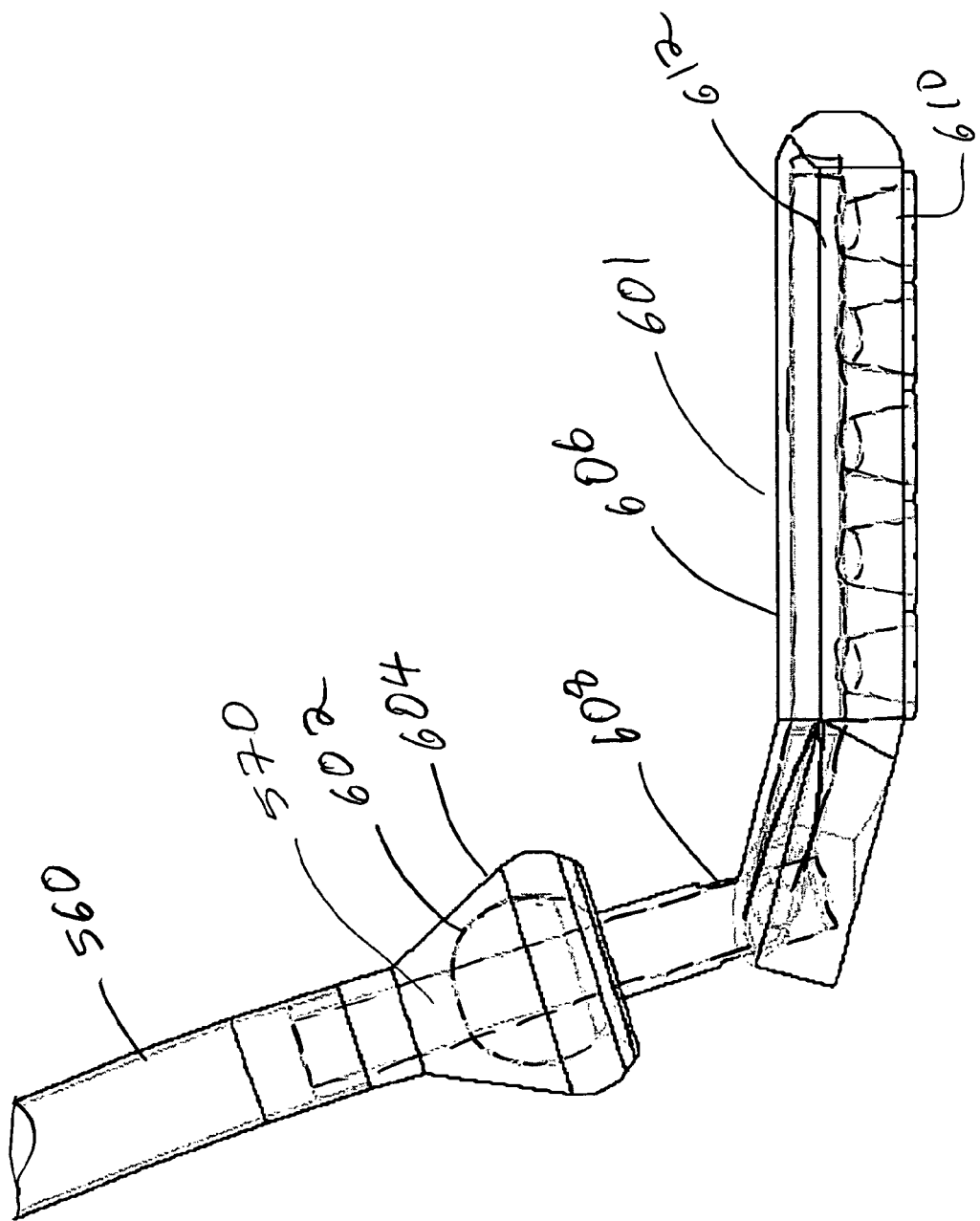
FIG. 43 is an enlarged side view of the attachment of the stabilizer segment to the stabilizer of FIG. 42.
Figure 44:
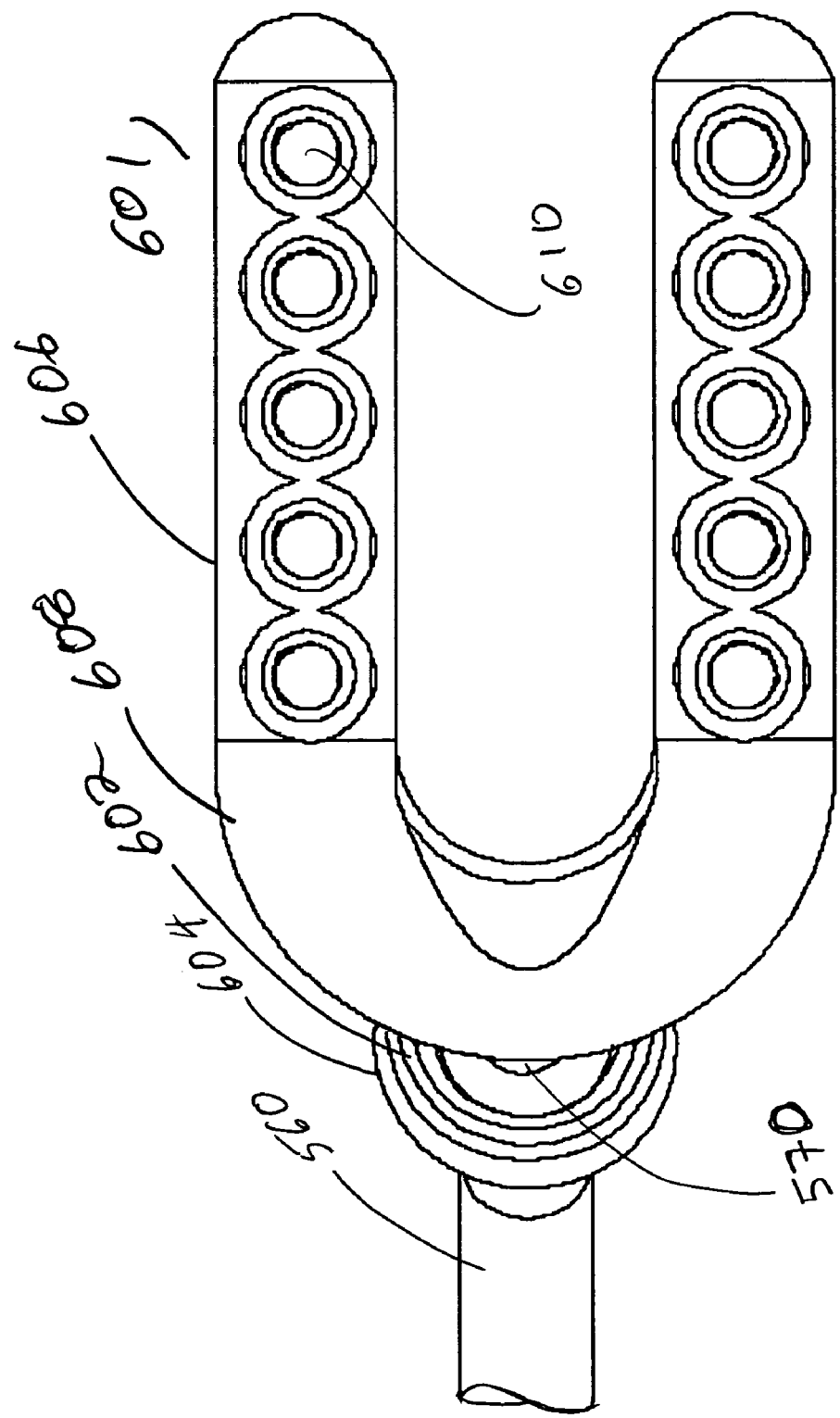
FIG. 44 is a bottom view of the stabilizer segment of the stabilizer of FIG. 42.

Referring to FIGS. 42-44, a stabilizer 600 is similar to the stabilizer 550 except for differences in the stabilizer segment 601 and the linkage 570. In particular, the enlarged portion 602 is larger than the enlarged portion 579 such that it will mate with an enlarged curved surface 604 that is larger than the curved surface 579. When the thumb switch 569 is advanced or retracted, depending upon the configuration as described above, the enlarged portion 602 mates with the curved surface 604 in a frictional mating that limits the movement of the stabilizer segment 601 with respect to the arm 560. Another difference between the stabilizer 600 and the stabilizer 550 is the placement of the vacuum lines 575. Instead of running outside of the arm 560 at the distal end 573, the vacuum lines 575 are contained within the arm 560 and pass from the arm to the stabilizer segment 601 without running on the outside of the stabilizer. To accomplish this, the vacuum lines 575 pass through the linkage 570 at least at the enlarged portion 602. For example, if the linkage 570 is in the form of a hollow tube, shaft, or rod, the vacuum lines 575 can be fed through the lumen of the tube, shaft, or rod. This advantageously reduces the profile of the stabilizer 600 at the junction between the arm 560 and the stabilizer segment 601. The stabilizer segment 601 has two sections, a tissue contacting section 606 and a pivot section 608. The pivot section 608 is connected to the linkage 570 and may include the enlarged portion 602. The tissue contacting section 606 includes openings 610 through which vacuum is applied to fix the stabilizer 600 against a tissue surface, such as a surface of the heart. A channel 612 within the stabilizer segment 601 connects the vacuum lines 575 to the openings 610. The tissue contacting section 608 can be a replaceable part that snaps or slides into the pivot section 608. Alternatively, the tissue contacting section 608 can be integrally formed or removable for cleaning.

Similarly to the stabilizer 550, the stabilizer segment 601 can be fabricated in part or in whole from superelastic or shape memory materials to obtain the same objectives described above. For example, the pivot segment 608 can be formed from a superelastic material to provide flexibility when the stabilizer is compressed against a tissue surface. The tissue contacting section 606 also can be fabricated from a superelastic material to provide flexibility.

Figure 45:
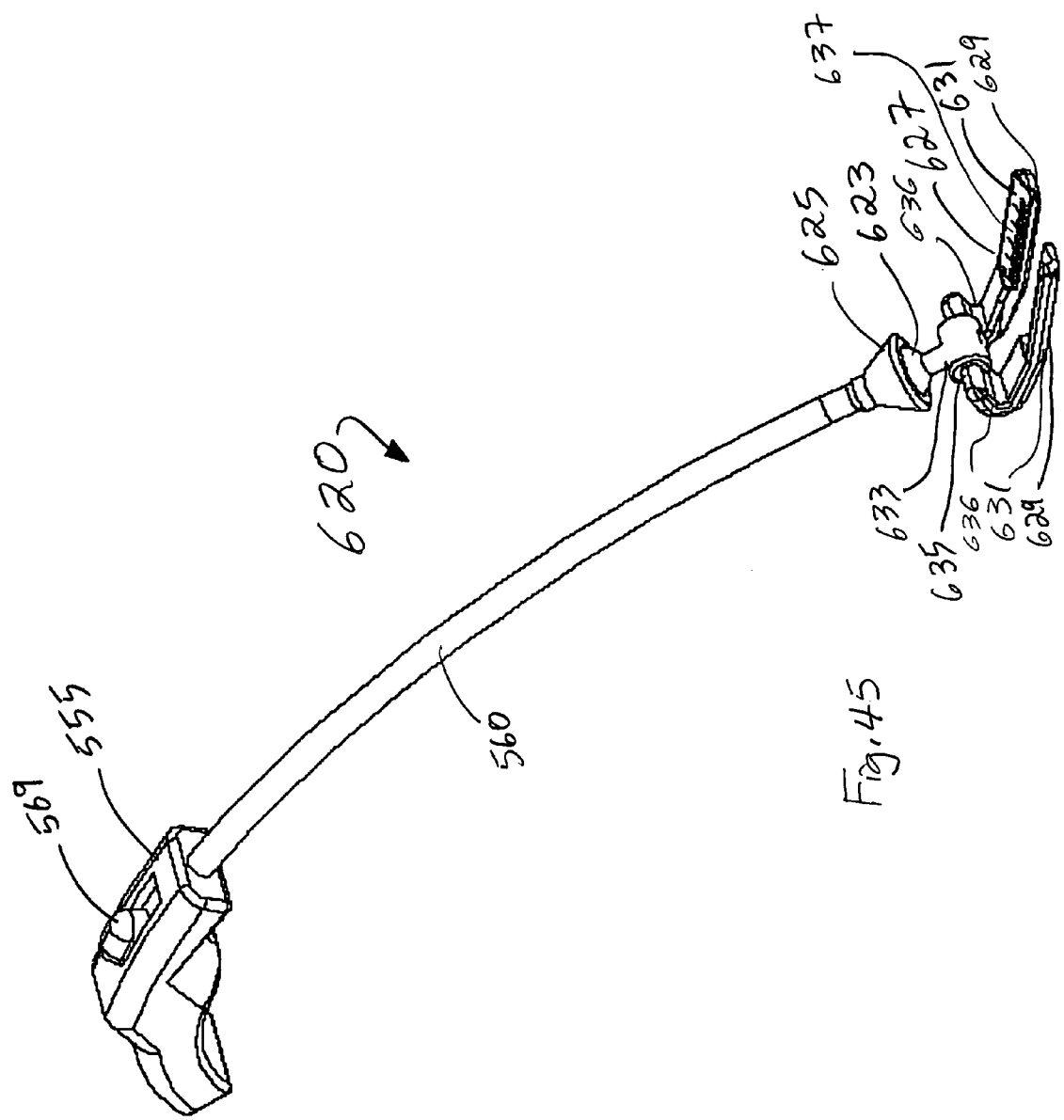
FIG. 45 is a perspective side view of a stabilizer having an indexed and pivotable stabilizer segment.
Figure 46:
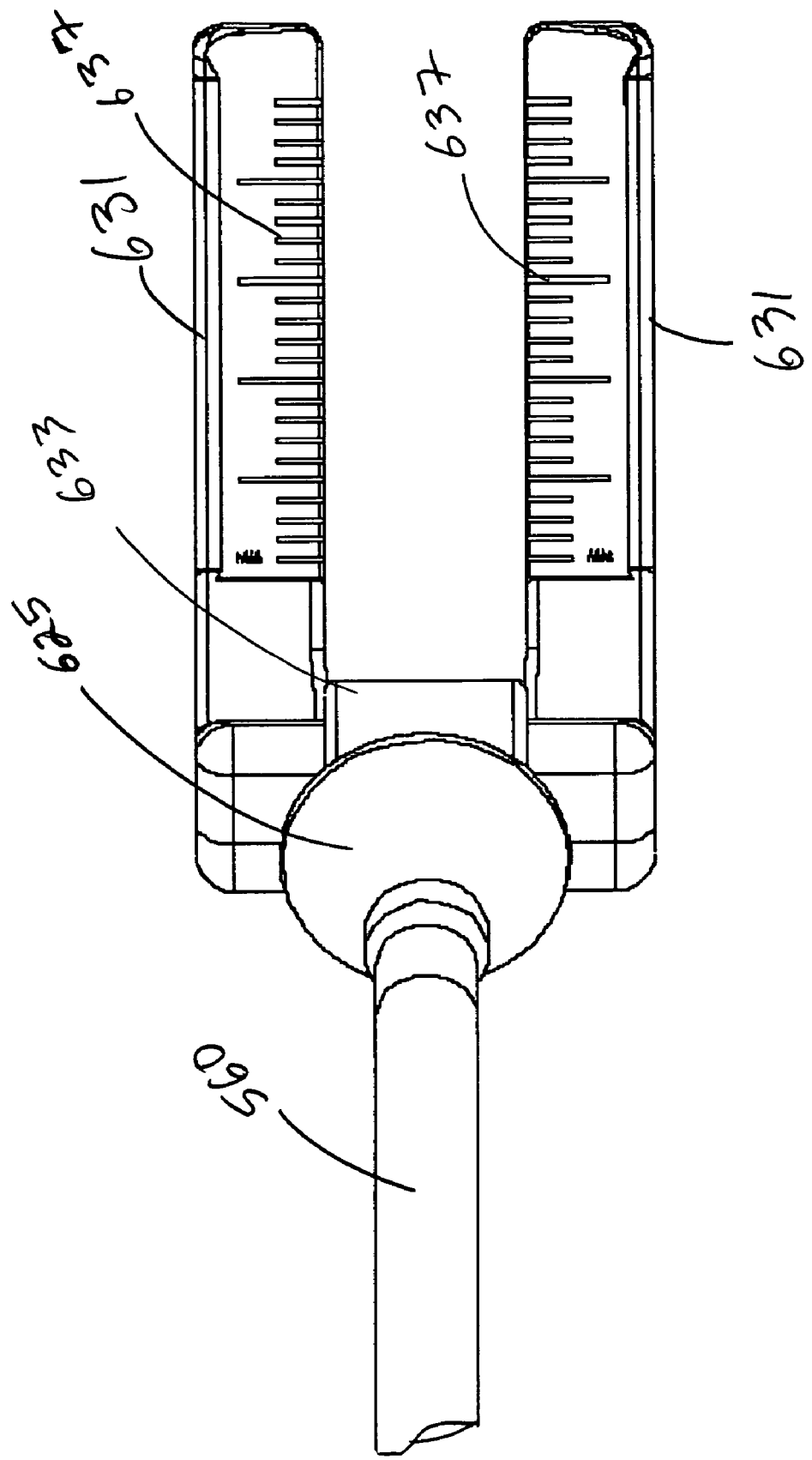
FIGS. 46 and 47 are enlarged top and perspective side views of the indexed and pivotable stabilizer segment of FIG. 45.

Referring to FIGS. 45 and 46, a stabilizer 620 is configured to include an enlarged portion 623 and a large curved surface 625. However, unlike the stabilizers 550 and 600, the stabilizer 620 is not configured to apply vacuum to a tissue surface. Instead, stabilization of the tissue is based on compression of the stabilizer segment 627 against the tissue surface. To provide increased stability, the stabilizer segment 627 can have a material applied to the tissue contacting surfaces 629 of the tissue contacting segments 631. The material has a non-slip surface so that it will have a reduced tendency to slide across the surface of the tissue.

The arm 560 and the stabilizer segment 627 pivotally connected by the enlarged portion 623 and the curved surface 625 such that the arm and stabilizer segment can pivot with respect to each other. In addition, the enlarged portion 623 is connected to a sleeve 633 that encircles a shaft 635 such that the arm can rotate around the stabilizer segment. Thus there are two mechanisms to position the arm relative to the stabilizer segment. The shaft 635 is connected to the tissue contacting segments 631 by a curved segment 636 that can be used to provide flexion in the stabilizer segment.

The tissue contacting segments 631 are marked with a guide 637 that is used by the surgeon to determine distances on the tissue surface. For example, the guide 637 can be marked in millimeter increments or English unit increments (e.g., sixteenths of an inch increments, eighth of an inch increments, etc.). This advantageously permits the surgeon to make the arteriotomy the correct length by viewing the markings and using them as a reference.

The stabilizer 620 can be fabricated in part or in whole from superelastic or shape memory materials. For example, the arm 560 can be fabricated from a superelastic material and provide the advantages described above. Similarly, the stabilizer segment can be fabricated in part or in whole from superelastic materials. For example, the curved segment 636 can be fabricated from a superelastic material to provide flexion in the stabilizer segment when the physician compresses the stabilizer against a tissue surface. The section of the linkage between the enlarged portion 623 and the sleeve 633 also can be fabricated from a superelastic material to provide flexibility along that axis.

Figure 47:
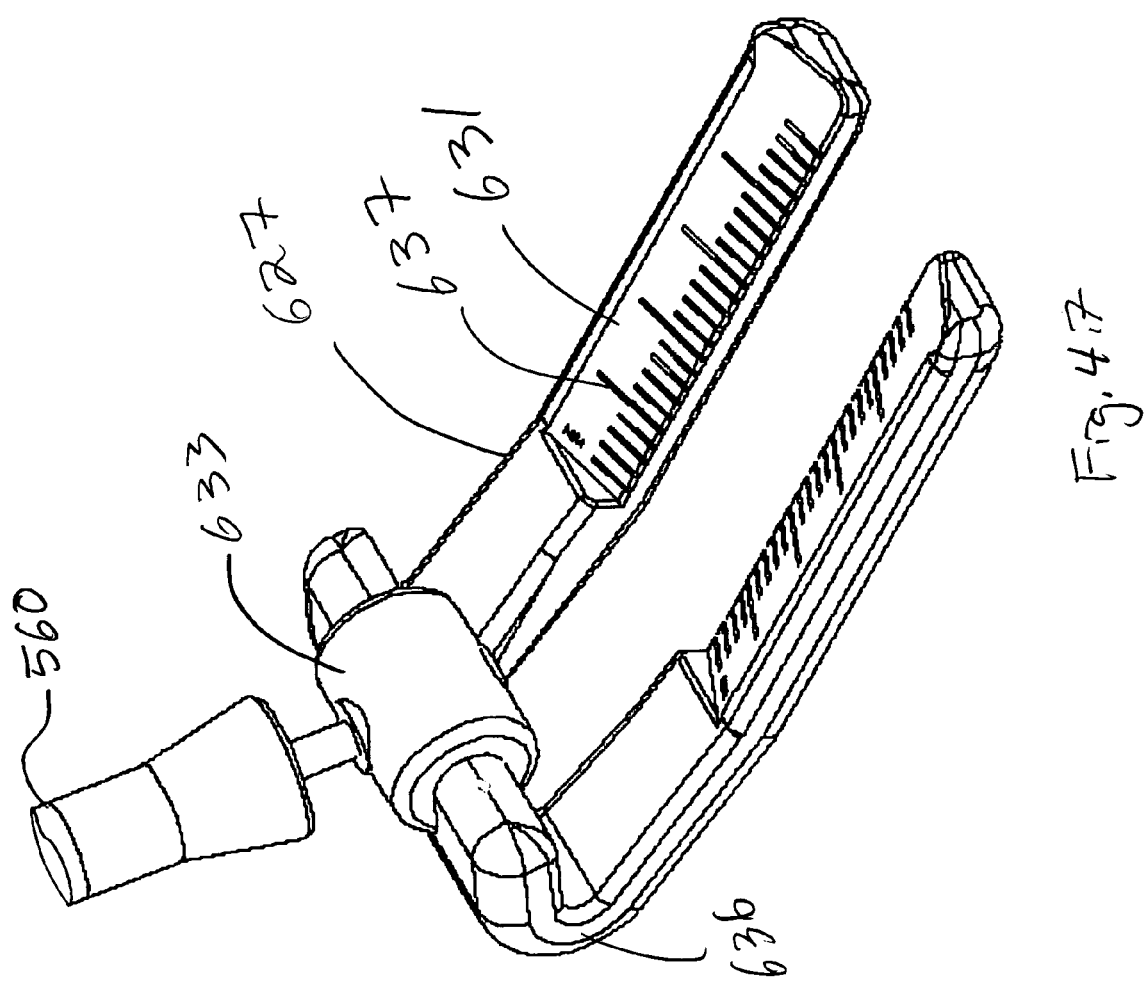
Figure 48:
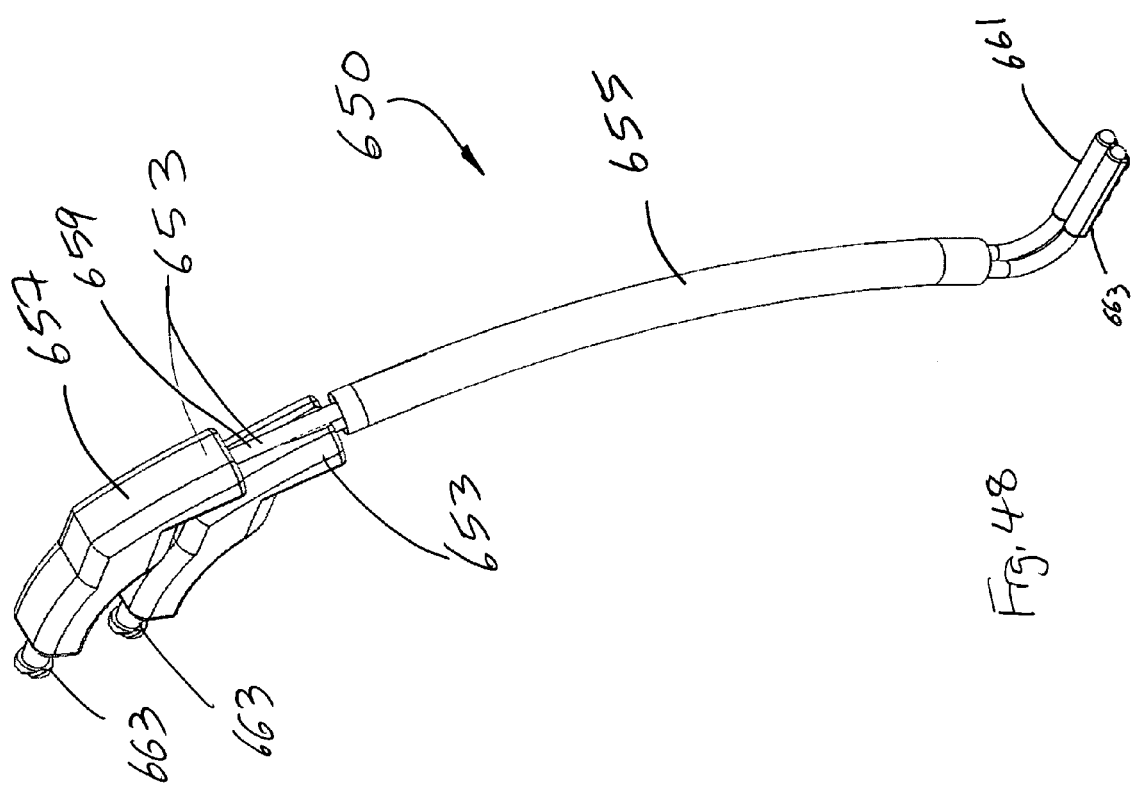
FIGS. 48 and 49 are perspective side views of a stabilizer having a pair of independent stabilizers.
Figure 49:
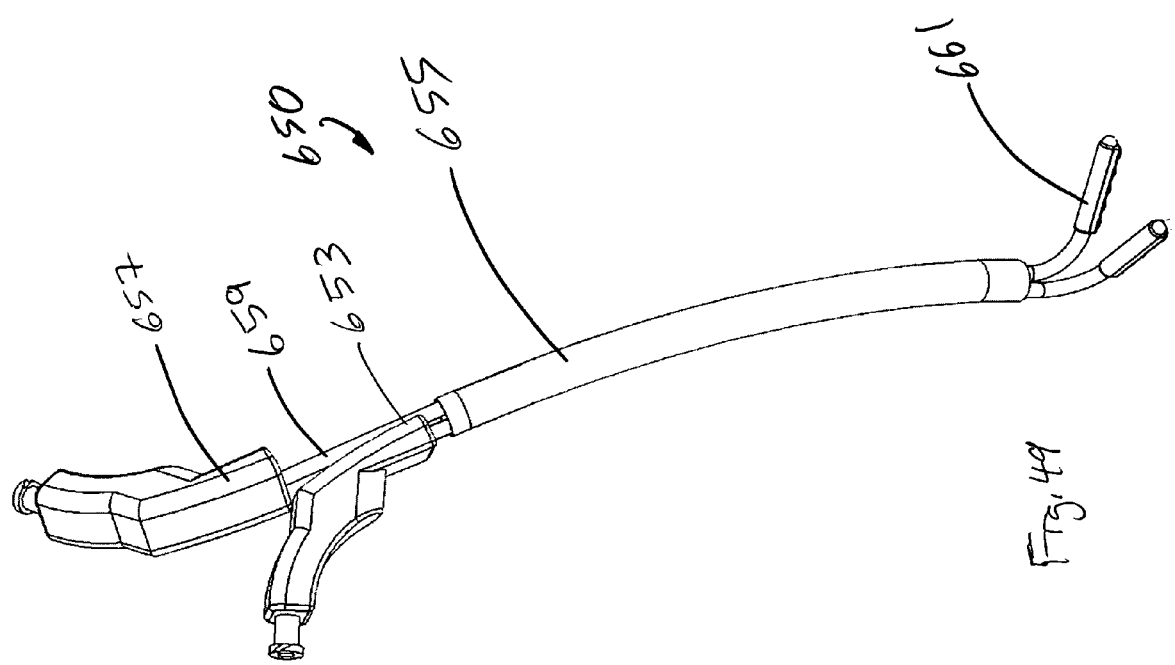
Figure 50:
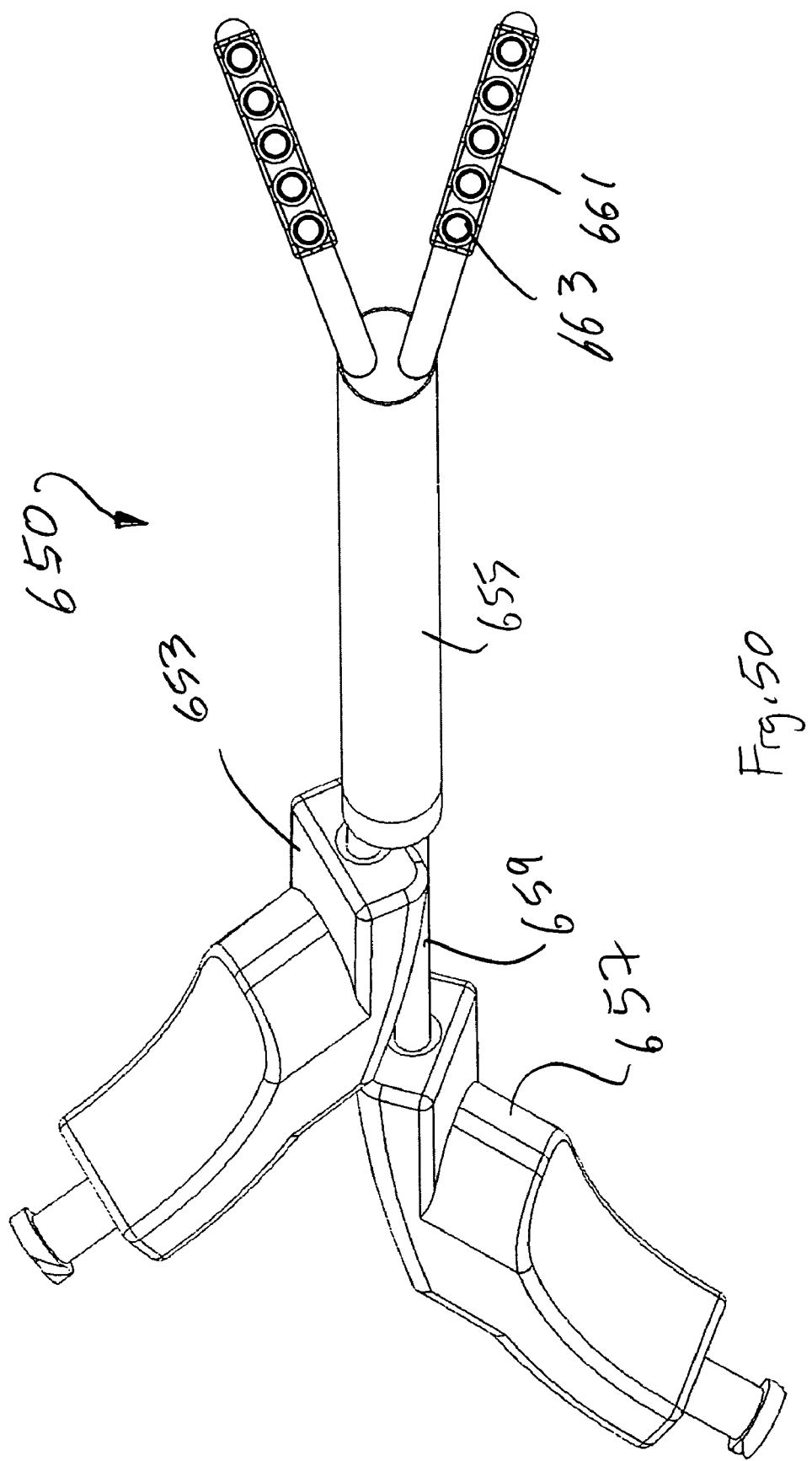
FIG. 50 is a perspective bottom view of the stabilizer of FIGS. 48 and 49.

Referring also to FIG. 47, the stabilizer 620 can include a pivot connection 642 between the arm 560 and the stabilizer segment 627 that is reduced in size in comparison to the connection of FIGS. 45 and 46. This limits the range of pivot motion that is possible, which can be advantageous in some circumstances in which there is little control of the stabilizer, such as in a confined space, and the physician wants to limit the uncontrolled movement of the stabilizer segment.

Referring to FIGS. 48-51, a stabilizer 650 includes a pair of independent stabilizers 653 and a delivery tube 655 through which the stabilizers 653 independently are slidable. Each stabilizer includes a handle 657, a shaft 659, and a foot 661. The handle 657 includes a port 663 through which a vacuum can be applied. The shaft 659 includes a lumen that connects to the foot 661 so that the vacuum can be applied through openings 663 in the foot. The surgeon using the stabilizer 650 can advance, rotate, and otherwise manipulate the independent stabilizers 653 to place them on a tissue surface adjacent to a surface to be operated upon.

Figure 51:
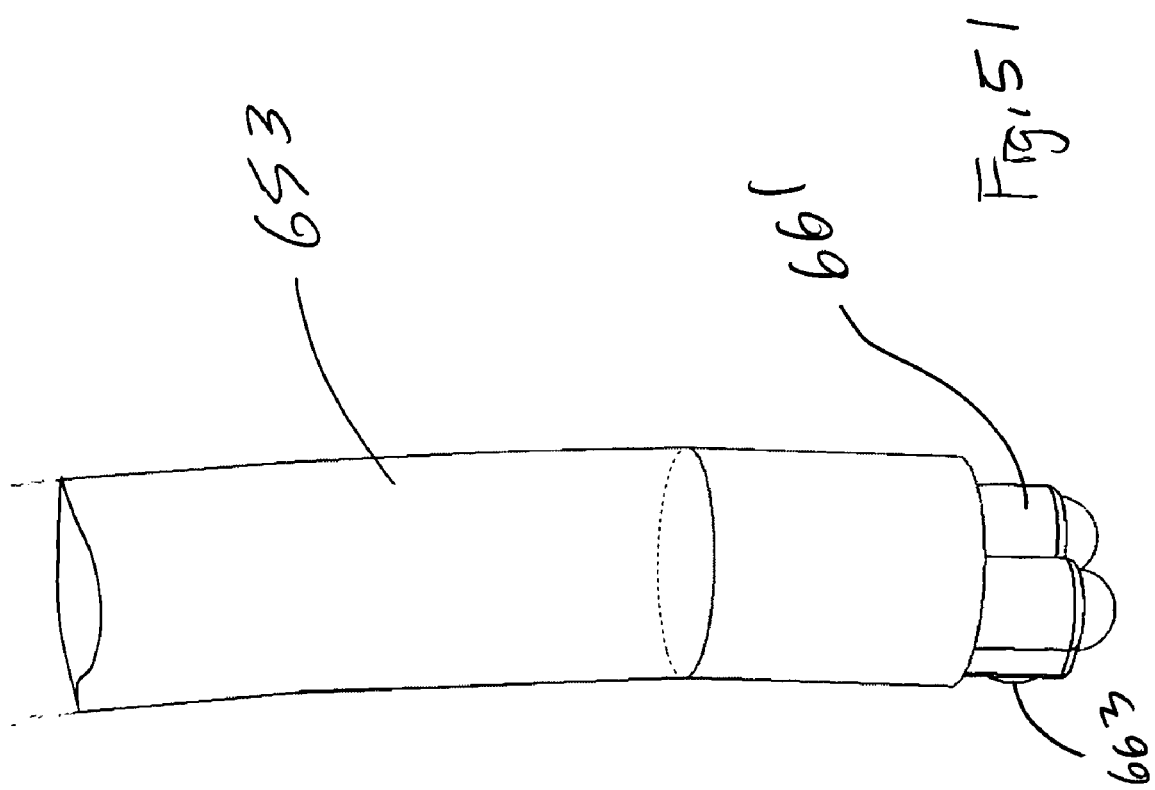
FIG. 51 is a side view of the independent stabilizers of FIGS. 48 and 49 withdrawn into a delivery tube.

The surgeon can insert the stabilizer 650 into a narrow opening by first pulling the independent stabilizers 653 back such that the feet 661 are completely withdrawn into the delivery tube 655 to provide a reduced profile (FIG. 51). With the delivery tube positioned within the body cavity, the surgeon then advances the independent stabilizers 653, separately or together, until the feet 661 are extended. The surgeon can independently manipulate the handles 657 to select a position of the feet 661 that allows the surgeon to stabilize the tissue. Although FIGS. 48-51 show simplified implementations of the feet 661, the feet can be implemented in a more complex configuration with the curves and bends illustrated in the feet and stabilizer segments described herein.

The center-to-center distance between the feet can be manipulated by moving the feet 661 apart, creating a "V" shape. Additionally, a snap on spacer component may be positioned in between the two feet as describe above with respect to FIGS. 26 and 27. Also, a thumb wheel type device (e.g., similar to that on a drafter's compass) may be used to manipulate the center-to-center width of the feet.

The surgeon has the option of applying vacuum to stabilize tissue with the stabilizer 650. The surgeon also can use the port and lumen to instead provide a solution to the tissue that the stabilizer is contacting. For example, the solution can be a therapeutic cooling or heating solution. The solution also can be a drug or other therapeutic agent. If the stabilizer is fabricated from a shape memory metal, the surgeon can pass a heating solution through the port 663 and lumen to cause the shape of the independent stabilizers to reach their larger profile shape. Then, when the stabilizer is to be removed, the surgeon injects a cold solution to cause the shape to return to the reduced profile configuration that is easily retracted into the tube 655. Of course, the independent stabilizers, in whole or in part, can be made from a superelastic material such that the surgeon merely pulls the independent stabilizers back into the tube 655 to cause them to be in the reduced profile configuration.

Figure 52:
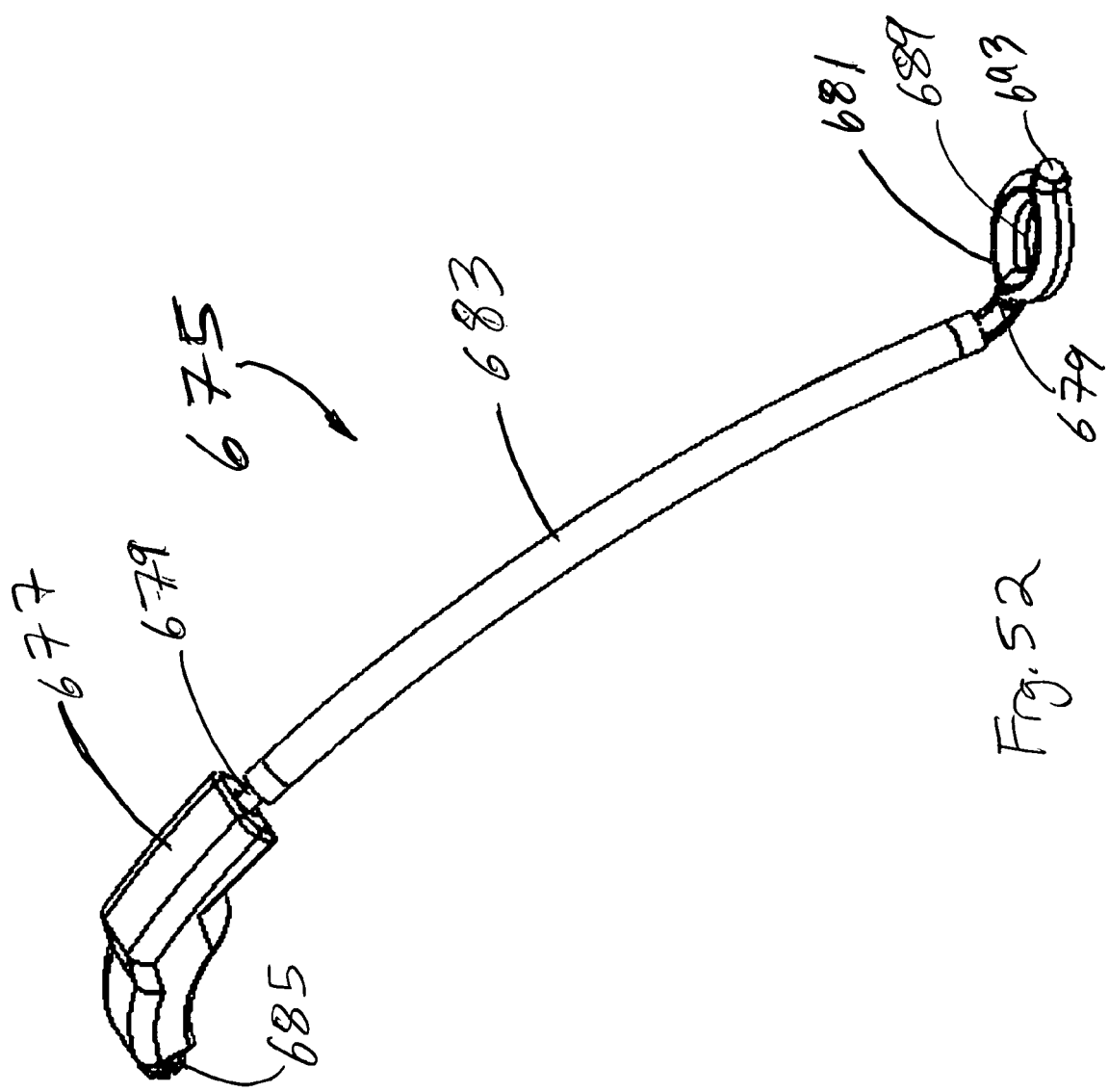
FIG. 52 is a perspective side view of a retractable stabilizer having an open stabilizer segment.
Figure 53:
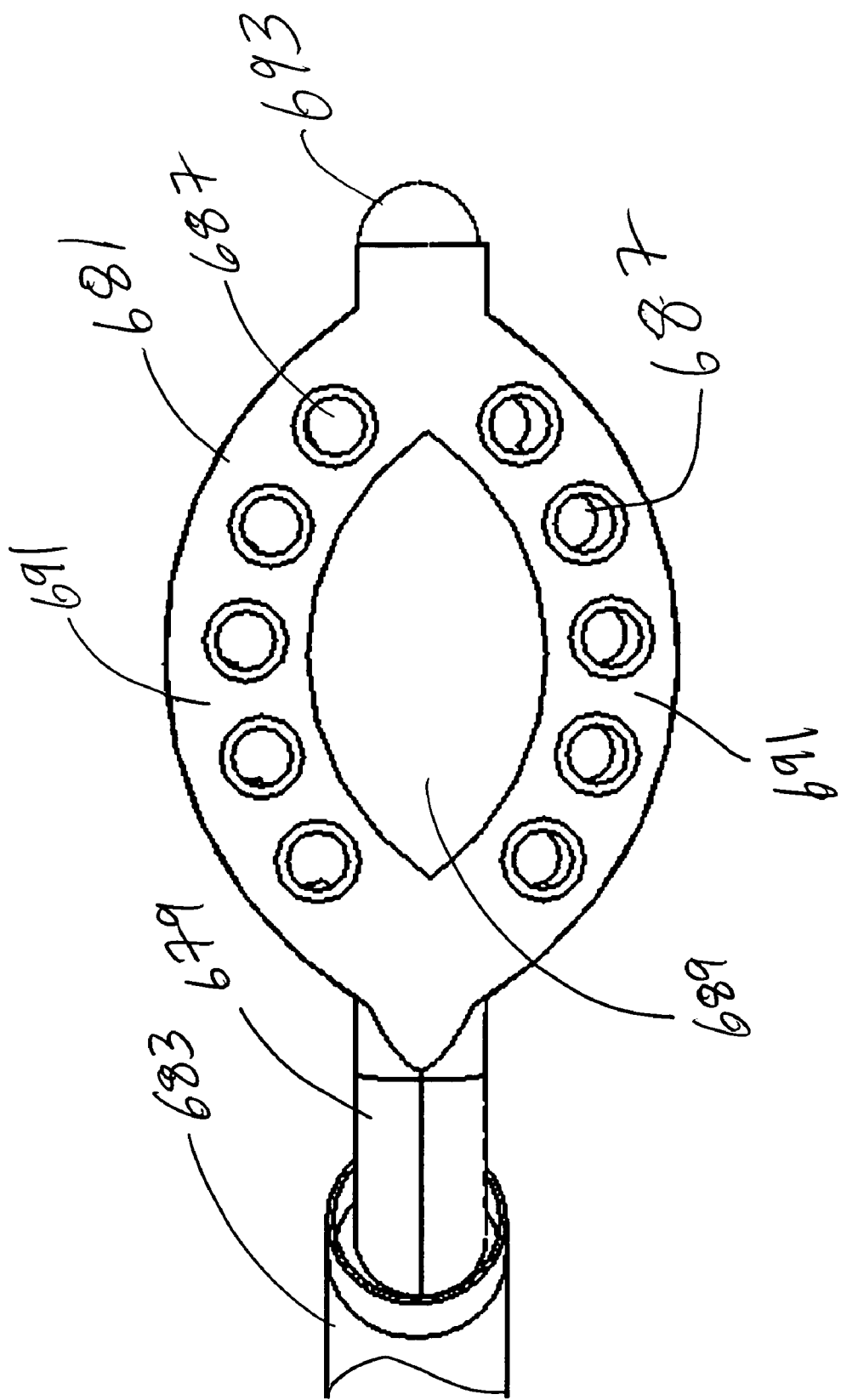
FIG. 53 is a bottom view of the open stabilizer segment of FIG. 52.
Figure 54:
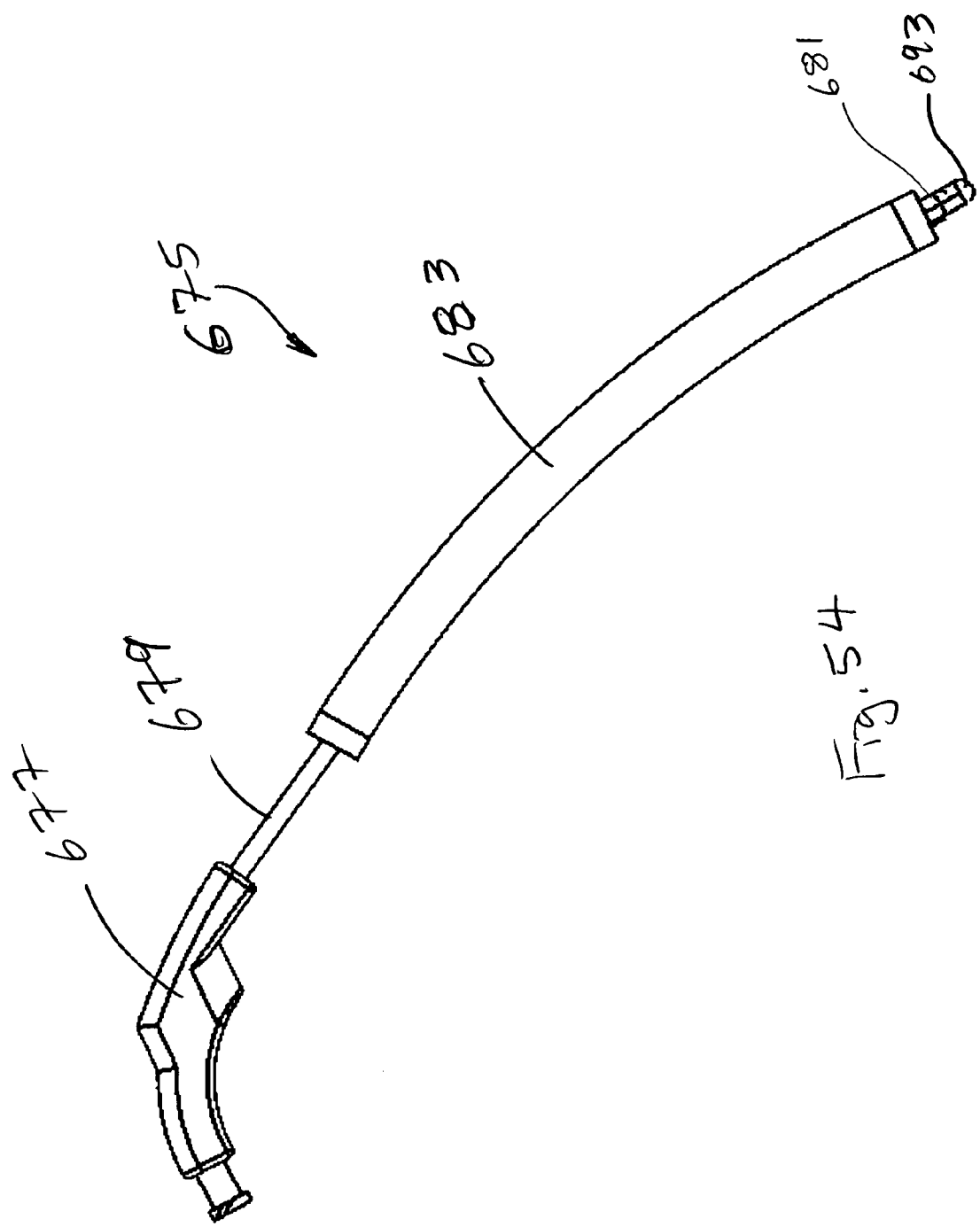
FIG. 54 is a side view of the retractable stabilizer of FIG. 52 having the open stabilizer segment withdrawn into a delivery tube.

Referring to FIGS. 52-54, a stabilizer 675 includes a handle 677, a shaft 679, and a stabilizer section 681. The shaft 679 is slidable within a delivery tube 683. The handle includes a port 685 for applying a vacuum or delivery a fluid through a lumen in the shaft 679 to apply a vacuum or deliver a fluid at the stabilizer section 681. The stabilizer section 681 includes openings 687 through which the vacuum or fluid is applied to a tissue surface. The stabilizer section 681 also includes an opening 689 between opposite feet sections 691. The physician is able to perform a procedure on tissue through the opening 689. The opening is formed by cutting a round, oval, flat, or otherwise shaped shaft along its length, generally along its central longitudinal axis. The cut can be formed using any known conventional cutting method, including a laser, a cutting saw, chemical etching, electron discharge machining (EDM), stamping, photolithographic techniques, water jet, and/or any combination of these methods or other suitable methods. The opposing sides of the cut then are forced outwardly to form the opening 689. The cut can be made through a distal end 693 of the shaft or can stop short of the distal end, as illustrated in FIGS. 52-54. The stabilizer 675 then is formed by shaping (e.g., annealing) the shaft and attaching the handle 677. Optionally, the distal end 693 can be elevated to prevent occlusion of a coronary artery if the stabilizer 675 is to be used in coronary artery bypass procedures. The cutting operation results in two concave opposing halves of the tube. To enclose these open halves, the entire length of each cut tube is overmolded. Alternatively, portions (e.g., the top, side, and bottom) of each concave opening is overmolded with a polymer as described herein. This overmold creates channels (e.g., vacuum channels or fluid flow channels), functions as an atraumatic tissue contacting surface, and forms mating surfaces when the stabilizer is collapsed. In a derivative implementation, multiple incisions may be made along the length of the shaft. For example, one central incision may be made along the length and extend through the distal end 693 and two incisions may be made in the thus formed opposing segments of the shaft, although not completely through their distal ends. Those two incisions then may be forced apart to form a pair of stabilizing segments, each of which being similar to the stabilizing segment illustrated in FIGS. 52-54.

The surgeon has the option of applying vacuum to adhere the tissue to the stabilizer 675. The surgeon also can use the port 685 and lumen to instead provide a solution to the tissue that the stabilizer is contacting. For example, the solution can be a therapeutic cooling or heating solution. The solution also can be a drug or other therapeutic agent. If the stabilizer is fabricated from a shape memory metal, the surgeon can pass a heating solution through the port 685 and lumen to cause the shape of the stabilizer (i.e., stabilizer segment 681) to reach its larger profile shape (FIG. 52). Then, when the stabilizer is to be removed from the body cavity, the surgeon injects a cold solution to cause the shape to return to the reduced profile configuration that is easily retracted into the tube 683 (FIG. 54). Of course, the stabilizer 675, in whole or in part, can be made from a superelastic material such that the surgeon merely pulls the handle to pull the stabilizer segment 681 back into the tube 683 to cause it to be in the reduced profile configuration in which the opening 689 is closed.

Referring to FIGS. 55-58, a stabilizer 700 can be configured to have any of the characteristics described above, such as vacuum application, fabricated from shape memory or superelastic materials, and/or with index markings. However, rather than having an enlarged portion and a curved surface to form a pivotable linkage between the arm or shaft and the stabilizer section, the stabilizer 700 includes a pivot mechanism 705 formed by the interaction of a first ridged surface 710 and a second ridged surface 715. The first ridged surface 705 is formed in a shaft 720 of the stabilizer segment 725. The second ridged surface 715 is formed in a lower clamp half 730 of a clamp mechanism 735 formed between the lower clamp half 730 and an upper clamp half 740. The lower clamp half 730 includes one or more wires, bands, or rods 743 that pass through the stabilizer to a handle 745. Applying force to the handle lever 750 pulls the wires 743 in the direction of the handle 745, which pulls the lower clamp half 730 in the direction of the upper clamp half 740. The ridged surfaces 710 and 715 then mate to fix the position of the stabilizer segment 725 relative to the stabilizer 700. A ratchet mechanism can be used in the handle to maintain the fixation of the clamp halves 730 and 740 until the procedure is completed. It is believed that the pivot mechanism 705 can be applied to any of the stabilizers described herein by one of ordinary skill in the art.

Referring to FIGS. 59-61, an alternative pivot mechanism 775 includes a first notched or ridged surface 777 and a second notched or ridged surface 779. The second notched or ridged surface 779 can be formed on one or more fins 781 formed on a pivot member 783. The notches or ridges on the surface 777 interact in a mating fashion with the notches or ridges in the surface 779. The fins 781 advantageously provide more flexibility than, for example, a ball and socket joint, such that the fins and surface 777 will interact to form a stronger fixation of the stabilizer segment and the stabilizer. The surfaces 779 can be randomly ridged or notched (FIG. 59) or have multiple vertical spikes 783 that fit into multiple vertical channels in the surface 777. Moreover, although four fins 781 are illustrated, fewer fins can be used or more fins can be used to provide satisfactory results.

Other methods of attaching the arm or shaft to the feet or stabilizer segment include an adjustable mechanism (e.g., macro and fine adjustment, vertical and horizontal adjustment), lockable mechanism, sliding mechanism, telescoping mechanism, and a side or top attachment. The feet or stabilizer segment can be attached to the side, top, or bottom of the arm, although only an attachment to the bottom of the arm is illustrated indepth herein.

Of course, the stabilizer can be part of a multi-component system that includes a custom or commercially available retractor and arm or rail system. Moreover, additional devices incorporating the technology described herein may be inserted through the chest cavity or additional medical devices can be used with the stabilizer. For example, one device, such as the stabilizer, may be inserted through one site, and another at a second site. Another device may be a heart retractor to support the heart, and/or section of the heart or other organ or tissue, during a cardiovascular surgical procedure, or other surgical or non-surgical procedure. The heart-positioning device advantageously supports the heart during a coronary artery bypass surgery in a manner that will not damage the heart, but yet will allow easy access to the surgical site without requiring the heart to be stopped and, moreover, while not unnecessarily constraining the heart. The heart positioner may also be used during conventional cardiopulmonary bypass supported procedures.

Moreover, as described in some detail above, the stabilizer, the heart position, retractors, or other surgical tools described herein can be used to heat or cool tissue in a therapeutic or injury-preventative manner that is separate from their intended use of stabilizing or retracting tissue. As described below, the stabilizer can include channels through which a circulating fluid is passed. Although the description below is directed to a stabilizer implementation, other surgical devices can be implemented using the technology and principles described herein. In one implementation, the stabilizer includes an elongated body through which a cooling fluid circulates to a tip portion that is adapted to contact tissue and cool or heat that tissue. The stabilizer may include a heat exchange region that is formed on an elongate shaft. The thermally transmissive core of the elongate shaft may comprise one or more fluid circulation paths or lumens such that heated or cooled fluid is passed into and/or extracted from the heat exchange region via the portion of the elongate shaft that is proximal to the heat exchange region. If the thermally transmissive core includes multiple fluid flow lumens, a heat exchange fluid may be circulated into or through the heat exchange region via such lumens.

Another method that can be used is a cryogenic method that includes providing a phase change coolant that is pumped as a liquid to the tip of the stabilizer and undergoes its phase change in a small chamber located at the tip, for example on the tip of the stabilizer segment. The wall of the chamber contacts adjacent tissue directly to provide the cooling or ablation treatment. Such a stabilizer can treat or achieve a relatively high rate of heat energy transfer. By employing a phase change refrigerant that can be injected at ambient temperature along the body of the stabilizer and undergo expansion at the tip, the cooling effect may be restricted to the localized treatment region surrounding the tip portion of the stabilizer. The dimensions of stabilizer construction require that the phase change coolant be released from a nozzle or tube opening at a relatively high pressure, into a relatively small distal chamber of the stabilizer. After the fluid expands in the distal chamber and cools the walls, it is returned through the body of the stabilizer to a coolant collection system, preferably in the form of a recirculation loop by, for example, a pump.

The cryogenic fluid can be provided in a liquid or a gas state. An extremely low temperature can be achieved within the stabilizer, and more particularly on the surface of the stabilizer, by cooling the fluid to a predetermined temperature prior to its introduction into the stabilizer, by allowing a liquid state cryogenic fluid to boil or vaporize, or by allowing a gas state cryogenic fluid to expand. Some liquids that can be used for this cooling include chlorodifluoromethane, polydimethylsiloxane, ethyl alcohol, and HFC's such as AZ-20 (a 50-50 mixture of difluoromethane and pentafluoroethane sold by Allied Signal). Some gasses that can be used for this type of cooling include nitrous oxide and carbon dioxide The cooling element of the stabilizer can include a means for cooling with liquid nitrogen or a Peltier cell. A temperature sensor, such as a thermocouple, is used to sense the surrounding temperature, for example, of the tissue and/or the device components. A controller is connected to the sensor and receives the sensed temperature from the temperature sensor and is configured to control the amount of power that is supplied to the thermal element and change the temperature of a probe tip or to change the temperature of the contacted tissue.

Similarly, the stabilizers and retractors described herein can be used as a cryoprobe, cryosurgical ablation device, and/or cryostat and cryocooler for cryosurgery as a separate procedure or as an adjunct to tissue stabilization. The stabilizer can use Joule-Thomson cooling in the same manner as Joule-Thomson cryostats. These devices take advantage of the characteristic that most gases when rapidly expanded become extremely cold. In these devices, a high pressure gas such as argon or nitrogen is expanded through a nozzle inside a small cylindrical sheath, made of a metal or ceramic, and the Joule-Thomson expansion cools the sheath to sub-freezing cryogenic temperature very rapidly, which is transferred to surrounding tissue. One example of this type of device, although not a stabilizer, is illustrated in Sollami, U.S. Pat. No. 3,800,552, which shows a basic Joule-Thomson probe with a sheath made of metal, a fin-tube helical gas supply line leading into a Joule Thomson nozzle which directs expanding gas into the probe. Expanded gas is exhausted over the fin-tube helical gas supply line, and pre-cools incoming high pressure gas. The coiled supply line is referred to as a heat exchanger and is beneficial because as it pre-cools incoming gas, it allows the probe to obtain lower temperatures.

In another implementation, the stabilizer can use the general concepts of Joule-Thomson devices to be configured as a device that is used first to freeze tissue and then to thaw the tissue with a heating cycle. In this implementation, nitrogen is supplied to a Joule-Thomson nozzle for the cooling cycle, and helium is supplied to the same Joule-Thomson nozzle for the warming cycle. The surfaces of the stabilizer to which the heating and cooling occur can be in contact with tissue to provide a therapeutic effect.

In another implementation, the stabilizer can be implemented as a cryocooler for mass flow warming, with flushing backwards through the stabilizer, to warm the stabilizer after a cooling cycle. In this implementation, the stabilizer includes a supply line for high pressure gas to flow to a Joule-Thomson expansion nozzle and a second supply line for the same gas to be supplied without passing through a Joule-Thomson nozzle, thus warming the stabilizer with mass flow.

The stabilizer also can be implemented as a cryoprobe that uses a fin-tube helical coil heat exchanger in a high pressure gas supply line to a Joule-Thomson nozzle. The stabilizer would have a second inlet for a warming fluid, and would provide warming with mass flow of gas supplied at approximately 100 psi.

The stabilizer also can be implemented as a heat exchanger that includes a Giaque-Hampson heat exchanger with finned tube gas supply line coiled around a mandrel. After expansion of the gas in the tip of the stabilizer, the gas next flows over the coils and exhausts out the proximal end of the stabilizer. The flow of the exhaust gas over the heat exchanger coils is controlled by placement of a flow-directing sheath that is placed in different longitudinal areas of the heat exchanger.

In another implementation of a tissue cooling stabilizer, retractor, or other surgical device, one or more parallel finned tubes can be used to create a dual helix design. In this implementation, two parallel gas supply lines are used, and are wound in parallel around a mandrel. Dual coils also can be used to supply high pressure gas which cools upon expansion (e.g., nitrogen, argon, $NO_2$, $CO_2$), so that both coils are used for cooling. One coil can be used for cooling gas while the other coil is used for the supply of a high pressure gas which heats upon expansion (hydrogen, helium, and neon).

In another implementation of a cooling and heating stabilizer, separate cooling and heating Joule-Thomson nozzles are used when the heating gas is supplied through a mandrel. In this implementation, the heating gas supply is not subject to heat exchange with the exhausting heating gas to create a higher initial heating rate. To permit complete control of both heating and cooling, such a cryostabilizer is supplied with gas through a dual manifold which allows for independently warming or each portion of the stabilizer segment. If the stabilizer is a dual handle stabilizer with independent stabilizers (FIGS. 48 and 49) this allows removal of individual stabilizers in the event that the surgeon decides that a cryostabilizer must be moved. It also allows protective warming for nearby anatomical structures.

In another implementation of a cyrostabilizer, a medium flows in a first lumen of the stabilizer, is pressurized, and is at a first temperature just distal of an expansion element. Upon passage through that expansion element, the medium flows into a second lumen that is comparatively at a lower pressure and temperature. This cooled medium is sufficient for cooling the tissue when the second lumen is appropriately placed in relation to the tissue. The second lumen can include a bellows portion for contacting the tissue and a cooling portion along the bellows portion for cooling the tissue. The bellows portion is constructed to facilitate contact between the cooling portion, or contact portion, of the cryostabilizer and the tissue. As such, the bellows portion may be longitudinally fixed, or longitudinally expandable or contractible. Moreover, at least the contact portion may be composed of a superelastic metal alloy, such as nitinol, to provide desirable flexibility, strength, and longevity. Because of these desirable properties, the entire bellows portion may be composed of this material.

The expansion means of the cryostabilizer may be a media-flow restriction device, such as an orifice sufficient for Joule-Thomson expansion of the medium flowing therethrough. The expansion means may be longitudinally moveable so that the tissue contacting portion can be moved to a desirable longitudinal position along the bellows portion for optimal cooling of the selected tissue.

The cryostabilizer may be advantageously employed over an operating temperature range of approximately normal body temperature to a desirable cooling temperature. For example, the cooling temperature at the contact portion may be at less than or equal to approximately 0° C. to provide adhesion of the contact portion of the stabilizer to the selected tissue. The cooling temperature also may be as low as approximately −10° C. to provide cold-mapping of cardiopulmonary tissue. This cooling temperature of the cryostabilizer may be lower, for example, from approximately −20° C. to approximately −150° C., and more particularly, from about −70° C. to about −120° C., for forming an efficacious lesion in biological tissue.

The medium supplied in the cryostabilizer to the first lumen may be pre-cooled so that it is at a desirably low temperature before it reaches the expansion means for further cooling. Namely, a conduit having a pre-cooling medium flowing therethrough may be positioned in an efficacious heat-exchange relationship with the first lumen of the cryostabilizer to pre-cool the medium flowing in the first lumen. Moreover, a second lumen of the cryostabilizer may be in an efficacious heat-exchange relationship with the first lumen for further cooling of the medium flowing in the first lumen. With such heat-exchange relationships, the cryostabilizer can achieve a very low cooling temperature. Furthermore, the pre-cooling and cooling media may be selected to achieve, efficaciously, the cooling desired.

Referring to FIGS. 62-64, the principles described herein can be applied to other surgical devices, such as a superelastic or shape memory tissue retractor 800. Such retractors can be used, for example, during minimally invasive heart valve surgery or even other non-cardiovascular minimally invasive surgeries (e.g., laparoscopic, endoscopic, robotically assisted, and port access surgeries). The retractor 800 includes a handle 805, an arm 810, a foot 815, and a delivery tube 820. The handle includes one or more ports 825 that are used, for example, to supply vacuum or a fluid. The port 825 connects to one or more channels (not shown) that pass through the handle 805 and the arm 810 and terminate in the foot 815. The foot 815 includes an atraumatic surface 830 and openings 835 that connect to one or both of a vacuum line and a fluid line that are part of the channels connected to the ports 825. As such applying a vacuum to one of the ports will create a vacuum at the openings 835.

The arm 810 and/or foot 815 can be fabricated from either a shape memory material or a superelastic material. If a superelastic material is used to fabricated either or both of the arm 810 and foot 815, the arm and foot can be bent such that they can be inserted into the delivery tube 820 for delivery through a narrow opening into a body cavity (FIG. 62). Then, the surgeon advances the handle 805 relative to the delivery tube 820 to advance the foot 815 from the delivery tube. If made from a superelastic material, the foot 815 will return to its unconstrained shape (FIG. 64). The unconstrained shape can be that of an L or some other suitable shape for positioning, grasping, retracting, or otherwise manipulating an organ, tissue, or vessel. The openings 835 are positioned on the foot to be adjacent to the tissue in contact with the foot 815 so that if vacuum is applied to the retractor 800, the vacuum will further secure the tissue to the foot.

If the retractor 800 is made in whole or in part from a shape memory material, the surgeon can use heating or cooling to change the shape of the retractor. For example, the surgeon places the arm 810 and foot 815 in the delivery tube 820 with the arm and foot in a constrained position. Then, the surgeon advances the handle 805 to advance the foot 815 out of the delivery tube 820. As shown in FIG. 63, because the retractor is made from a shape memory material, it will not immediately return to it unconstrained shape. Instead, by applying a heating solution through one of the ports 825, the heating solution will pass through the handle 805, the arm 810, and into the foot 815 such that the shape of the foot 815 returns to its unconstrained position (FIG. 64). The channel through which the heating solution flows can be open to separate openings 835a or closed. If open to the openings 835a, the heating solution will irrigate the surgical field at the same time that it heats the shape memory material and causes the material to return to its unconstrained configuration. If the channels do not flow into openings, a heating solution can be repeatedly infused and withdrawn until the retractor returns to the unconstrained configuration. In one implementation, a dual lumen catheter is inserted into the port and passed into the foot. One lumen of the catheter is used to inject the heating solution and the second lumen is used to withdraw the heating solution. When the retractor is to be removed, the surgeon can then apply a cooling solution into the port 825 to cool the arm 810 and foot 815. The cooled arm and foot then can be easily retracted into delivery tube 820 and the delivery tube and stabilizer withdrawn from the body cavity. Alternatively, the surgeon can simply retract the handle 805 to pull the foot back into the delivery tube relying on the resilience of the arm and foot to fit the foot into the tube.

As explained above, the retractor can include one or more channels. One or more of the channels can be used to infuse therapeutic or preventative agents into the surgical field. The channels also can be used to deliver a catheter-based light fiber to illuminate the surgical field, a RF-device (e.g., for coagulating, cutting, and/or ablating tissue), a gas to expand the body cavity surrounding the surgical field, and/or an instrument or catheter-based device to manipulate the surgical field. For example, a catheter-based biopsy device can be passed through one of the channels to take a tissue biopsy. Moreover, the channels can be used to receive rigidifying mandrils or shaping mandrils to shape the retractor. Although FIGS. 62-64 illustrate the application of vacuum, the devices can be configured as simply as superelastic tubes that pass through delivery tubes or with any of the individual features described above.

Figure 65:
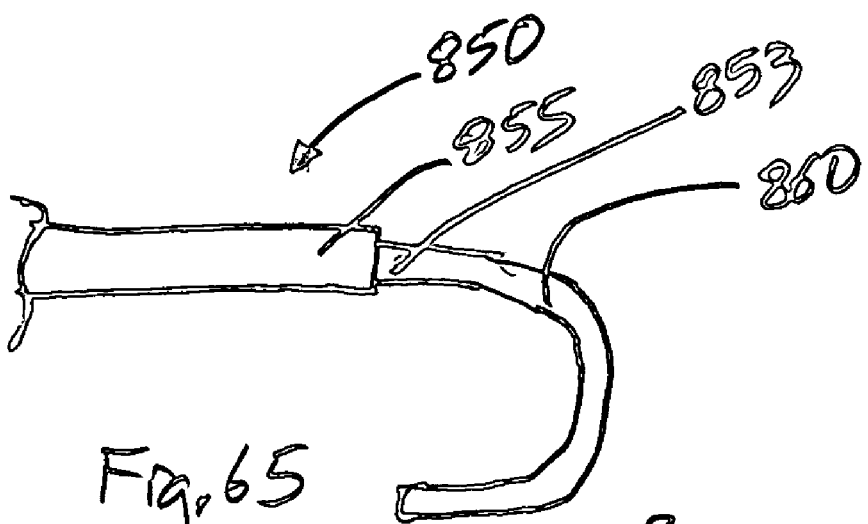
FIGS. 65 and 66 are side views of a shape memory/superelastic surgical device including a J-shaped surgical instrument.
Figure 66:
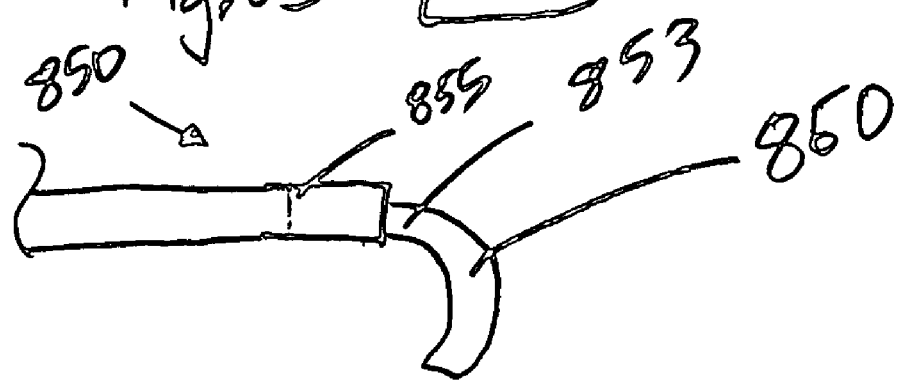

Similarly to FIGS. 62-64, a surgical device or tool, such as a retractor, can be formed with other shapes that are useful in a wide range of surgical procedures. For example, referring to FIGS. 65 and 66, the instrument can have a J shape, or referring to FIGS. 67 and 68, the instrument can have a hockey stick shape. As illustrated in FIGS. 65 and 66, surgical device 850 includes a J-shaped instrument 853 that is passed through a delivery tube 855 such that a J-shaped portion 860 of the instrument is delivered to a surgical site to move, reposition, or manipulate tissue. The device 850 can be advanced in part or in whole from the delivery tube 855 such that the instrument 853 forms a curved shape that varies between a slightly curved shape and a complete J-shape.

Figure 67:
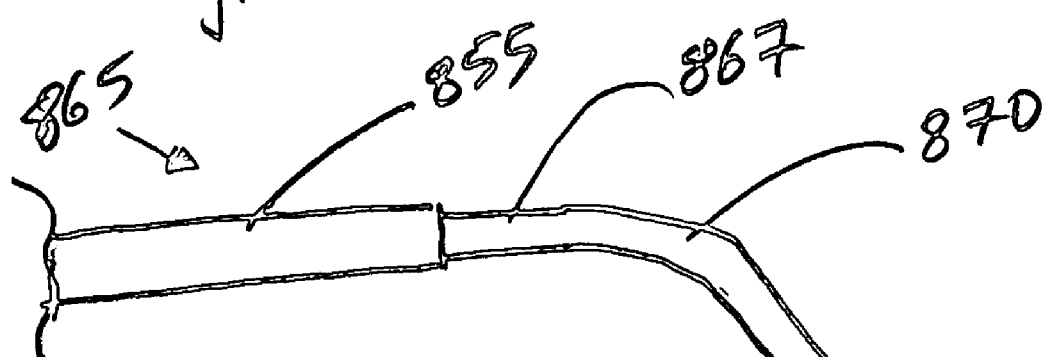
FIGS. 67 and 68 are side view of a shape memory/superelastic surgical device including a hockey stick shaped surgical instrument.
Figure 68:
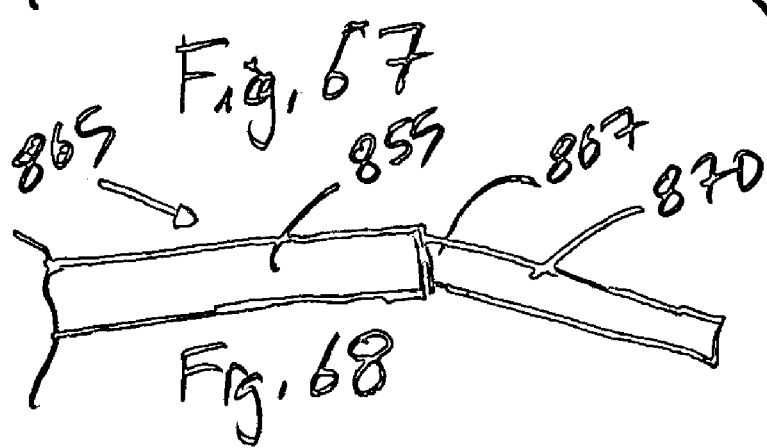

Similarly, in FIGS. 67 and 68, a surgical device 865 includes a hockey stick shaped instrument 867 that has a hockey-stick shaped portion 870 that can be advanced in whole or in part from the delivery tube 855 such that the instrument forms an angled member that varies with respect to the delivery tube between collinear to any desired angle based on the angle imparted in the instrument 867 during fabrication.

The surgical devices 850 and 865 can be fabricated from the same materials as the devices of FIGS. 62-64 and be used in the same manner for similar purposes (e.g., deliver heat, provide cooling, deliver instruments, deliver therapeutic agents, etc.). Moreover, any or all of the features shown in the devices of FIGS. 62-64 can be implemented in the device 850 and 865.

Figure 69:
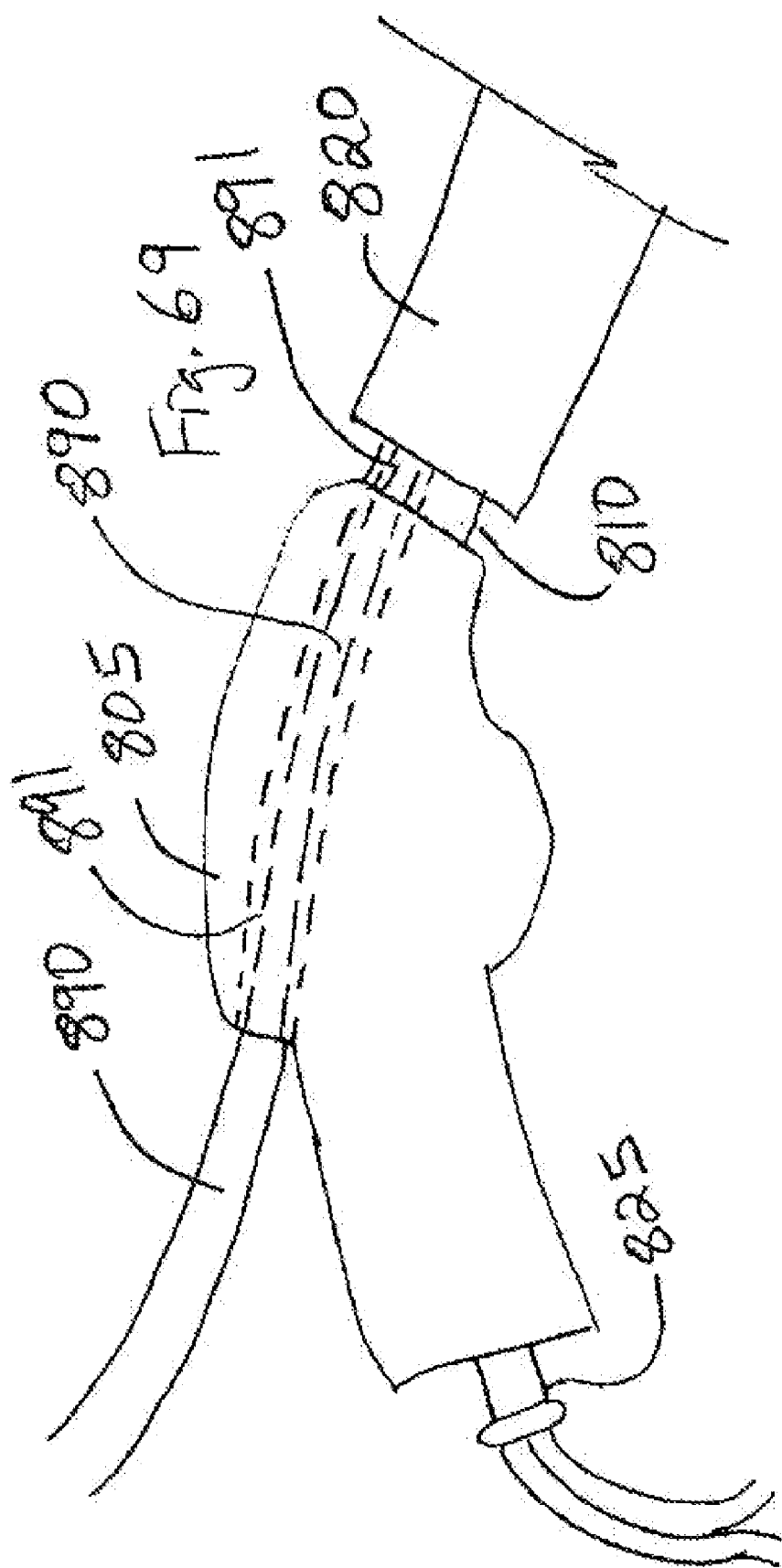
FIGS. 69, 70, and 71 are side views showing the stabilizer or retractor being used as a carrier to pass a therapeutic or diagnostic device through a lumen in the stabilizer or retractor into an opening, groove, slot, or hole in a stabilizing segment, feet, and/or contacting surface.
Figure 70:
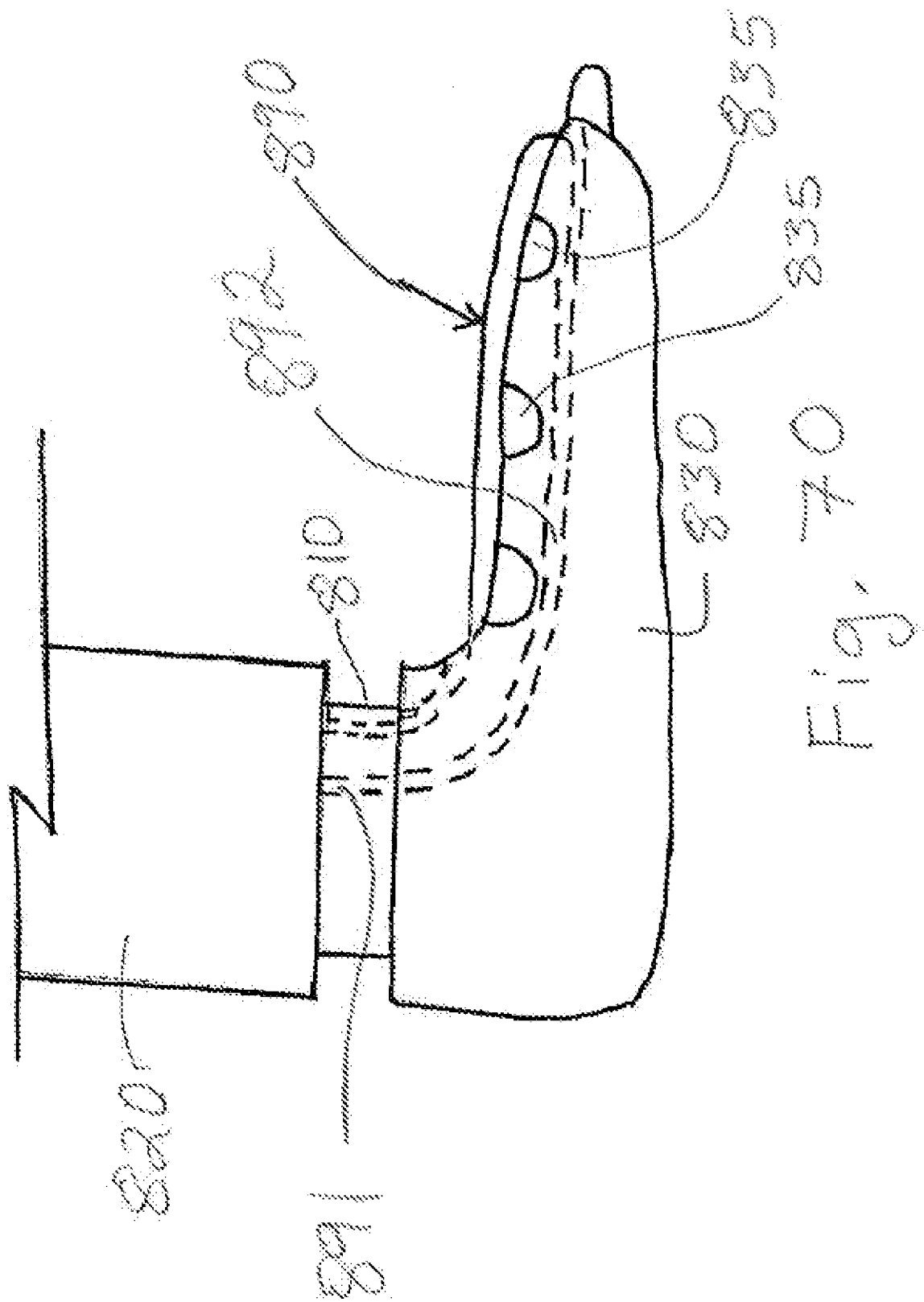
Figure 71:
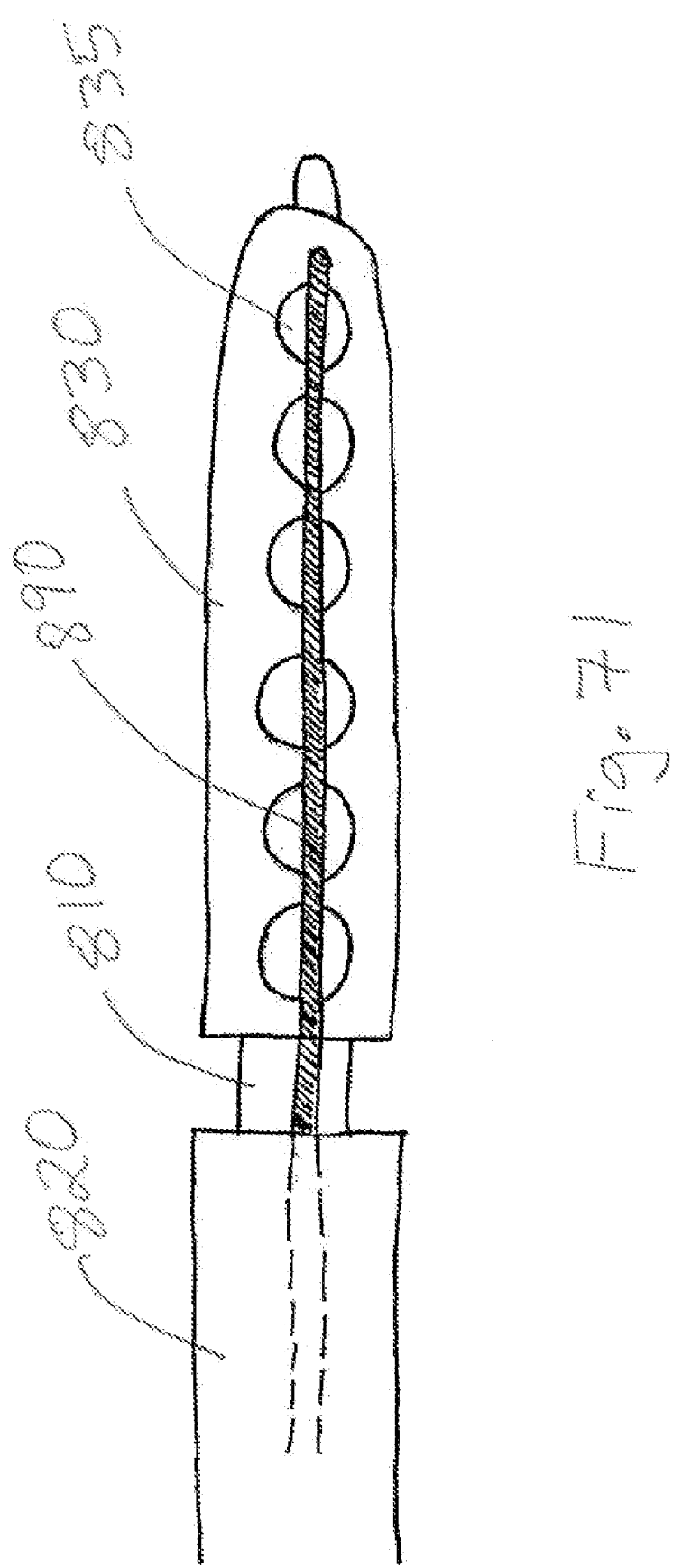

While several particular forms of the invention, have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. For example, the arm segment or shaft can be configured to provide more stable locking to the arm, retractor or rail by knurling the shaft, providing a matching interlocking geometry to the arm, retractor or rail, etc. The stabilizing segment, feet, and/or contacting surface may be dimpled or roughened to reduce slippage against the tissue. As illustrated in. FIGS. 69-71, and with reference to FIGS. 62-64, the stabilizer also can be used as a carrier for a therapeutic or diagnostic device 890, such as an electrophysiology catheter or other device for performing tissue ablation, such as exterior pulmonary vein ablation for treating atrial fibrillation. When used in this manner, the top and sides of the foot pads or feet can function as a thermal insulator to prevent secondary thermal damage to surrounding or adjacent tissue. Because the stabilizer also functions to maintain sufficient contact against tissue, the stabilizer thus can be used to carry a therapeutic or diagnostic device or catheter 890 to the tissue to perform a diagnostic or therapeutic procedure. Alternatively, a catheter or other device 890 can be passed through a lumen 891 in the stabilizer and/or into an opening, groove, slot, or hole 892 in the stabilizing segment, feet, and/or contacting surface to perform a diagnostic or therapeutic procedure on the tissue in which the stabilizer is in contact. The device can be used during conventional suturing of an artery in a coronary artery bypass grafting procedure, as well as in the placement of sutureless anastomotic connectors. Accordingly, it is not intended that the invention be limited, except as by the appended claims.

We claim:

1. A surgical instrument for temporary use in a medical procedure in a mammalian body, the surgical instrument being configured to be changed between a first shape and a second different shape upon application of one or both of heating and cooling, the instrument comprising:
   a first member;
   a second member having a surface configured to contact and stabilize tissue such that a surgical procedure can be performed on the stabilized tissue;
   means for applying heating or cooling to one or both of the first member and the second member to change the shape between the first shape and the second different shape; and
   a delivery tube surrounding at least a portion of a length of either or both of the first member and the second member, the second member configured to fit within the delivery tube in either the first shape or the second shape but not in both the first shape and the second shape.

2. The surgical instrument of claim 1, wherein application of cooling causes one or both of the first member and the second member to become malleable.

3. The surgical instrument of claim 1, wherein application of heating causes one or both of the first member and the second member to change shape.

4. The surgical instrument of claim 3, wherein the application of heating comprises one or both of supplying a heated fluid to one or both of the first member and the second member and receiving in one or both of the first member and the second member the heat generated by the mammalian body.

5. The surgical instrument of claim 1, wherein application of cooling causes the surface configured to contact tissue to adhere to the tissue.

6. The surgical instrument of claim 1, further comprising a source to apply vacuum to the surgical instrument, wherein the second member includes at least one opening passing through the surface configured to contact tissue and the application of vacuum to the surgical instrument adheres the surface configured to contact tissue to the tissue.

7. The surgical instrument of claim 1, further comprising one or more channels in one or both of the first member and the second member.

8. The surgical instrument of claim 7, wherein the channels are configured for one or more of application of vacuum, application of heating, application of cooling, application of a therapeutic agent, application of a second surgical instrument, and application of shaping mandrils, whereby the mandrils impart a shape in, or rigidify, one or both of the first member and the second member.

9. The surgical instrument of claim 1, wherein the second member comprises one or more feet, each of the feet including a surface configured to contact tissue.

10. The surgical instrument of claim 9, wherein the surface configured to contact the tissue comprises a removable component for removably attaching to each of the feet.

11. The surgical instrument of claim 1, wherein the first member is connected to the second member by a pivotal joint comprising a finned surface that pivotally mates with a curved surface.

12. The surgical instrument of claim 11, further comprising a handle extending from the first member, the handle including a nonthreaded thumb slide to lock the finned surface against the curved surface to fix the position of the first member relative to the second member.

13. The surgical instrument of claim 1, further comprising a delivery tube, a third member and a fourth member having a surface configured to contact tissue, wherein the second member and the fourth member include feet, each of the feet including the surface configured to contact tissue, and the feet are separately controllable by controlling the movement of the first member and the second member.

14. The surgical instrument of claim 1, wherein the surgical instrument comprises one or both of a tissue retractor and a tissue stabilizer.

15. The surgical instrument of claim 1, wherein the surgical instrument comprises a shape memory material.

16. A surgical instrument for temporary use in a medical procedure in a mammalian body to be placed in contact with tissue, the surgical instrument being configured to be changed between two different shapes upon removal of a constraining force, the instrument comprising:
   a handle;
   a first member including a lumen configured to receive a second surgical instrument;
   a second member having at least one opening configured to receive the second surgical instrument and a surface configured to contact and stabilize tissue such that a surgical procedure can be performed on the stabilized tissue, the first member being connected at a first end to the second member and at a second end to the handle; and
   a constraining means to apply a constraining force to one or both of the first member and the second member to cause one or both of the first member and the second member to be in a first constrained shape, wherein the first member and the second member comprise a nickel titanium alloy, the nickel titanium alloy having an elastic property that causes one or both of the first member and the second member to have a second unconstrained shape that is different from the first constrained shape and causes one or both of the first member and the second member to change between the two different shapes upon removal of the constraining force, and the constraining means comprises a delivery tube.

17. The surgical instrument of claim 16, wherein the constraining means is configured to be moved relative to the first member and the second member to remove the constraining force from one or both of the first member and the second member to allow one or both of the first member and the second member to return to an unconstrained shape.

18. A method of providing a surgical instrument for temporary use in a medical procedure in a mammalian body, the method comprising:

providing a surgical instrument fabricated from a shape memory material and being configured to be changed between two different shapes in the mammalian body upon application of one or both of heating and cooling, the surgical instrument comprising:
  a delivery tube, a first member, a second member having a surface configured to contact and stabilize tissue such that a surgical procedure can be performed on the stabilized tissue, and a means to apply heating or cooling to one or both of the first member and the second member to change the shape between a first shape and a different second shape;
applying cooling to one or both of the first member and the second member and placing one or both of the first member and the second member into the delivery tube in a first shape;
advancing the delivery tube in the mammalian body;
advancing the first member and the second member in the delivery tube such that at least one of the first member and the second member extend out of the delivery tube into the mammalian body;
applying heating to one or both of the first member and the second member to change the shape of one or both of the first member and the second member from the first shape to a second shape;
using the second member to contact and stabilize tissue; and
removing the surgical instrument from the mammalian body.

19. The method of claim 18, wherein the surgical instrument is used in one or more of minimally invasive valve surgery, stabilization of tissue, retracting tissue, delivery of vacuum to tissue, application of heating to tissue, application of cooling to tissue, application of a therapeutic agent, application of a second surgical instrument, and application of shaping mandrils through channels in the first member and/or second member, whereby the mandrils impart a shape in, or rigidify, one or both of the first member and the second member.

* * * * *